(12) United States Patent
Desimone et al.

(10) Patent No.: US 11,786,543 B2
(45) Date of Patent: *Oct. 17, 2023

(54) COMPOSITIONS COMPRISING DECITABINE AND TETRAHYDROURIDINE AND USES THEREOF

(71) Applicant: The Board of Trustees of the University of Illinois, Urbana, IL (US)

(72) Inventors: Joseph Desimone, Glen Ellyn, IL (US); Yogen Saunthararajah, Cleveland, OH (US)

(73) Assignee: BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/375,585

(22) Filed: Jul. 14, 2021

(65) Prior Publication Data
US 2022/0023328 A1 Jan. 27, 2022

Related U.S. Application Data

(63) Continuation of application No. 16/685,956, filed on Nov. 15, 2019, now Pat. No. 11,096,953, which is a continuation of application No. 15/875,727, filed on Jan. 19, 2018, now Pat. No. 10,517,884, which is a continuation of application No. 15/044,805, filed on Feb. 16, 2016, now Pat. No. 9,895,391, which is a continuation of application No. 13/414,546, filed on Mar. 7, 2012, now Pat. No. 9,265,785, which is a continuation-in-part of application No. 13/141,669, filed as application No. PCT/US2009/069035 on Dec. 21, 2009, now Pat. No. 9,259,469.

(60) Provisional application No. 61/486,428, filed on May 16, 2011, provisional application No. 61/158,937, filed on Mar. 10, 2009, provisional application No. 61/139,710, filed on Dec. 22, 2008.

(51) Int. Cl.
*A61K 31/7068* (2006.01)
*A61K 45/06* (2006.01)

(52) U.S. Cl.
CPC .......... *A61K 31/7068* (2013.01); *A61K 45/06* (2013.01)

(58) Field of Classification Search
CPC . A61K 2300/00; A61K 31/7068; A61K 45/06
See application file for complete search history.

(56) References Cited

U.S. PATENT DOCUMENTS

| 4,894,364 | A | 1/1990 | Greer |
| 6,905,669 | B2 | 6/2005 | DiMartino |
| 9,259,469 | B2 * | 2/2016 | Desimone .......... A61K 31/7068 |
| 9,265,785 | B2 * | 2/2016 | Desimone .......... A61K 31/7072 |
| 9,895,391 | B2 * | 2/2018 | Desimone ................ A61P 7/06 |
| 10,517,884 | B2 * | 12/2019 | Desimone ................ A61P 7/00 |
| 11,096,953 | B2 | 8/2021 | Desimone |
| 2001/0025032 | A1 | 9/2001 | Von Borstel |
| 2003/0077297 | A1 | 4/2003 | Chen |
| 2004/0204339 | A1 | 10/2004 | DiMartino |
| 2006/0074046 | A1 | 4/2006 | Redkar |
| 2008/0057086 | A1 | 3/2008 | Etter |

FOREIGN PATENT DOCUMENTS

| CA | 2750891 | 8/2018 |
| EP | 2381780 | 2/2015 |
| WO | 2010075301 | 7/2010 |

OTHER PUBLICATIONS

Beumer, J, et al.; "Plasma pharmacokinetics and oral biovailability of 3,4,5,6-tetrahydrouridine, a cytidine deaminase inhibitor, in mice", Cancer Chemotherapy Pharmacol, (2008) 62:457-464; 8 pages.

Desimone, J., et al.; "Tetrahydrouridine, Cytidine Analogues, and Hemoglobin F", American Journal of Hematology, 18:283,288 (1985); 6 pages.

Eliopoulos, N., et al., "Drug resistance to 5-aza-2'-deoxycytidine, 2',2'-difluorodeoxycytidine, and cytosine arabinoside conferred by retroviral-mediated transfer of human cytidine deaminase cDNA into murine cells," Cancer Chemother Pharamcol (1998), 42:373-378; 6 pages.

Freireich, E. et al., "Quantitative Comparison of Toxicity of Anticancer Agents in Mouse, Rat, Hamster, Dog, Monkey, and Man," Cancer Chemotherapy Reports, vol. 50, No. 4, May 1966, pp. 219-244, 28 pages.

Laliberte, J. et al., "Potent inhibitors for the deamination of cytosine arabinoside and 5-aza-2'-deoxycytidine by human cytidine deaminase," Cancer Chemotherapy and Pharmacology (1992) 30:7-11; 6 pages.

Lavelle, D, et al., "Oral decitabine reactivates expression of the methylated y-globin gene in Papio anubis", American Journal of Hematology; 2007; pp. 981-985; 5 pages.

* cited by examiner

*Primary Examiner* — Pancham Bakshi
(74) *Attorney, Agent, or Firm* — Schwabe, Williamson & Wyatt, P.C.

(57) ABSTRACT

Embodiments of compositions and methods for the treatment of blood disorders and malignancies in a subject are described herein. In one embodiment, a composition for the treatment of a blood disorder or a malignancy in a subject comprises decitabine, tetrahydrouridine, and an excipient. In another embodiment, a method for the treatment of a blood disorder or a malignancy in a subject comprises the oral administration of a composition comprising decitabine and tetrahydrouridine. In some examples, the composition may be administered 1-3 times weekly.

14 Claims, 41 Drawing Sheets

| Sample N# | WHO Type | Cytogenetic Abnormalities |
|---|---|---|
| 1 | Normal | Normal |
| 2 | Normal | Normal |
| 3 | Normal | Normal |
| 4 | Normal | Normal |
| 5 | AML, unspecified | +8, +19, +21 |
| 6 | RCMD | Normal |
| 7 | 5q- syndrome | 5q- |
| 8 | AML, unspecified | Normal |
| 9 | AML, M2 | -Y |
| 10 | AML, unspecified | Normal |
| 11 | AML, unspecified | inv16 |
| 12 | AML, M1 | Normal |
| 13 | AML, unspecified | Normal |
| 14 | AML, unspecified | Normal |
| 15 | AML, unspecified | Normal |
| 16 | AML, unspecified | +8, +19, +21 |
| 17 | AML, unspecified | Normal |
| 18 | AML, M4 | t(6, 11), +3, +8, +13, +14, +19, +21 |
| 19 | AML, M5 | Normal |
| 20 | AML, unspecified | +21, +Y |

Fig. 9C

COMPOSITIONS COMPRISING DECITABINE AND TETRAHYDROURIDINE AND USES THEREOF

CROSS REFERENCE TO RELATED APPLICATIONS

The present application is a continuation of, and claims priority to U.S. patent application Ser. No. 16/685,956, filed Nov. 15, 2019 which claims priority to U.S. patent application Ser. No. 15/875,727, filed Jan. 19, 2018, which is a continuation of Ser. No. 15/044,805, filed Feb. 16, 2016, now U.S. Pat. No. 9,895,391, issued on Feb. 20, 2018, which is a continuation of U.S. patent application Ser. No. 13/414,546, filed on Mar. 7, 2012, now U.S. Pat. No. 9,265,785, issued on Feb. 23, 2016, which in turn claims priority to U.S. Provisional Application No. 61/486,428, filed May 16, 2011, and is a continuation-in-part of U.S. patent application Ser. No. 13/141,669, now U.S. Pat. No. 9,259,469, issued Feb. 16, 2016, which was filed Aug. 5, 2011 as a national phase entry of International Application No. PCT/US2009/069035, filed Dec. 21, 2009, entitled "COMPOSITIONS COMPRISING DECITABINE AND TETRAHYDROURIDINE AND USES THEREOF," which in turn claims priority to U.S. Provisional Application Nos. 61/158,937, filed Mar. 10, 2009, and 61/139,710, filed Dec. 22, 2008. The entire disclosures of these applications are hereby incorporated by reference in their entireties.

STATEMENT OF RIGHTS TO INVENTIONS MADE UNDER FEDERALLY SPONSORED RESEARCH

This invention was made with government support under Grant/Contract No. HL090513 awarded by the National Institutes of Health (NIH). The government has certain rights in the invention.

TECHNICAL FIELD

Embodiments herein relate to the treatment of blood disorders and malignancies. More specifically, disclosed herein are compositions and methods for the treatment of blood disorders and malignancies in a subject, which methods comprise the oral administration of a composition comprising decitabine and tetrahydrouridine.

BACKGROUND

SCD is a serious congenital disease which affects 1 in 500 African-Americans, as well as individuals of other racial backgrounds, exacting a substantial toll in morbidity and mortality upon the approximately 100,000 Americans afflicted. SCD patients can have frequent episodes of severe, debilitating pain, often requiring emergency room visits or hospitalization, and time off from work or school. Although some patients respond to hydroxyurea (HU, the standard treatment for symptomatic patients), and a few may be candidates for allogeneic stem cell transplantation, most patients continue to suffer. Furthermore, HU is used at doses that cause acute DNA damage and cytotoxicity, and has potential genotoxic, teratogenic and anti-fertility effects. Similarly, allogeneic stem cell transplantation is performed with cytotoxic conditioning and attendant risks of treatment-related mortality.

A clinical research effort to develop pharmacologic inducers of HbF expression culminated in FDA approval of the anti-metabolite HU to treat symptomatic SCD in 1998. A recent follow-up of patients enrolled in the pivotal HU trial confirmed that a decreased risk of mortality in these patients correlates with HbF levels (Steinberg, M. H., et al. 2003 JAMA 289: 1645-1651; Rosse, W. F., et al. 2000 Am Soc Hematol Educ Program 2-17). However, HbF levels are not increased in approximately 40% of HU compliant patients (Steiberg, M. H., et al. 1997 Blood 89: 1078-1088; Steinberg, M. H., et al. 1999 Expert Opin Investig Drugs 8:1823-1836; Atweh, G. F., et al. 2001 Curr Opin Hematol 8:123-130). Finally, HU is used at DNA-damaging, cytotoxic doses, potentially compounding the bone marrow damage that accumulates in SCD.

Most cells in the body, including cancer cells or blood disorder cells, such as sickle cells, contain the same complement of genes. The function and specialization of a cell is, therefore, determined by which of these genes are turned-on (activated), and which are turned-off (repressed). Activation refers to the expression of the protein encoded by the gene, while repression of the gene implies that the protein encoded by that gene is expressed at lower levels or not at all. DNA methyl-transferase 1 (DNMTI) is an enzyme which plays a critical and central role in the machinery that represses genes. Therefore, altering the levels of DNMTI within a cell can have powerful effects on the pattern of gene-expression, function and specialization of a cell.

Decitabine (5-aza-2'-deoxycytidine) is a nucleoside analogue drug—a drug that mimics a natural component of DNA. Decitabine is relatively unique amongst the large family of nucleoside analogue drugs in that it can irreversibly bind to and deplete DNMTI.

Cytidine deaminase (CAD) is an enzyme that is highly expressed in the liver and intestine and rapidly destroys decitabine within the body. Tetrahydrouridine (THU) is a safe and well-tolerated pyrimidine nucleoside analogue that inhibits cytidine deaminase. In humans, the cytidine deaminase gene is subject to non-synonymous single nucleotide polymorphisms which produce variants of cytidine deaminase that have differences in enzymatic activity of 3-fold or more (Gilbert, J. A., et al. 2006 Clin Cancer Res 12, 1794-1803; Kerch, H. C., et al. 1998 Exp Hematol 26, 421-425; Yue, L., et al. 2003 Pharmacogenetics 13, 29-38).

SUMMARY

Historically, decitabine was developed as an anti-metabolite or DNA damaging drug intended to kill cancer cells by causing extensive damage within the cells. Its clinical or experimental application has not been optimized for the depletion of DNMTI. With an objective of using decitabine to deplete DNMTI to change cell behavior, antimetabolite effects that kill cells are undesirable. Optimization of decitabine to deplete DNMTI without causing other 'off-target' or toxic effects is desired.

Optimizing decitabine to deplete DNMTI in vivo can have powerful therapeutic benefits in a spectrum of diseases such as sickle cell disease, thalassemia, and cancers of multiple tissues. For example, in sickle cell disease and β-thalassemia, by depleting DNMTI, decitabine prevents the repression of the fetal hemoglobin (HbF) gene. The resulting increase in Hb abrogates the disease-causing effects of the abnormal sickle or thalassemia genes. Furthermore, the DNMTI depletion by decitabine changes blood cell specialization, so that more red blood cells are made, further addressing the debilitating anemia of these conditions.

In cancer cells, DNMTI depletion by decitabine prevents the repression of differentiation genes and renews the differentiation of the cancer cells—the abnormal growth of the cancer cells is caused by a block in their normal differentiation process, which is relieved by decitabine. Of especial note, DNMTI depletion in normal stem cells increases their self-renewal; that is, DNMTI depletion increases the number of normal stem cells—the opposite of its effects on cancer cells. Therefore, DNMTI depletion by decitabine could be an effective and very safe, well-tolerated cancer therapy.

Because of decitabine's unique ability to deplete DNMTI, and, therefore, alter the gene expression, function, and specialization of cells, and because DNMTI depletion by regimens of decitabine designed to deplete DNMTI without causing DNA damage increases HbF, and produces clinical improvement even in sickle cell disease patients with severe illness despite standard of care (Saunthararajah, et al. 2008 Brit J Haematol 141(1): 126-9), decitabine is contemplated for treatment of these and other patients.

Because DNMTI depletion by decitabine induces the terminal differentiation and apoptosis of cancer cells, while increasing the self-renewal of normal stem cells (opposite effect on cancer cells versus normal stem cells), decitabine is additionally contemplated for treatment of these patients.

In one embodiment, the pharmacologic objective of therapy is to maximize a time-above-threshold concentration for depleting DNMTI (>0.1-0.2 µM), while avoiding high peak levels (>0.5-I µM) that damage DNA. In another embodiment, the pharmacologic objective of therapy is to maximize time-above-threshold concentration for depleting DNMTI (0.005-0.1 µM), while avoiding high peak levels (>0.5-I µM) that damage DNA. In another embodiment, the pharmacologic objective of therapy is to maximize a duration of time within a desired concentration for depleting DNMTI (0.005-0.05 µM), while avoiding high peak levels (>0.5-I µM) that damage DNA.

In another embodiment, the DNMTI-depleting effect should be intermittent. As a result, cells are allowed to divide and exhibit new behaviors. Continuous exposure to decitabine may prevent cell division or even kill cells directly.

The currently known route of administration, regimens, and formulations of decitabine produce high peak levels of the drug, which can kill cells through anti-metabolite effects but produce very brief time-above-threshold concentration for depleting DNMTI. Thus, the currently known route of administration, regimens, and formulations of decitabine do not deplete DNMTI intermittently to allow cell division, but, rather, produce cytotoxic or cytostatic effects. The destruction of decitabine by the enzyme cytidine deaminase (CDA) produces an abbreviated half-life in vivo of <20 minutes (despite an in vitro half-life of 5-9 hours) (Liu, Z., et al. 2006 Rapid Common Mass Spectrum 20: 1117-1126). This drastic reduction in half-life is a significant barrier to effective in vivo translation of in vitro observations. Pharmacogenomic variation in CDA (Gilbert, J. A., et al. 2006 Clin Cancer Res 12, 1794-1803; Kirch, H. C., et al. 1998 Exp Hematol 26, 421-425; Yue, L., et al. 2003 Pharmacogenetics 13, 29-38) produces large inter-individual variation in pharmacokinetics (PK) and clinical effects. Currently, injections or infusions of decitabine must be administered in the clinic or hospital, severely limiting its use in sickle cell disease, where the goal is chronic disease modification for the lifetime of the patient. In addition, intestinal CDA-mediated destruction severely limits its oral bioavailability; while the in vitro half-life of decitabine is 5-9 hrs, it has an abbreviated half-life of <20 minutes in vivo because of CDA-mediated destruction) (Liu, Z., et al. 2006 Rapid Commun Mass Spectrom 20:1117-1126; Liu, Z., et al. 2007 Nucleic Acids Res 35:e31), impeding the proposed treatment paradigm of multi-year, chronic therapy to produce sustained life-long therapeutic benefits. Malignant cells can develop resistance by destroying decitabine with CDA (Ohta, T., et al. 2004 Oncol Rep 12:1115-1120; Hubeek, I., et al. 2005 Br J Cancer 93:1388-1394; Huang, Y., et al. 2004 Cancer Res 64:4294-4301), and may find sanctuary from decitabine therapeutic effects by residing in tissues with high levels of CDA.

For at least the above reasons, an oral route of administration of decitabine is contemplated herein. Such oral administration is considered herein to decrease peak levels and increase the time-above-threshold concentration for depleting DNMTI, to enable chronic, frequent but not daily (i.e., metronomic) therapy to sustain life-long therapeutic effects while allowing cell division and minimizing toxicity, and to enable wide-spread use of the drug across the globe. Additionally contemplated herein to address the limitations and issues iterated above is the combination of decitabine with tetrahydrouridine (THU) for oral administration.

THU inhibits CDA, exhibits a benign toxicity profile and a well-characterized PK, overcomes the intestinal and liver first-pass barriers to oral bioavailability of decitabine, and addresses pharmacogenomic variation in CDA, which produces large inter-individual variation in decitabine PK and therapeutic effects. THU can produce a more predictable effect of a decitabine dose from individual to individual, increase the time-above-threshold concentration of decitabine for depleting DNMTI, remove sanctuary sites for malignant cells from decitabine therapeutic effects, and directly address one mechanism of cancer cell resistance to the therapeutic effects of decitabine.

Accordingly, in one embodiment, a composition for oral administration comprises decitabine and THU. In one example, the composition for oral administration comprises about 10.0 to about 150 mg/m$^2$ decitabine and about 100 to about 500 mg/m$^2$ THU. In another example, the composition for oral administration comprises about 0.01 to about 9.9 mg/m$^2$ decitabine and about 100 to about 500 mg/m$^2$ THU. In another example, the composition for oral administration comprises about 0.1 to about 9.9 mg/m$^2$ decitabine and about 300 to about 600 mg/m$^2$ THU. In another example, the composition for oral administration comprises about 0.035 to about 5.9 mg/m$^2$ decitabine and about 300 to about 600 mg/m$^2$ THU. In another example, the composition for oral administration comprises about 1.25 to about 4.9 mg/m$^2$ decitabine and about 350 to about 450 mg/m$^2$ THU. In another example, the composition for oral administration comprises about 5.0 to about 9.9 mg/m$^2$ decitabine and about 350 to about 450 mg/m$^2$ THU. In yet another example, the composition for oral administration comprises about 3.0 to about 7.0 mg/m$^2$ decitabine and about 400 mg/m$^2$ THU. In another example, the composition for oral administration comprises about 4.0 to about 6.0 mg/m$^2$ decitabine and about 400 mg/m$^2$ THU. For example, the composition may comprise about 5.0 mg/m$^2$ decitabine and about 400 mg/m$^2$ THU.

In a particular embodiment, a composition for oral administration comprises about 1.25 to about 7.0 mg/m$^2$ decitabine and about 350 to about 450 mg/m$^2$ THU, and may be formulated and/or administered such that the THU is bioavailable for some length of time, such as 15-180 minutes, before the decitabine is bioavailable. Unexpectedly, as described further below, such compositions may provide improved concentration-time profiles for DNMT1 depletion with reduced cytotoxicity, resulting in safer and more efficacious DNMT1-targeted therapy. Surprisingly, in non-human primates, such compositions were found to provide a sustained increase in Hbf, and a larger cumulative increase in HbF, than otherwise similar compositions comprising 10 mg/m² decitabine (both administered with 400 mg/m² THU, bioavailable 60 min before decitabine). This result indicates that a composition for oral administration comprising about 1.25 to about 7.0 mg/m² decitabine and about 350 to about 450 mg/m² THU, made bioavailable for some time before the decitabine, may offer unexpected advantages in the treatment of blood disorders and malignancies as described herein. Likewise, such compositions for oral administration may provide an extended time above minimum decitabine concentrations required for S-phase specific depletion of DNMT1, while avoiding undesirable higher peak concentrations that cause DNA damage and cytotoxicity. Such compositions for oral administration may be administered to a subject 1, 2, or 3 days a week on non-consecutive days over multiple weeks to provide a safer, more efficacious, and more convenient method of treatment.

Compositions for oral administration may be formulated in various dosages to treat subjects of varying sizes/weight. For example, the composition for oral administration can comprise 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, or 9.9 mg/m² decitabine and 300, 325, 350, 375, 400, 425, 450, 475, 500, 525, 550, 575, 600, 625, 650, 675, 700, 725, 750, 775, or 800 mg/m² THU.

In another embodiment, the composition is for treating a blood disorder in a subject, such as a human subject. In yet another embodiment, the blood disorder is a hemoglobinopathy or a thalassemia. For example, the hemoglobinopathy may be sickle cell disease.

In another embodiment, the composition is for treating hematological or solid malignancies, such as cancers affecting the blood, bone marrow, and lymph nodes, including leukemia, lymphoma, and multiple myeloma, as well as related disorders like myelodysplastic syndrome, myeloproliferative disease, myelofibrosis, amyloid disorders, anemia associated with malignancy, anemia associated with inflammation including rheumatoid arthritis and inflammatory bowel diseases, anemia of chronic renal failure, anemia associated with chronic infections such as HIV or hepatitis, anemia due to thrombocytopenia associated with malignancy, idiopathic thrombocytopenia purpura and viral diseases including virally-related malignancies. Examples of virally-related malignancies include EBV malignancies, including, without limitation, Burkitt's lymphoma, lymphomas associated with immunosuppression, other non-Hodgkin's lymphomas, Hodgkin's disease, nasopharyngeal carcinoma, gastric adenocarcinoma, lymphoepithelioma-like carcinomas, and immunodeficiency-related leiomyosarcoma.

In another embodiment, the composition is for treating cancers that affect other tissues, such as cancers affecting the brain, head, neck, thyroid, bones, muscle, lung, esophagus, stomach, intestine, breasts, prostate, testes, ovaries, uterus, vagina, and skin.

In another embodiment, a composition for oral administration comprises THU and decitabine combined in a single capsule or tablet. In some examples, a composition for oral administration may comprise about 100 to 1000 mg THU and about 1 to 200 mg decitabine. Some compositions for oral administration may comprise about 400 to 1000 mg THU and about 1 to 15 mg decitabine. Other compositions for oral administration may comprise 15 to 200 mg decitabine and 400 to 1000 mg THU. Still other compositions for oral administration may comprise about 5 to 10 mg decitabine and 600 to 700 mg THU. In one example, a composition in the form of a capsule is contemplated comprising about 500 mg THU and about 100 mg decitabine. In another example, a composition in the form of a capsule is contemplated comprising about 650 mg THU and about 8 mg decitabine.

In some embodiments, a composition for oral administration maybe used to provide an oral regimen approximating 500 mg/m² THU combined with 10 to 100 mg/m² decitabine to produce a plasma concentration of decitabine of 0.1-0.5 µM in a subject, such as a human subject. In other embodiments, a composition for oral administration may be used to provide an oral regimen approximating 400 mg/m² THU combined with 1.5 to 7.0 mg/m² decitabine to produce a plasma concentration of decitabine of 0.005-0.05 µM in a subject, such as a human subject. In other embodiments, a composition for oral administration may be used to provide an oral regimen approximating 400 mg/m² THU combined with 4.0 to 6.0 mg/m² decitabine to produce a plasma concentration of decitabine of 0.005-0.05 µM in a subject, such as a human subject. In other embodiments, a composition for oral administration may be used to provide an oral regimen approximating 400 mg/m² THU combined with 0.5 to 9.9 mg/m² decitabine to produce a plasma concentration of decitabine of 0.005-0.1 µM in a subject, such as a human subject.

In yet another embodiment, a composition of the disclosure is administered once a week or once every two weeks to patients suffering from a blood disorder. In still another embodiment, a composition of the disclosure is administered between once to three times per week to patients with cancer. In yet another embodiment, a composition of the disclosure is administered between once every two weeks to as often as three times per week in patients at risk of developing hematological or solid malignancy, or at risk of having a relapse in a previous diagnosis of hematological or solid malignancy.

In yet another example, the composition for oral administration is in the form of a tablet, pill, capsule, lozenge, or other solid oral formulation that comprises about 0.25 to about 15 mg decitabine and about 500 to 1000 mg THU. In other examples, the composition for oral administration comprises about 0.5 to about 9.9 mg/m² decitabine and about 350 to about 450 mg/m² THU. A composition for oral administration may comprise, for example, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 mg decitabine and 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg THU.

In another embodiment, a composition for oral administration is provided in the form of a capsule, comprising THU and decitabine, wherein the THU is released more quickly than the decitabine. For example, the THU might be subject to a faster dissolution rate, or the THU might be located at the surface of the capsule, while the decitabine is located inside the capsule. In one embodiment of such a composition, the THU is bio-available about 15 to about 180 minutes before the decitabine, in another, about 30 to about 90 minutes before the decitabine, in another, about 60 minutes before the decitabine. The THU may also be administered separately, in succession (with THU first, then decitabine).

In another embodiment, the composition is stored with a desiccant. This could serve to extend the shelf-life of the composition and facilitate its distribution and use on a global scale.

In another embodiment, the disclosure provides a method for treating a blood disorder in a subject comprising administration of a composition comprising decitabine and tetrahydrouridine as described above. In yet another embodiment, the disclosure provides a method for treating a cancer in a subject comprising administration of a composition comprising decitabine and tetrahydrouridine as described above. In a further embodiment, the administration occurs 1-3 times per week. For example, a composition comprising decitabine and tetrahydrouridine may be administered orally to a subject twice per week or three times per week.

In one aspect, the disclosure provides a composition for oral administration comprising about 10 to about 150 mg/m$^2$ decitabine and about 100 to about 500 mg/m$^2$ tetrahydrouridine and a pharmaceutically acceptable excipient. In another aspect, the disclosure provides a composition for oral administration comprising about 1 to about 9.9 mg/m$^2$ decitabine and about 100 to about 500 mg/m$^2$ tetrahydrouridine and a pharmaceutically acceptable excipient. In another aspect, the disclosure provides a composition for oral administration comprising about 100 mg decitabine and about 500 mg tetrahydrouridine and a pharmaceutically acceptable excipient. In another aspect, the disclosure provides a composition for oral administration comprising about 8 mg decitabine and about 650 mg tetrahydrouridine and a pharmaceutically acceptable excipient.

In one embodiment, a composition of the disclosure is for treating a blood disorder in a subject. In yet another embodiment, the blood disorder is a hemoglobinopathy or a thalassemia. In additional embodiments, the hemoglobinopathy is a sickle cell disease, and the thalassemia is a beta thalassemia (for example, hemoglobin E beta thalassemia).

In another embodiment, a composition of the disclosure is for treating a hematological or solid malignancy in a subject. In yet another embodiment, the malignancy is selected from the group consisting of leukemia, lymphoma, multiple myeloma, cancer of the brain, cancer of the head, cancer of the neck, cancer of the mouth, cancer of the pharynx, cancer of the esophagus, cancer of the stomach, cancer of the intestine, cancer of the thyroid, cancer of the lungs, cancer of the mediastinum, cancer of the thymus, cancer of the mesothelium, cancer of the peritoneum, cancer of the bone, cancer of the muscle, cancer of the skin, cancer of the prostate, cancer of the breasts, cancer of the ovaries, cancer of the uterus, cancer of the vagina, and virally related malignancy. In an additional embodiment, the virally-related malignancy is an EBV malignancy.

In another embodiment of a composition, the tetrahydrouridine is bio-available about 15 to about 180 minutes before the decitabine. In another embodiment, the tetrahydrouridine is bio-available about 30 to about 60 minutes before the decitabine. In one embodiment, the THU and decitabine are administered concurrently. In another embodiment, the THU is administered first, and the decitabine is administered later.

In another aspect, the disclosure provides a composition for oral administration in the form of a capsule or tablet comprising decitabine and tetrahydrouridine and a pharmaceutically acceptable excipient, wherein the tetrahydrouridine is bio-available about 15 to about 180 minutes before the decitabine; or about 30 to about 60 minutes before the decitabine. In one embodiment, the tetrahydrouridine is located at the surface of the capsule or tablet, and the decitabine is located within the capsule or tablet. In yet another embodiment of the composition of the disclosure, the THU is administered first in a capsule or tablet, and the decitabine is administered later in a second capsule or tablet.

In another aspect, the disclosure provides a method for treating a blood disorder in a subject, comprising administering to the subject a composition as described herein. In one embodiment, the blood disorder is a hemoglobinopathy or a thalassemia. In another embodiment, the subject is provided an additional form of therapy.

In another aspect, the disclosure provides a method for treating a hematological or solid malignancy in a subject, comprising administering to the subject a composition as described herein. In one embodiment, the malignancy is selected from the group consisting of leukemia, lymphoma, multiple myeloma, cancer of the brain, cancer of the head, cancer of the neck, cancer of the mouth, cancer of the pharynx, cancer of the esophagus, cancer of the stomach, cancer of the intestine, cancer of the thyroid, cancer of the lungs, cancer of the mediastinum, cancer of the thymus, cancer of the mesothelium, cancer of the peritoneum, cancer of the bone, cancer of the muscle, cancer of the skin, cancer of the prostate, cancer of the breasts, cancer of the ovaries, cancer of the uterus, cancer of the vagina, and virally related malignancy. In another embodiment, the virally related malignancy is an EBV malignancy. In yet another embodiment, the subject is provided an additional form of therapy.

In another aspect, the disclosure provides a method for decreasing the inter-individual variation in decitabine pharmacokinetics and/or clinical effects in subjects, comprising administering to the subjects a composition as described herein.

In still another aspect, the disclosure provides a method for extending the time-above-threshold concentration for depleting DNMTI with decitabine in a subject and avoiding DNA-damaging high peak levels of decitabine, comprising administering to the subject a composition as described herein.

In one embodiment of a method, the subject is human. In another embodiment, the method further comprises obtaining the composition.

Other aspects are described in or are obvious from the following disclosure and are within the ambit of the invention.

BRIEF DESCRIPTION OF THE FIGURES

The following Detailed Description, given by way of Examples, but not intended to limit the invention to specific embodiments described, may be understood in conjunction with the accompanying figures, in which:

FIG. 9C lists, in table form, the WHO classification and cytogenic abnormalities for each of the samples.

FIG. 19A: DAC 0.005 µM depletes DNMT1 in normal hematopoietic precursors. FIG. 19B-C: DAC>0.5 µM was required to induce measurable DNA damage. FIG. 19D: DAC>0.5 µM was required to induce apoptosis. FIG. 19E: DAC up to 0.5 µM in combination with THU did not cause significant DNA damage.

FIG. 20A shows IV and oral administration in PA7472. FIG. 20B shows IV and oral administration in PA7482. FIG. 20C shows SC and oral administration in PA7254. FIG. 20D shows SC and oral administration in PA7258.

FIG. 21A-B). In these same baboons after a washout period, THU 400 mg/m$^2$ 60 minutes before DAC produced higher DAC concentrations than THU 400 mg/m$^2$ administered simultaneously or 30 minutes before DAC (FIG. 21A-B).

FIG. 22A shows DAC concentration-time profiles in 8 baboons administered oral DAC 200 mg/m$^2$ (10 mg/kg). FIG. 22B shows DAC concentration-time profiles in the same 8 baboons administered DAC at half the dose (100 mg/m$^2$ [5 mg/kg]) 60 minutes after THU 400 mg/m$^2$ (20 mg/kg; THU-DAC). FIG. 22C shows $AUC_{last}$ in 7 animals administered DAC alone versus the same 7 animals receiving DAC at half the dose after THU.

FIG. 24A shows platelet counts during drug administration. FIG. 24B shows absolute neutrophil counts during drug administration. FIG. 24C shows phospho-H2AX (γH2AX) labeling of BM cells 96 hours after THU-DAC administration in week 8 in baboon number PA7472. FIG. 24D shows HbF expression during treatment. FIG. 24E shows decrease in methylation of developmentally responsive CpG in the γ-globin gene (HBG) promoter after drug administration in baboon numbers PA7472 and PA7484.

FIG. 25A shows platelet counts in PA7484. FIG. 25B shows absolute neutrophil counts (ANC) in PA7484. FIG. 25C shows HbF % in PA7484. FIG. 25D shows platelet counts in PA7472. FIG. 25E shows ANC in PA7472. FIG. 25F shows HbF % in PA7472.

DETAILED DESCRIPTION

I. Definitions

Figures 1A, 1B:
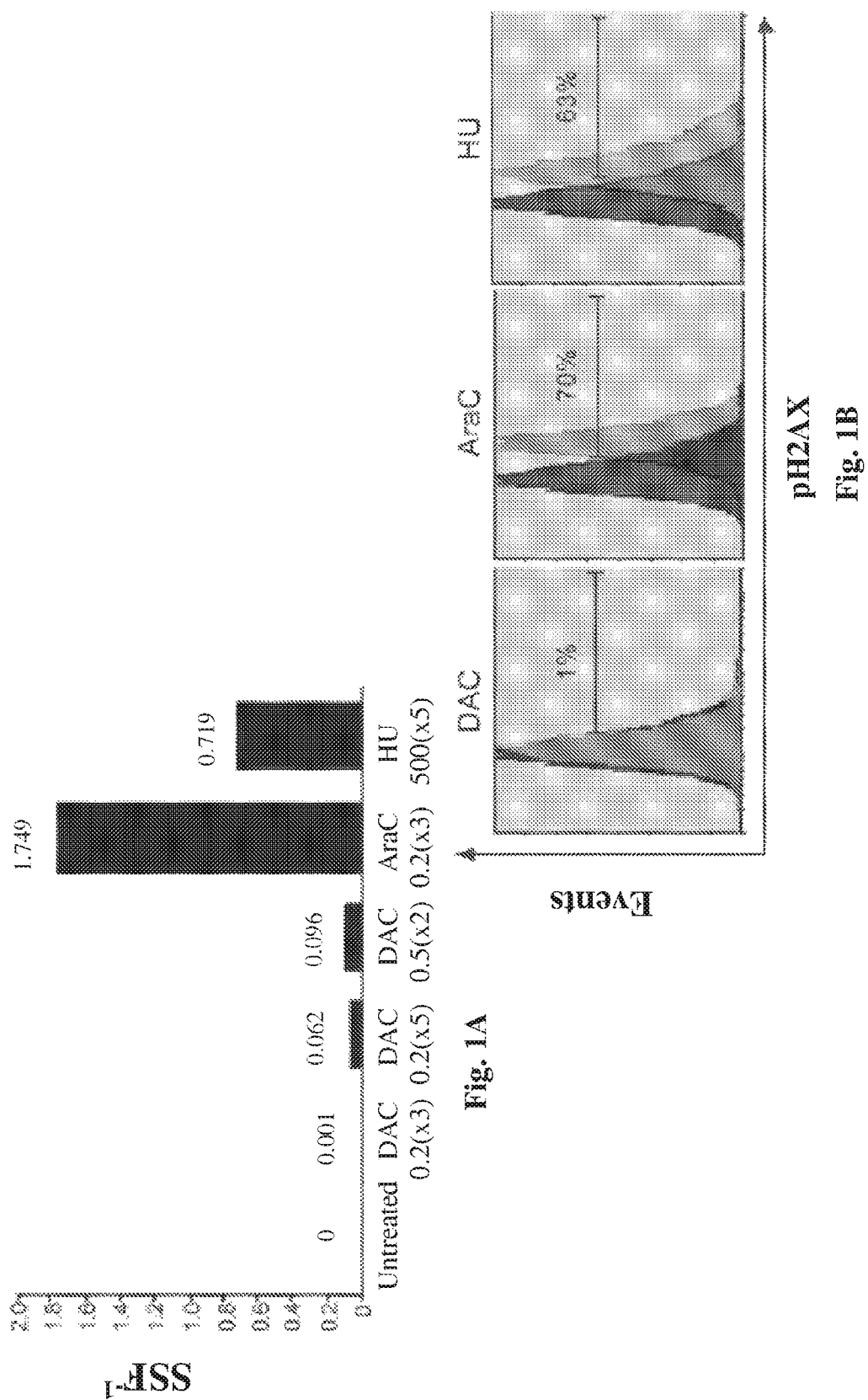
FIG. 1A quantifies, in bar graph form, DNA damage assessed in normal CD34+ hematopoietic cells subject to various decitabine concentrations.
FIG. 1B shows histograms depicting DNA damage assessed by phosphorylation of histone H2AX.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Hematological malignancies are a group of neoplasms that arise through malignant transformation of bone marrow derived cells. They can be subdivided into myeloid and lymphoid disorders and include, without limitation, acute lymphoblastic leukemia, chronic lymphoid leukemia, diffuse large B-cell lymphoma, follicular centre lymphoma, Hodgkins lymphoma, mantle cell lymphoma, marginal zone lymphoma, Waldenstrom's macroglobulinemia, myeloma, monoclonal gammopathy of uncertain significance, large granular lymphocyte syndrome, T-prolymphocytic syndrome, Sezary syndrome, lymphoma, angio-immunoblastic lymphoma, anaplastic large cell lymphoma, mycosis fungoides, lymphomatoid papulosis, small intestinal lymphoma, acute myeloid leukemia, myelodysplastic syndrome, myeloproliferative disorders, myelofibrosis, paroxysmal nocturnal hemoglobinuria, aplastic anemia, anemia associated with malignancy, thrombocytopenia associated with malignancy, virally-related malignancies, post-transplant lymphoproliferative syndrome, NK/T lymphoma, AIDS-related lymphoma, Burkitt's lymphoma, and non-Burkitt's small cell lymphoma. Chronic lymphocytic leukemia, non-Hodgkin lymphoma, and myeloid leukemia are particularly prevalent malignancies contemplated for treatment herein.

Solid tumor malignancies are a group of neoplasms that arise through the malignant transformation of cells in non-blood-related tissues. These include, without limitation, malignancies of the brain, head, neck, mouth, pharynx, esophagus, stomach, intestine, thyroid, lungs, mediastinum, thymus, mesothelium, peritoneum, bone, muscle, skin, prostate, breasts, ovaries, uterus, and vagina.

Hemoglobinopathies and thalassemias can both be characterized as "blood disorders" and are caused by abnormalities in the globin genes. Blood disorders include disorders that can be treated, prevented, or otherwise ameliorated by the administration of a compound of the disclosure. A blood disorder is any disorder of the blood and blood-forming organs. The term blood disorder includes nutritional anemias (e.g., iron deficiency anemia, sideropenic dysphasia, Plummer-Vinson syndrome, vitamin B 12 deficiency anemia, vitamin B 12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia (for example, hemoglobin E beta thalassemia), δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemoglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythroblastopenia), other aplastic anemias, such as constitutional aplastic anemia and fanconi anemia, acute post-hemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymophocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

The thalassemias are classified according to which chain of the hemoglobin molecule is affected. In α thalassemias, production of the α globin chain is affected, while in β thalassemia, production of the β globin chain is affected, β globin chains are encoded by a single gene on chromosome 11. Beta thalassemias are due to mutations in the HBB gene on chromosome 11.

The severity of the disease depends on the nature of the mutation. Mutations are characterized as (β° or β thalassemia major) if they prevent any formation of β chains (which is the most severe form of beta thalassemia); they are characterized as (β⁺ or β thalassemia intermedia) if they allow some β chain formation to occur. In either case, there is a relative excess of α chains, but these do not form tetramers: rather, they bind to the red blood cell membranes, producing membrane damage, and at high concentrations they form toxic aggregates.

The term "pharmaceutically acceptable excipient", as used herein, refers to carriers and vehicles that are compatible with the active ingredient (for example, a compound of the disclosure) of a pharmaceutical composition of the disclosure (and preferably capable of stabilizing it) and not deleterious to the subject to be treated. For example, solubilizing agents that form specific, more soluble complexes with the compounds of the disclosure can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the disclosure can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the disclosure.

The term "bio-available", as referred to herein, refers to when the active agent (tetrahydrouridine or decitabine) can be absorbed and used by the body. "Orally bio-available" indicates that the agent has been taken by mouth and can be absorbed and used by the body.

The term "subject" as used herein refers to a vertebrate, preferably a mammal, more preferably a primate, still more preferably a human. Mammals include, without limitation, humans, primates, wild animals, feral animals, farm animals, sports animals, and pets.

The term "obtaining" as in "obtaining the composition" is intended to include purchasing, synthesizing, or otherwise acquiring the composition (or agent(s) of the composition).

The terms "comprises", "comprising", are intended to have the broad meaning ascribed to them in U.S. Patent Law and can mean "includes", "including" and the like.

The disclosure can be understood more fully by reference to the following detailed description and illustrative examples, which are intended to exemplify non-limiting embodiments of the disclosure.

II Additional Embodiments

Pharmaceutical Compositions

In one embodiment, pharmaceutical compositions and dosage forms comprise about 10 to about 150 mg/m² decitabine and about 100 to about 500 mg/m² THU and a pharmaceutically acceptable excipient, in relative amounts and formulated in such a way that a given pharmaceutical composition or dosage form reactivates fetal hemoglobin (HbF) expression and/or expands normal hematopoietic stem cells and/or causes a shift to the erythropoietic lineage. In another embodiment, pharmaceutical compositions and dosage forms comprise about 1.0 to about 9.9 mg/m² decitabine and about 100 to about 500 mg/m² THU and a pharmaceutically acceptable excipient, in relative amounts and formulated in such a way that a given pharmaceutical composition or dosage form reactivates fetal hemoglobin (HbF) expression and/or expands normal hematopoietic stem cells and/or causes a shift to the erythropoietic lineage. In another embodiment, the pharmaceutical compositions and dosage forms comprise about 100 mg decitabine and about 500 mg THU and a pharmaceutically acceptable excipient. In another embodiment, the pharmaceutical compositions and dosage forms comprise about 5 to 10 mg decitabine and about 400 to 800 mg THU and a pharmaceutically acceptable excipient.

In another embodiment, pharmaceutical compositions and dosage forms comprise about 0.027 to 0.27 mg/kg decitabine and about 8 to about 14 mg/kg THU and a pharmaceutically acceptable excipient, in relative amounts and formulated in such a way that a given pharmaceutical composition or dosage producing in the subject a peak decitabine plasma concentration of <0.5 µM, with the decitabine plasma concentration maintained at or above 0.005 µM for at least 60 minutes. In some embodiments, the given pharmaceutical composition or dosage may produce in the subject a peak decitabine plasma concentration of <0.5 µM and maintain the decitabine plasma concentration at 0.005 µM to 0.1 µM for at least 60 minutes.

In another embodiment, the compositions are formulated in such a way that a given pharmaceutical composition or dosage form decreases the aberrant repression of differentiation-related genes in hematological or solid malignancies, thus reducing or inhibiting the growth of transformed (cancer) cells. In another embodiment, such pharmaceutical compositions and dosage forms comprise one or more additional active agents. For the treatment of hematological or solid malignancies, such additional active agents include chemotherapeutic agents known in the art.

The compositions may be administered orally ineffective dosages, depending upon the weight, body surface area, and condition of the subject being treated. Variations may occur depending upon the species of the subject being treated and its individual response to said medicament, as well as on the type of pharmaceutical formulation chosen and the time period and interval at which such administration is carried out.

In one embodiment, the pharmaceutical compositions may be administered alone or in combination with other known compositions for treating blood disorders in a subject, e.g., a mammal. Preferred mammals include cats, dogs, pigs, rats, mice, monkeys, chimpanzees, baboons and humans. In one embodiment, the subject is suffering from a blood disorder. In another embodiment, the subject is at risk of suffering from a blood disorder.

In another embodiment, the pharmaceutical compositions may be administered alone or in combination with other known compositions for treating hematological malignancies in a subject, e.g., a mammal. Preferred mammals include cats, dogs, pigs, rats, mice, monkeys, chimpanzees, baboons and humans. In one embodiment, the subject is suffering from a hematological malignancy. In another embodiment, the subject is at risk of suffering from a hematological malignancy.

The language "in combination with" a known composition is intended to include simultaneous administration of the composition of the present disclosure and the known composition, administration of the composition of the present disclosure first, followed by the known composition, and administration of the known composition first, followed by the composition of the present disclosure. Any of the compositions known in the art for treating blood disorders or hematological malignancies can be used in the methods of the invention.

The administration of the compositions of the disclosure maybe carried out in single or multiple doses. For example, the novel compositions of this disclosure can be administered advantageously in a wide variety of different dosage forms, i.e., they may be combined with various pharmaceutically acceptable inert carriers in the form of tablets, dragees, capsules, lozenges, troches, hard candies, aqueous suspensions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this disclosure are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

Sustained release compositions can be formulated including those wherein the active component is derivatized with differentially degradable coatings, e.g., by microencapsulation, multiple coatings, etc. In one embodiment of such a composition of the disclosure, the THU is bio-available about 15 to about 180 minutes before the decitabine. In another embodiment, the THU is bio-available about 30 to about 60 minutes before the decitabine.

It will be appreciated that the actual preferred amounts of active compounds used in a given therapy will vary according to the particular compositions formulated. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of the compounds of the disclosure generally to ensure their efficacy under normal use circumstances. Especially when employed for therapeutic treatment of humans and animals in vivo, the practitioner should take all sensible precautions to avoid conventionally known contradictions and toxic effects.

The composition, shape, and type of dosage forms of the disclosure will typically vary depending on their use. This aspect of the disclosure will be readily apparent to those skilled in the art. See, e.g., Remington's Pharmaceutical Sciences (1990) 18th ed., Mack Publishing, Eastern Pa.

The invention further encompasses pharmaceutical compositions and dosage forms that comprise one or more compounds that reduce the rate by which the compound of the disclosure will decompose. Such compounds, which are referred to herein as "stabilizer" include, but are not limited to, antioxidants such as ascorbic acid, pH buffers, or salt buffers.

The interrelationship of dosages for animals and humans (based on milligrams per meter squared of body surface) is described in Freireich, et al. 1966 Cancer Chemother Rep 50: 219. Body surface area may be approximately determined from height and weight of the patient. See, e.g., Scientific Tables, Geigy Pharmaceuticals, Ardley, N.Y., 1970, 537.

Methods of Treatment

In one embodiment, a composition of the disclosure is administered to a patient in need of treatment of a blood disorder. In another embodiment, a composition of the disclosure is administered to a patient in need of treatment of a hematological or solid malignancy. Other conditions, diseases and disorders that would benefit from such uses are known to those of skill in the art.

Responsiveness of the disease to compositions of the disclosure can be measured directly by comparison against conventional drugs (for example, for hematological or solid malignancies, chemotherapeutics; for certain blood disorders, hydroxyurea, histone deacetylase inhibitors, or erythropoietin), or can be inferred based on an understanding of disease etiology and progression. For example, there are a number of HbF expression assay systems that are widely accepted in the art as predictive of in vivo effects. Thus, the showing that a compound of this disclosure induces HbF expression in these assays is evidence of the clinical utility of these for treating a hemoglobinopathy and/or a thalassemia, i.e., a blood disorder.

In one embodiment, "treatment" or "treating" refers to an amelioration of a hemoglobinopathy and/or a thalassemia, i.e., a blood disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a hemoglobinopathy and/or a thalassemia, i.e., a blood disorder, either physically, e.g., stabilization of a discernible symptom, physiologically, e.g., stabilization of a physical parameter, or both. In yet another embodiment, "treatment" or "treating" refers to delaying the onset of a hemoglobinopathy and/or a thalassemia, i.e., a blood disorder, or symptoms thereof.

In another embodiment, "treatment" or "treating" refers to an amelioration of a hematological or solid malignancy or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of cancer, either physically, e.g., stabilization of a discernible symptom, physiologically, e.g., stabilization of a physical parameter, or both. In yet another embodiment, "treatment" or "treating" refers to delaying the onset of a hematological or solid malignancy or symptoms thereof.

The compositions of the disclosure can be assayed in vitro or in vivo, for the desired therapeutic or prophylactic activity, prior to use in humans. For example, animal model systems can be used to demonstrate the safety and efficacy of compounds of this disclosure.

Without wishing to be bound by theory, it is believed that the compositions of this disclosure induce gene expression, for example, fetal hemoglobin expression and, as a result, may be used to treat or prevent a hemoglobinopathy and/or a thalassemia, i.e., a blood disorder. Further without wishing to be bound by theory, it is believed that the compositions of this disclosure bind to and deplete DNA methyl transferase (specifically, DNMTI), decreasing repression or aberrant repression of genes that could have therapeutic effects if they were expressed, and, as a result, may be used to treat or prevent hematological or solid malignancies. It should be noted, however, that the compositions might act by a secondary or a different activity, such as, without limitation, stimulating hematopoiesis, erythropoiesis, and increasing self-renewal of normal stem cells.

The altered expression of genes could also increase recognition of malignant cells by cells of the immune system, whether that immune system is the patient's own or an allogeneic immune system reconstituted through allogeneic stem cell transplantation or infusion of donor lymphocytes.

Combination Therapy

The herein-described methods for treating a hemoglobinopathy and/or a thalassemia, i.e., a blood disorder, in a subject can further comprise administering to the subject being administered a composition of this disclosure, an effective amount of one or more other therapeutic agents. In one embodiment where another therapeutic agent is administered to a subject, the effective amount of the composition of the disclosure is less than its effective amount would be where the other therapeutic agent is not administered. In another embodiment, the effective amount of the other therapeutic agent is less than its effective amount would be where the composition of the disclosure is not administered.

The herein-described methods for treating a hematological or solid malignancy in a subject can further comprise administering to the subject being administered a composition of this disclosure, an effective amount of one or more other therapeutic agents. In one embodiment where another therapeutic agent is administered to a subject, the effective amount of the composition of the disclosure is less than its effective amount would be where the other therapeutic agent is not administered. In another embodiment, the effective amount of the other therapeutic agent is less than its effective amount would be where the composition of the disclosure is not administered.

In some aspects described herein, the method includes an additional therapeutic modality. For example, the additional therapeutic modality is radiation therapy or a cytotoxic chemotherapy agent, such as an anti-metabolite (e.g., 5-FU, with leucovorin), irinotecan, (or other topoisomerase inhibitor), doxorubicin, HDAC inhibitors, anti-viral agents, antiretroviral agents, or any combination all of these agents, including administration of all of these agents. Included with anti-viral agent treatment may be pre-treatment with an agent that induces the expression of viral thymidine kinase.

In additional aspects described herein, the methods can include monitoring the subject for the pharmacodynamic effect of therapy, e.g., for depletion of DNMTI in normal and malignant cells.

The methods can further include the step of monitoring the subject, e.g., for a reduction in one or more of: a reduction in tumor size; reduction in cancer markers, e.g., levels of cancer specific antigen; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the composition of the disclosure or for additional treatment with additional agents. Generally, a decrease in or stabilization of one or more of the parameters described above is indicative of the improved condition of the subject. Information about the monitoring can be recorded, e.g., in electronic or digital form.

The treatment methods disclosed herein can be used in combination with one or more additional treatment modalities, including, but not limited to: surgery; radiation therapy, and chemotherapy.

With reference to the methods disclosed herein, the term "combination" refers to the use of one or more additional agents or therapies to treat the same patient, wherein the use or action of the agents or therapies overlap in time. The additional agents or therapies can be administered at the same time as the composition of the disclosure is administered, or sequentially in any order. Sequential administrations are administrations that are given at different times. The time between administration of the one agent and another agent can be minutes, hours, days, or weeks.

The additional agent or therapy can also be another anti-cancer agent or therapy. Non-limiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anticancer agents are provided in detail as follows: antitubulin/antimicrotubule, e.g., paclitaxel, vincristine, vinblastine, vindesine, vinorelbin, taxotere; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU (Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon;

apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

Histone deacetylase inhibitors (HDAC inhibitors), a class of compounds that interfere with the function of histone deacetylase, are likewise contemplated as an additional agent for combination therapy. HDAC inhibitors include, without limitation, hyroxamic acids (for example, Trichostatin A), cyclic tetrapeptides (for example, trapoxin B), depsipeptides (for example, romidepsin), benzamides, electrophilic ketones, aliphatic acid compounds (for example, phenylbutyrate, valproic acid), SAHA/Vorinostat, FK228, Belinostat/PXDIOI, Panobinostat, MS-275, LAQ824/LBH589, C1994, MGCD0103, nicotinamide, NAD derivatives, dihydrocoumarin, naphthopyranone, 2-hydroxynaphthaldehydes, dicarboxamide derivatives, pyridyl and pyrimidinyl derivatives, 4-carboxybenzylamino derivatives, fluorinated arylamide derivatives, stilbene-like compounds, 3-(4-amidopyrrol-2-ylmethlidene)-2-indolinone derivatives and phenoxazinone.

A combination therapy can include administering an agent that reduces the side effects of other therapies. The agent can be an agent that reduces the side effects of anticancer treatments. A combinational therapy can also include administering an agent that reduces the frequency of administration of other therapies. The agent can be an agent that decreases growth of tumor after the anti-cancer effects of other therapies have decreased.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation. For example, the compounds of the disclosure may be administered to the subject for treatment of a hemoglobinopathy and/or a thalassemia, i.e., a blood disorder, in combination with one or more cytokines. In one embodiment, the cytokine is selected from the group consisting of IL-3, GM-CSF, G-CSF, stem cell factor (SCF) and IL-6.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description and the examples that follow, one skilled in the art can easily ascertain the essential characteristics of the present invention, and without departing from the spirit and scope thereof, can make various changes and modifications of the invention to adapt it to various usages and conditions. For example, the compounds of the disclosure may be used as research tools (for example, to isolate new targets for performing drug discovery). The compounds may, for instance, be radiolabeled for imaging tissue or organs or be used to form bioconjugates for affinity assays. These and other uses and embodiments of the compounds and compositions of this disclosure will be apparent to those of ordinary skill in the art.

The disclosure also encompasses all possible permutations of the claim set, as if they were multiple dependent claims.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The description of the present disclosure has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

The invention is further defined by reference to the following examples describing in detail the preparation of compounds of, the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided for illustrative purposes only and are not intended to limit the scope of the invention.

Example 1. Decitabine can Deplete DNMTI in Normal Hematopoietic Stem and Progenitor Cells without Causing Measurable DNA Damage or Apoptosis Decitabine is shown herein to deplete DNMTI without causing measurable DNA damage. Decitabine at a concentration of 0.2-0.5 µM depletes DNMTI in normal hematopoietic precursor cells (data not shown). Normal CD34+ hematopoietic precursor cells were isolated from cord-blood. A Q-dot based immunofluorescence assay quantifies DNMTI depletion by various doses of decitabine. Q-dot conjugated 2° ab against anti-DNMTI 1° ab allows quantification of DNMTI depletion in normal human CD34+ hematopoietic cells exposed to various levels of decitabine. DNMTI was quantified in 500 cells for each treatment condition. DAPI was used to stain the nuclei Image-quant software is used to quantify the DNMTI by the Mean Intensity Fluorescence (MIF) variable. Decitabine levels were assessed in µM.

FIGS. IA and B) Decitabine at a concentration of 0.5 µM, added to normal hematopoietic stem and progenitor cells 3×/wk, does not cause measurable DNA damage. However, decitabine 1.0 µM causes measurable DNA damage. A) The normal CD34+ hematopoietic cells subject to the decitabine concentrations above were assessed for DNA damage by the Fast Micro-method for measuring DNA scission 24 hrs after DAC exposure (Riccardi, R., et al. 1982 Cancer Res 42:1736-1739). In contrast, equimolar doses of Ara-C (Ara-C 0.5 µM) and clinically relevant levels of hydroxyurea (HU 500 µM), cause significant DNA damage (decitabine dose 0.5 µM DI, 3, 5; Ara-C dose 0.5 µM D 1, 3, 5; hydroxyurea dose 500 µM DI-5). Measurement was performed on D6. B) DNA damage was also assessed by phosphorylation (γ) of histone H2AX, an early marker of DNA repair again demonstrating the above concentrations of Ara-C (Ara-C) and clinically relevant levels of HU cause significant DNA damage, but not equimolar amounts of decitabine.

Dark histogram=isotype control for flow-cytometricanalysis. Light histograms show the γH2AX staining for untreated control cells. Measurement was performed on D6.

Figure 1C:
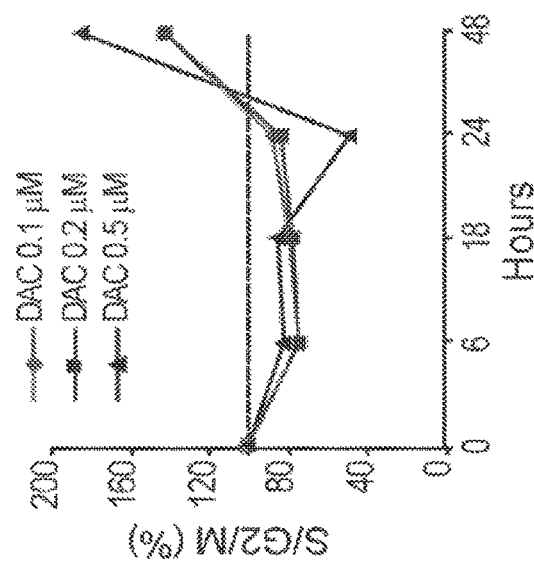
FIG. 1C graphically depicts S-phase/G2M with various concentrations of decitabine treatment.

FIG. 1C) DAC, at these non-DNA-damaging but DNMTI-depleting levels, produces transient cell-cycle arrest followed by rebound hyperproliferation. Cell cycle status was measured at the various timepoints by flow-cytometric assessment of propidium iodide staining. Decitabine treatment causes cytostasis with a rebound increase in S-phase/G2M that occurs approximately 48 h after drug exposure. Results are expressed as a percentage of untreated control.

The kinetics of DNMTI depletion and recovery in normal hematopoietic precursors exposed to a IX addition of DAC 0.5 µM. DNMTI was quantified with a Q dot-based assay. Nuclei were stained with DAPI. Decitabine was found to cause minimal or no evidence of apoptosis by flow-cytometric measurement of annexin V-FITC and 7AAD double staining (data not shown). Equimolar doses of Ara-C (Ara-C) and clinically relevant levels of HU (Kreis, W., et al. 1991 Leukemia 5:991-998) cause significant apoptosis and cell-death. Measurement was performed on D6.

Therefore, the cytotoxic effects of decitabine can be separated from its DNMTI depleting effects at concentrations between 0.2-0.5 µM. Therefore, for non-cytotoxic epigenetic therapy, the pharmacologic goal is to increase time above threshold concentration required to deplete DNMT (approximately 0.2 µM) while avoiding high peak levels that cause DNA damage (>0.5-1.0 µM).

Figure 2A:
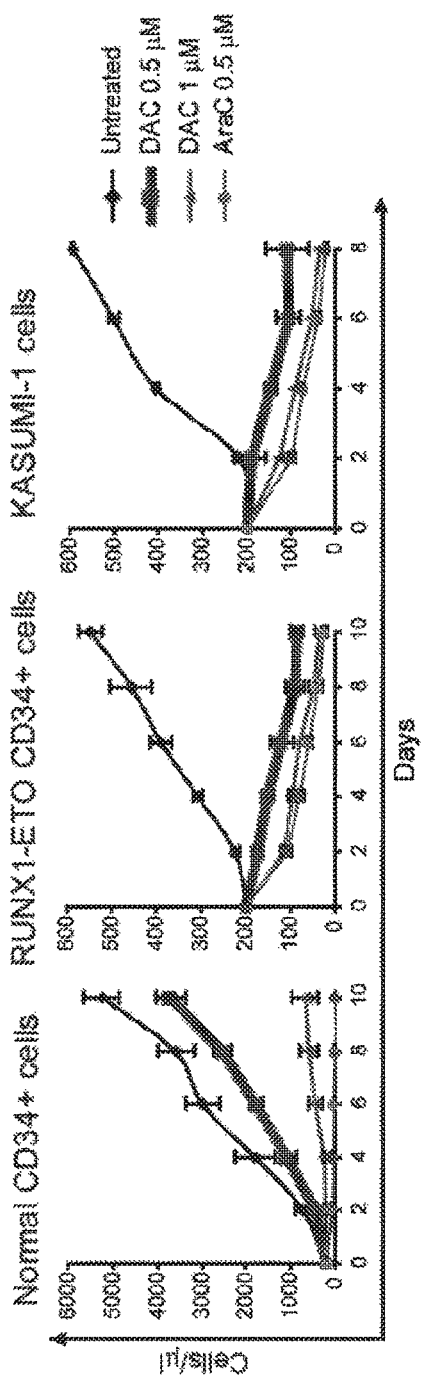
FIG. 2A graphically depicts cell counts for CD34+ cells, AML1-ETO CD34+ cells, and KASUMI-I cells exposed to Ara-C vs. two different doses of decitabine.
Figure 2B:
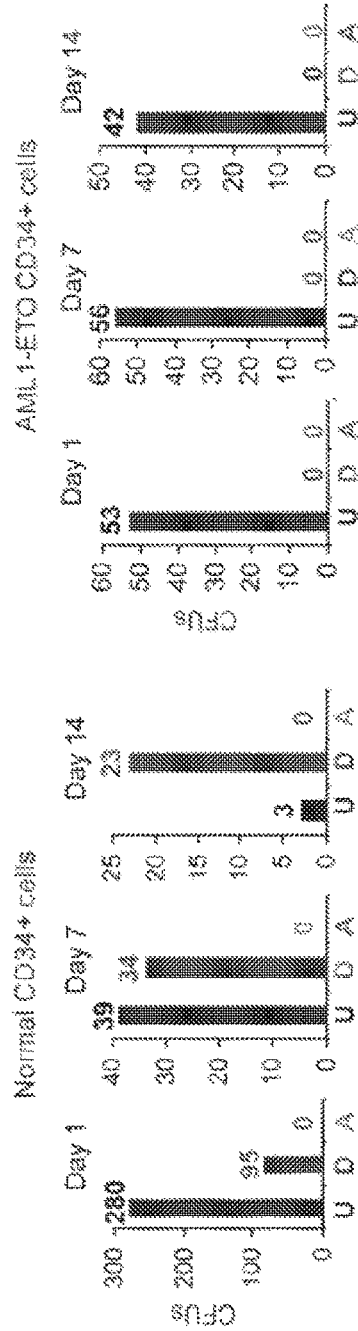
FIG. 2B shows, in bar graph form, colony-forming ability of normal CD34+ cells and AMLi-ETO CD34+ cells treated with decitabine vs. Ara-C over time.

Example 2. DNMTI-Depleting but Non-DNA Damaging, Doses of Decitabine have Opposite Effects on Normal Stem-Cells (HSC) Versus Leukemia Cells CD34 cells transduced with AMLI-ETO recapitulated some features of leukemia stem-cells (LSC) (impaired differentiation and increased self-renewal) and represented a first-hit or early model of leukemic transformation. The Kasumi-1 cell-line is derived from a patient with AMLI-ETO leukemia and represents a late-stage model of transformation and malignant evolution. Both of these models terminally differentiate with non-DNA-damaging but DNMTI-depleting doses of decitabine. FIG. 2A) Cell counts: an ideal therapeutic index was seen, with proliferation of normal cells while leukemia cells decline. In contrast, standard therapy (Ara-C), given at equimolar doses was more devastating to normal cells. Normal cells retained primitive morphology with decitabine treatment (data not shown). In contrast, CD34 AMLI-ETO and Kasumi-1 cells morphologically differentiated (decreased nuclear cytoplasmic ratio, nuclear segmentation or condensation, cytoplasmic granulation and vacuolation). FIG. 2B) Normal CD34+ cells treated with decitabine demonstrated increased self-renewal (Milhem, M., et al. 2004 Blood 103:4102-4110), therefore, decitabine treatment maintains colony-forming ability. In contrast, CD34 AMLI-ETO cells (leukemia cells) terminally differentiate with decitabine treatment and colony forming ability is abrogated (data not shown).

Figure 3B:
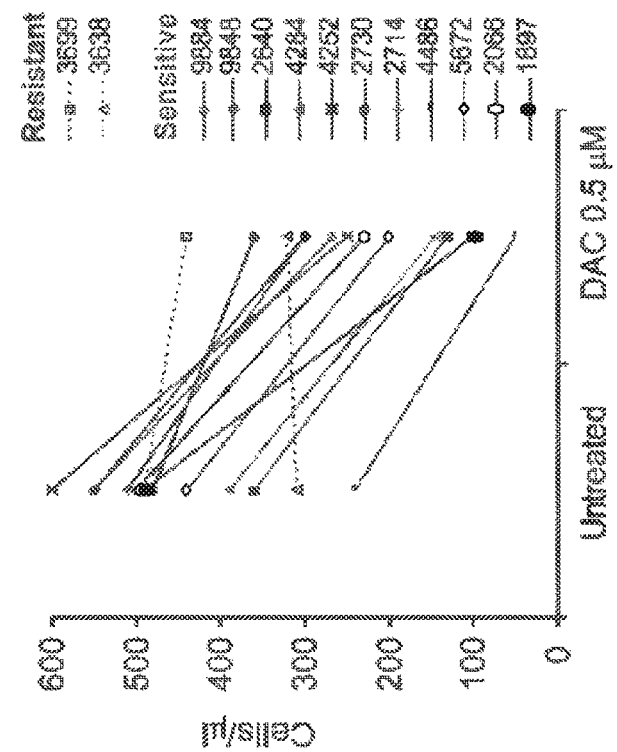
FIG. 3B graphically depicts the cell counts at day 7 in untreated vs. decitabine-treated cells.
Figure 3A:
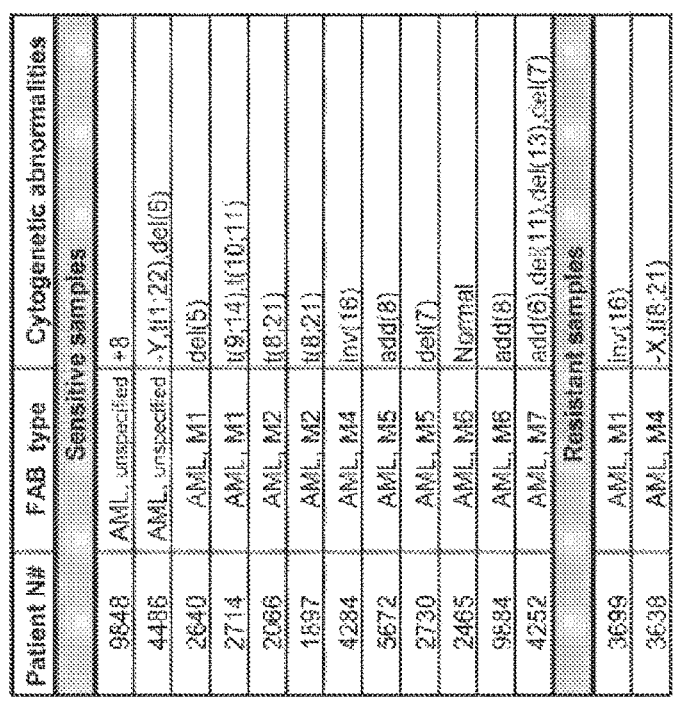
FIG. 3A shows a table providing FAB type and cytogenic abnormalities for samples from various patients.

Example 3. DNMTI Depletion without DNA Damage Produces Terminal Differentiation (not Immediate Apoptosis) of Primary Leukemia Cells from Patients Primary leukemia cells obtained from bone marrow or peripheral blood (with informed consent on an IRB approved protocol) were cultured in media supplemented with cytokines with or without decitabine 0.5 µM added 2×/week. These concentrations of decitabine did not cause DNA damage or immediate apoptosis (FIG. 3A). The samples were obtained from a spectrum of AML sub-types. FIG. 3B) Cell counts at D7 in untreated control versus decitabine-treated cells. Giemsa staining demonstrated terminal myelomonocytic differentiation of decitabine treated cells in 12 of 14 cases (data not shown). In cases of resistance, DNMTI expression in the cells was retained, indicating failure of decitabine activity, rather than resistance to the effects of DNMTI depletion (data not shown).

Decitabine 0.5 µM, concentrations that did not cause early apoptosis as measured by Annexin staining, terminally differentiated solid tumor cell-lines (renal cancer, small cell lung cancer, hepatocellular cancer, prostate cancer, bladder cancer), producing morphologic changes of differentiation (increased cell-size, decreased nuclear-cytoplasmic ratio).

Figure 4:
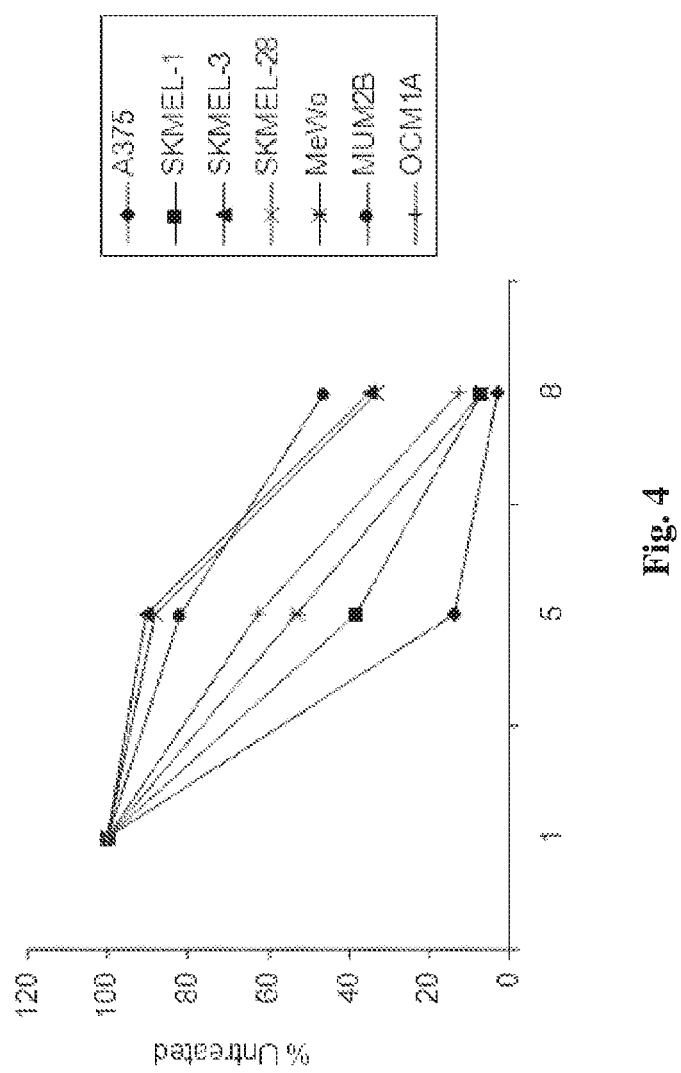
FIG. 4 graphically depicts cell counts in untreated vs. decitabine-treated cells at day 9.

Melanoma is a cancer that is resistant to conventional apoptosis-based therapy. Decitabine 0.5 µM induced changes of terminal differentiation in 7 melanoma cell lines. FIG. 4) Cell counts in control and decitabine treated cells at D9. Giemsa-stained control and treated cells at D8—morphologic changes indicated that decitabine treatment induced differentiation (data not shown).

Figure 5A:
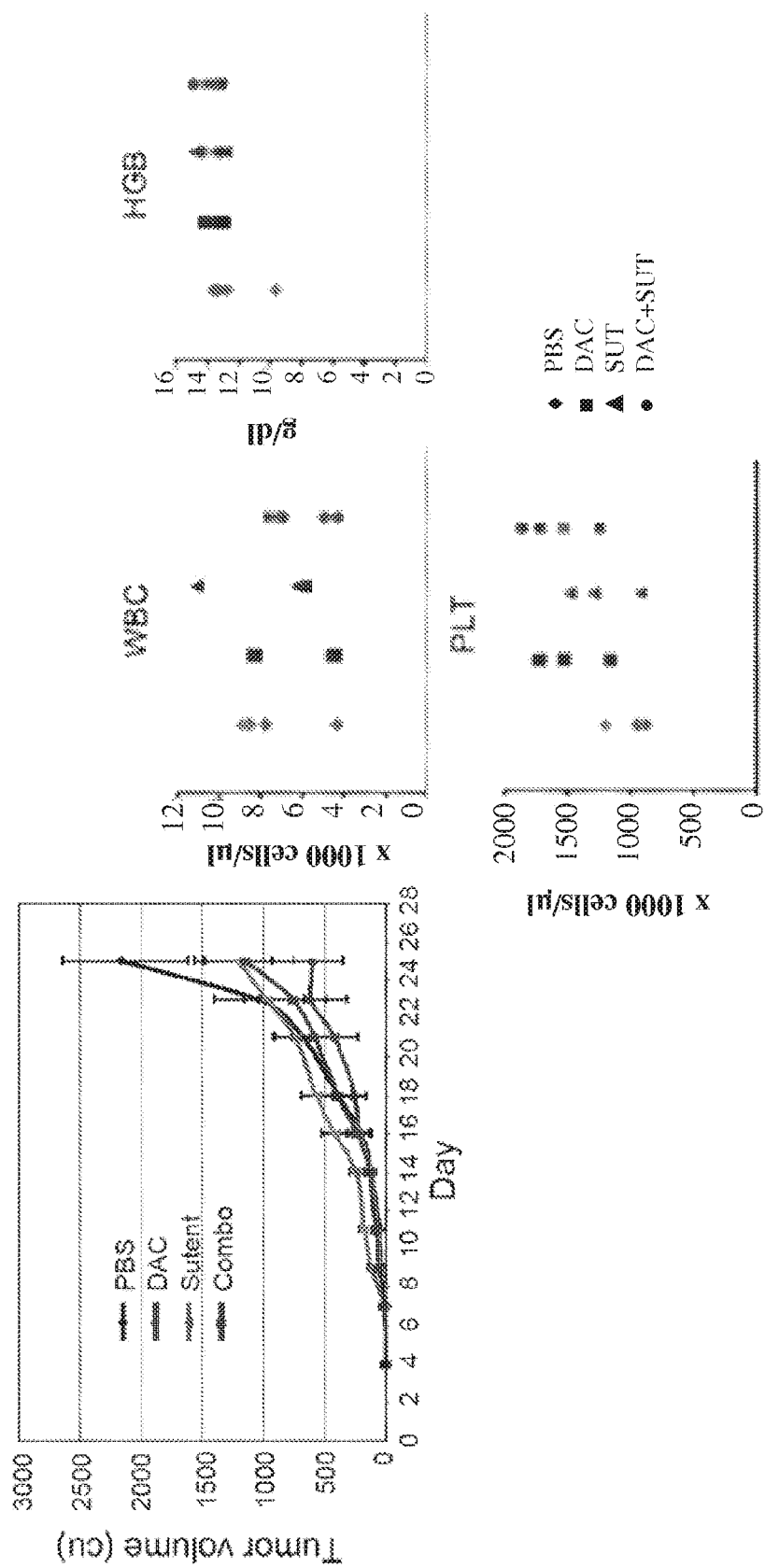
FIG. 5A graphically depicts tumor volume over time in mice treated with PBS (control) vs. decitabine vs. Sunitinib vs. a combination of decitabine and Sunitinib.
Figure 5B:
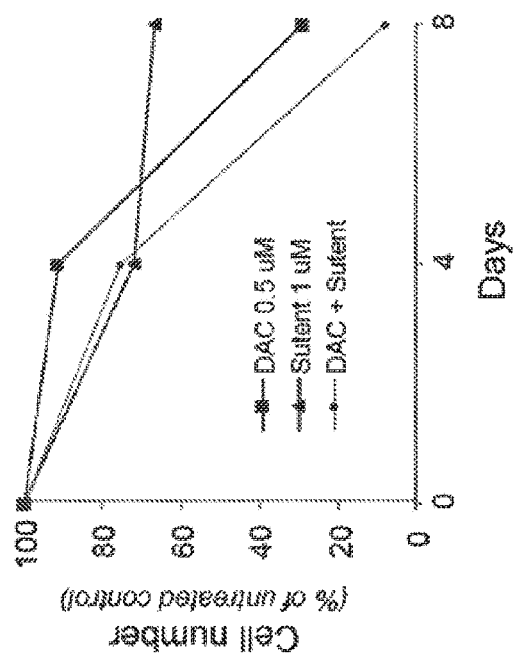
FIG. 5B graphically depicts cell number over time for the mice.

Example 4. A Differentiation Therapy Regimen of Decitabine is Effective and Very Well Tolerated in a Xeno-Transplant Model of Avastin-Resistant Renal Cancer In an effort to apply the proposed formulation and regimen to treat different cancer histologies, a renal cell cancer cell-line (Reno-1) was developed from a surgical sample of renal cancer and used in a xeno-transplantation experiment. In a xenograft model of resistant renal cancer, SQ decitabine given 3×/week at a dose of I mg/ni2 (starting on Day 9—tumor vol. 100) significantly decreased tumor volume without evidence of toxicity in the mice (no change in weight, appearance or blood counts). This tumor was relatively resistant to avastin and sunitinib, standard agents used to treat renal cancer. FIG. 5A) Decitabine (DAC) decreased tumor volume (p<0.001, t-test), compared to control (PBS) or Sunitinib. Sunitinib antagonized the effect of decitabine, presumably by cytostasis that decreased the S-phase dependent incorporation of decitabine into tumor. H&E staining of paraffin embedded sections demonstrated necrosis in the decitabine-treated samples (data not shown). The percentage of necrosis in each tissue section was evaluated in a blinded fashion. The PBS-treated animals (controls) had dense, healthy tissue which is poorly staining (grey tissue highlighted with white arrows). FIG. 5B) Paraffin-embedded sections do not lend themselves to analysis for cytological detail. Therefore, the morphology of Giemsa-stained Reno-1 cells cultured with decitabine was examined in vitro. Decitabine-treated cells increase in size and demonstrate prominent nuclear chromatin clumps.

Example 5. The PUER Model of Pu.1-Mediated Hematopoietic Differentiation Provides an Insight into the Mechanisms that Underlie the Opposite Effects of DNMTI Depletion on the Self-Renewal of Normal HSC Versus Leukemic Cells Terminal differentiation is critically dependent on lineage-determining transcription factors such as PU.1. PU.1, like other lineage-determining DNA binding factors, demonstrates both transcription repression and transcription-activating functions, determined by interactions with either corepressors versus coactivators. The murine PUER cell-line is derived from Pu.1 knock-out cells, which have been transduced with a retroviral vector which expresses Pu.1 fused to the estrogen-receptor. Addition of the estrogen agonist tamoxifen (OHT) to these cells causes Pu.1 to be functionally reintroduced into the cell through translocation into the nucleus, and triggers terminal differentiation.

Figure 6:
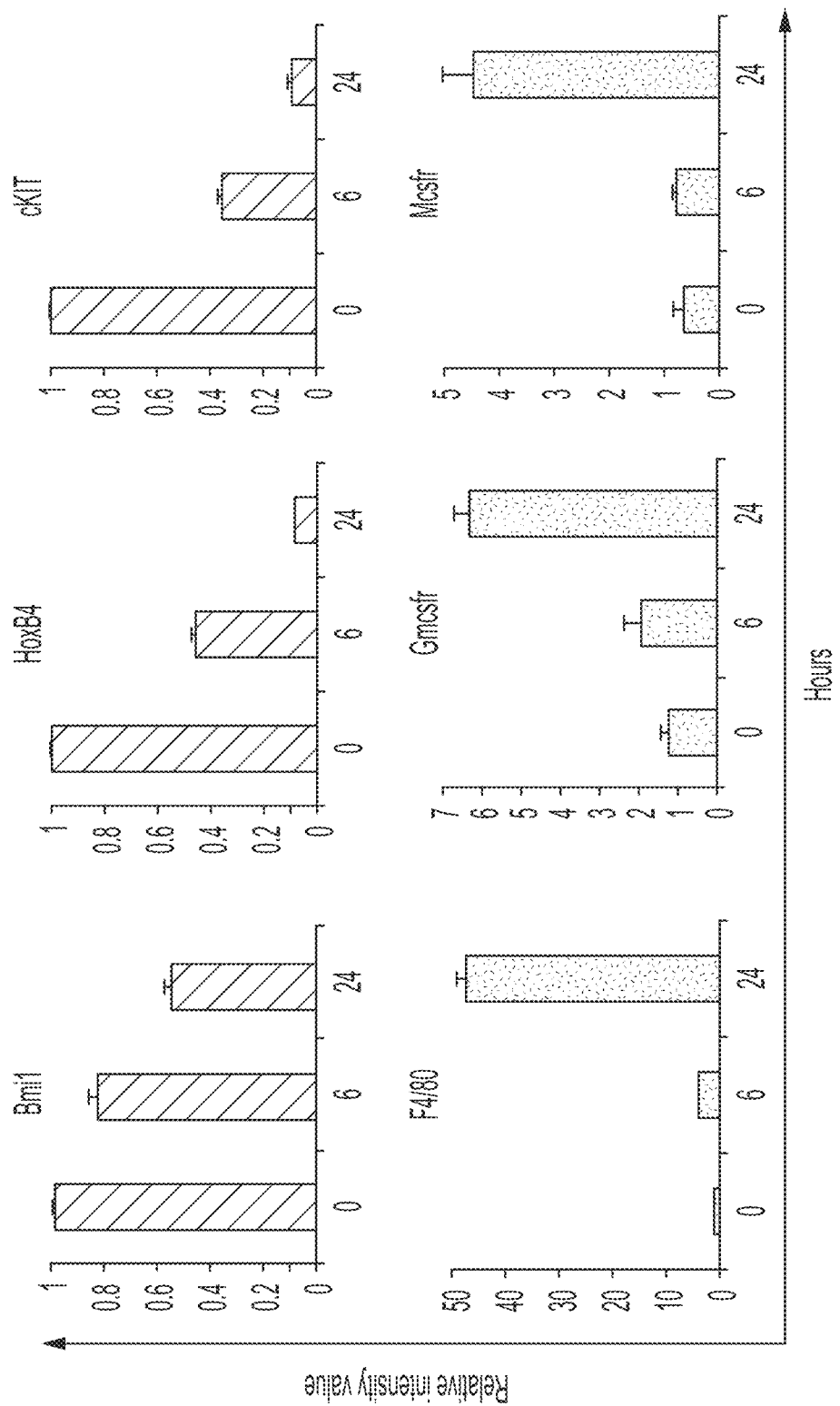
FIG. 6 shows, in bar graph form, the repression of HoxB4, Bmi-1, and cKIT and the activation of Mcsfr, Gmcsfr, and F4/80 over time in PUER cells.

FIG. 6) Pu.1 induced terminal differentiation involves orderly and sequential repression of genes associated with self-renewal (HoxB4, Bmi-1, c-Kit), followed by activation of genes associated with terminal differentiation (Mcsfr, Gmcsfr, F4/80) (latter data not shown).

Figure 7A:
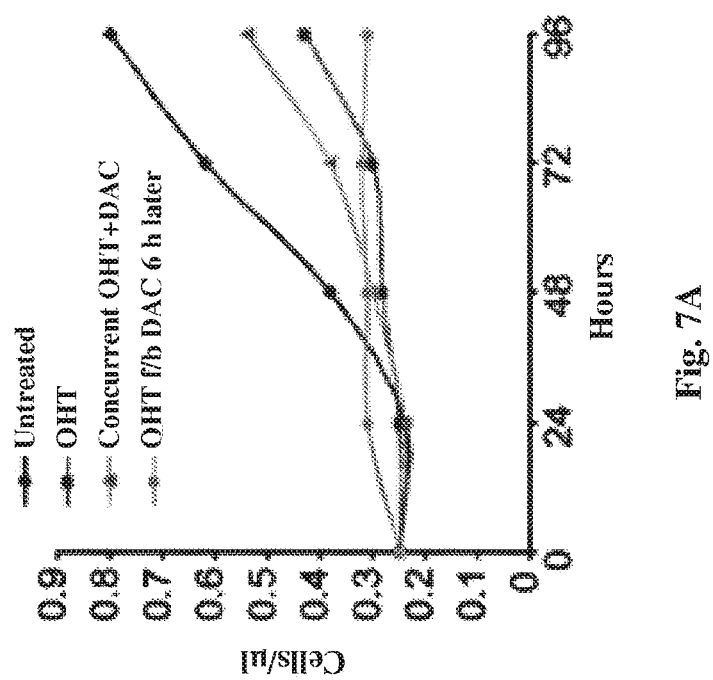
FIG. 7A graphically depicts cell proliferation over time of treatment with OHT vs. OHT+decitabine vs. OHT followed by decitabine.
Figure 7B:
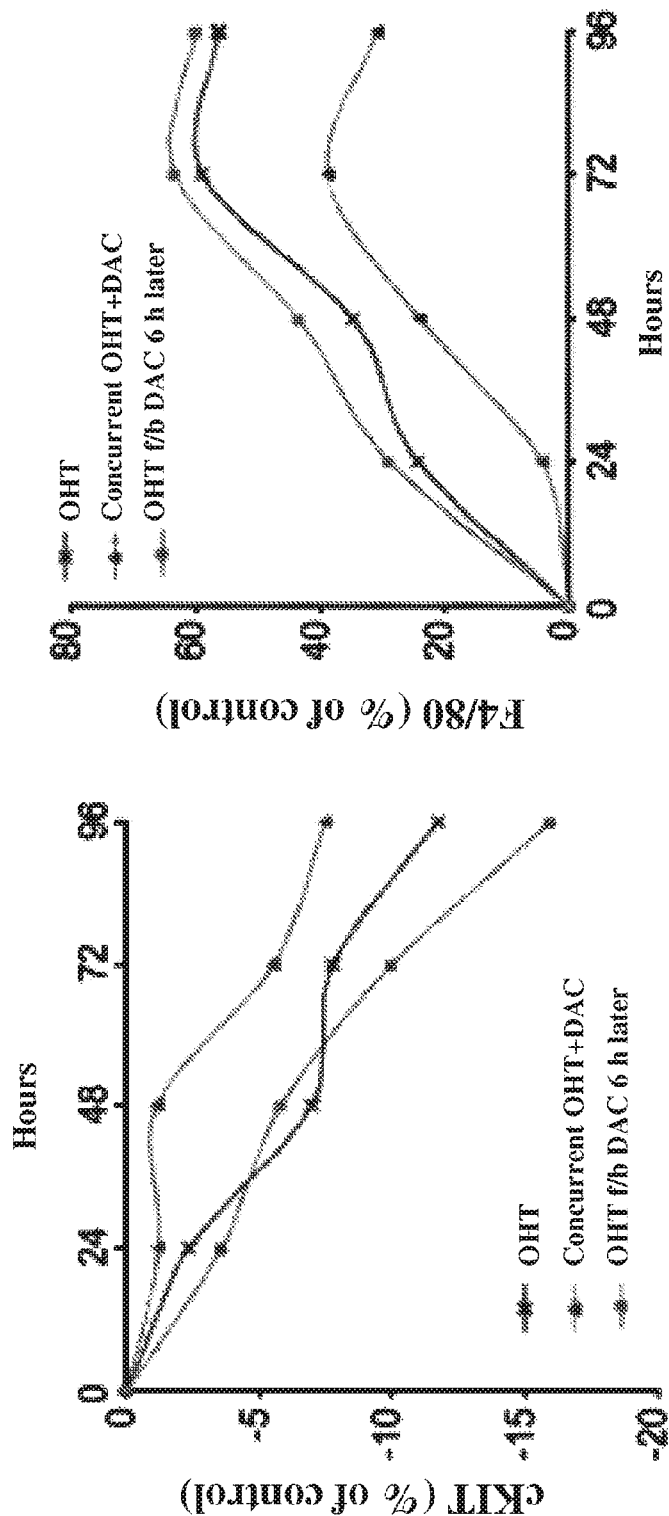
FIG. 7B graphically depicts macrophage differentiation (F4/80) and stem cells (c-KIT) over time of treatment with OHT vs. OHT+decitabine vs. OHT followed by decitabine.
Figure 7C:
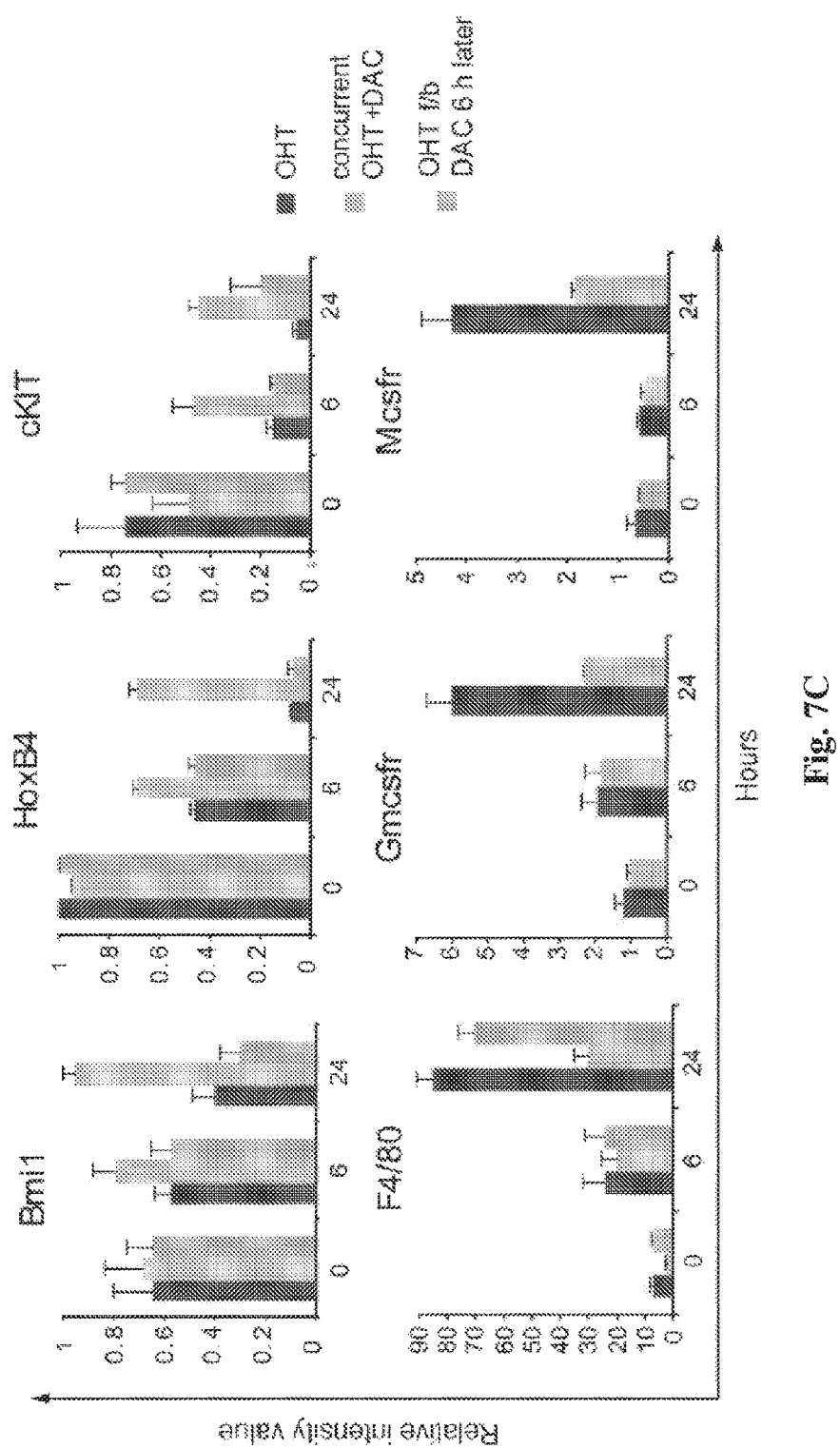
FIG. 7C shows, in bar graph form, Bmil, HoxB4, cKIT, F4/80, Gmcsfr, and Mcsfr over time of treatment with OHT vs. OHT+decitabine vs. OHT followed by decitabine.

Example 6. The Phenotypic Consequences of DNMTI Depletion Depend on the Differentiation Chronology of the Cell FIG. 7A) The effect of decitabine on proliferation of PUER is dependent on the timing of decitabine addition in relationship to Pu.1 activation (Pu.1 is functionally activated by adding OHT to the cells). Adding decitabine concurrent with Pu.1 activation impaired Pu.1-mediated terminal differentiation and preserved some cell proliferation. However, adding decitabine 6 h after Pu.1 activation did not. FIG. 7B) Concurrent decitabine and Pu.1 activation inhibited differentiation, but decitabine 6 hrs after Pu.1 activation did not. Flow cytometry was used to measure F4/80 as a marker of terminal macrophage differentiation and c-Kit as marker of stem-cells. Cell morphology was consistent with the flow-cytometry data (data not shown). FIG. 7C) Decitabine addition concurrent with Pu.1 activation prevented the first step in terminal differentiation of pro-self-renewal gene repression. However, decitabine addition after pro-self-renewal gene repression had occurred (6 hours after OHT) increased pro-differentiation gene expression.

Therefore, the phenotypic consequences of DNMTI depletion critically depend on the differentiation chronology of the cell. By preventing the first step in differentiation, which is repression of pro-self-renewal genes, decitabine can increase self-renewal even in a differentiation-promoting context. These findings are a reasonable explanation for our published observation that decitabine increases self-renewal of normal HSC (Milhem, et al. 2004 Blood 103 (11):4102-10). In contrast, increased differentiation in response to decitabine that is added after self-renewal genes have already been repressed, resembles the effect of decitabine on leukemia cells. The opposite effects of decitabine on HSC versus leukemia cells could be proposed to result because leukemia is arrested differentiation in progress, distinct from self-renewal of HSC.

Example 7. Molecular Events when a Leukemia First-Hit Event (Disruption of RunxI) Inhibits Pu.1 Mediated-Differentiation RunxI disruption, by congenital or acquired RunxI mutations and chromosome translocations, is one of the most frequent genetic events in myelodysplasia and leukemia.

Figure 8:
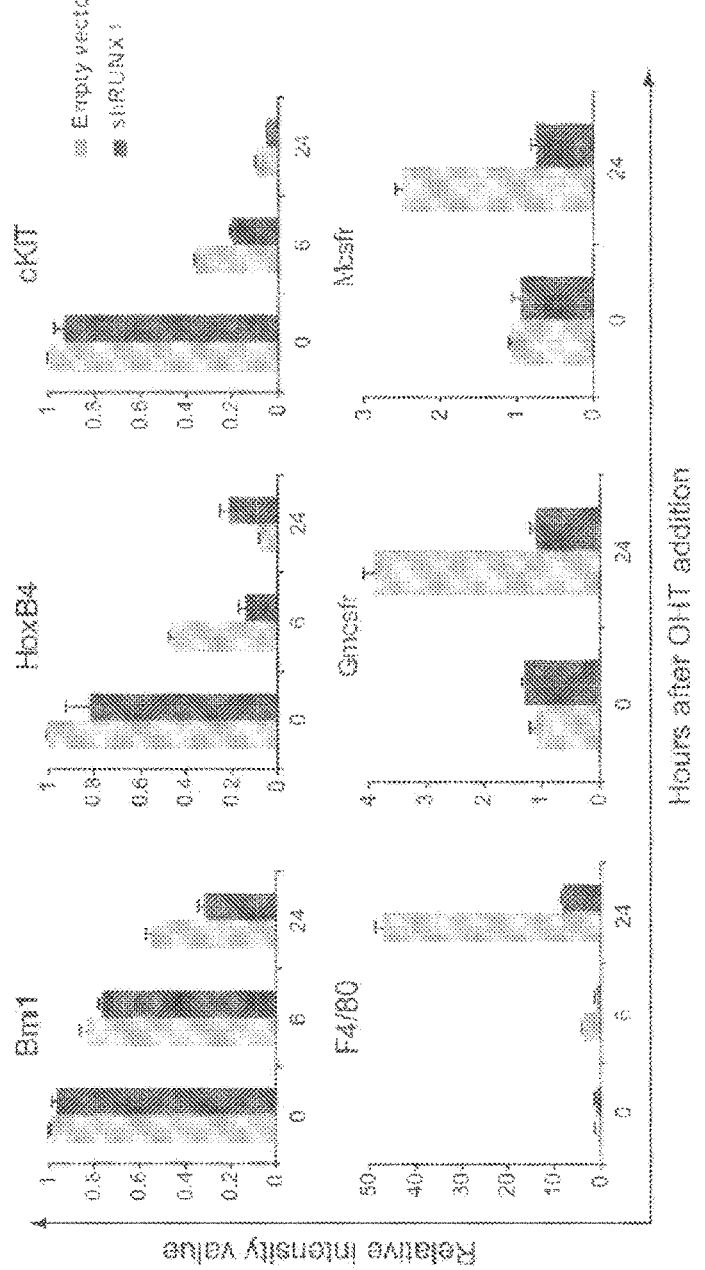
FIG. 8 shows, in bar graph form, Bmil, HoxB4, cKIT, F4/80, Gmcsfr, and Mcsfr over time in PUERshRunx1 cells.

Knock-down of RunxI expression in PUER cells did not prevent Pu.1-mediated repression of pro-self-renewal genes, but did inhibit Pu.1-mediated activation of pro-differentiation genes. Using lenti-viral shRNA delivery, RunxI expression was knocked down in PUER cells, and decreased RunxI expression was confirmed by Western blot (between 25-50% of control levels), in different PUERshRunxI clones (data not shown). PUERshRunxI cells did not terminally differentiate in response to Pu.1 activation (+OHT) (data not shown). FIG. 8) In PUERshRunxI cells, the first-step in Pu.1 mediated differentiation of pro-self renewal (Bmi-1, HoxB4, c-Kit) repression is intact. However, RunxI knock-down prevented the next chronological step in differentiation—activation of pro-differentiation genes (F4/80, mcsfr, gmcsfr).

Example 8. Leukemia Cells from Patients Conform to the Model

Figure 9A:
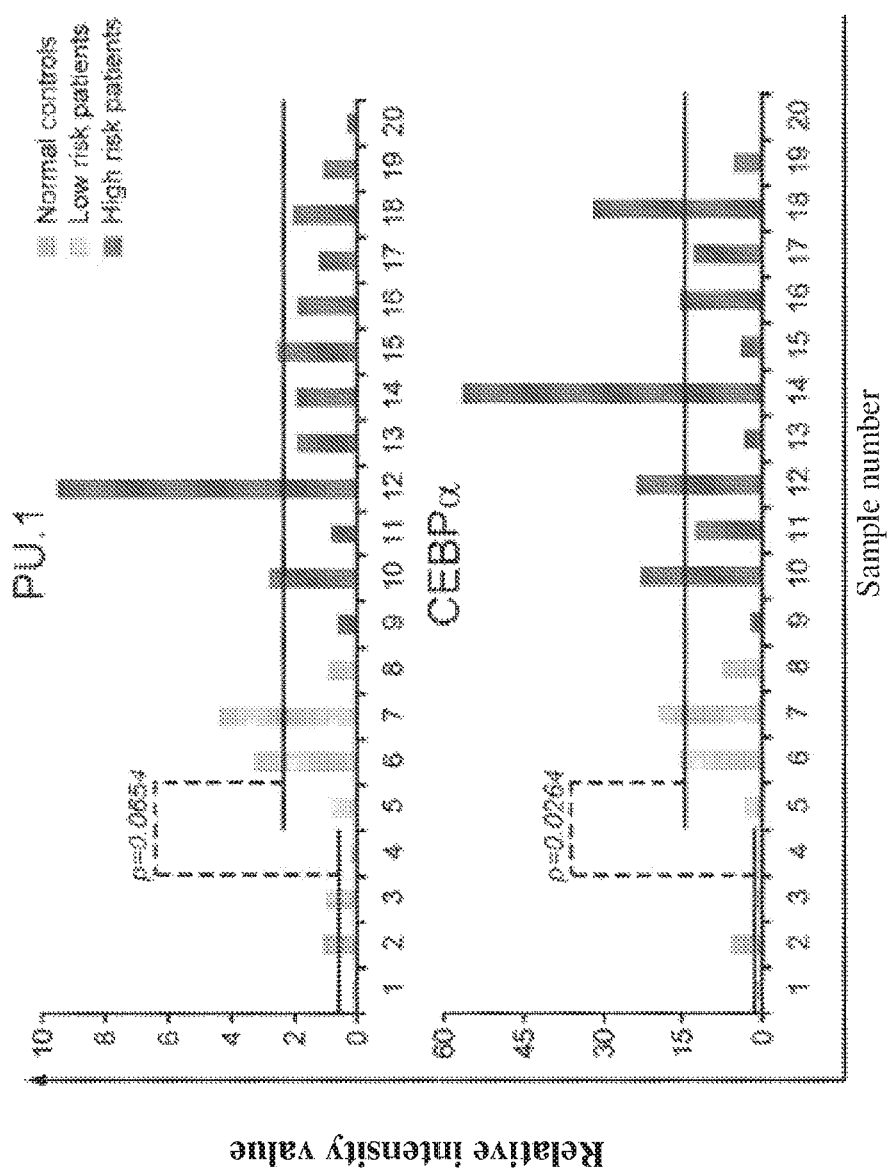
FIG. 9A shows, in bar graph form, PU.1 and CEBPα.
Figure 9B:
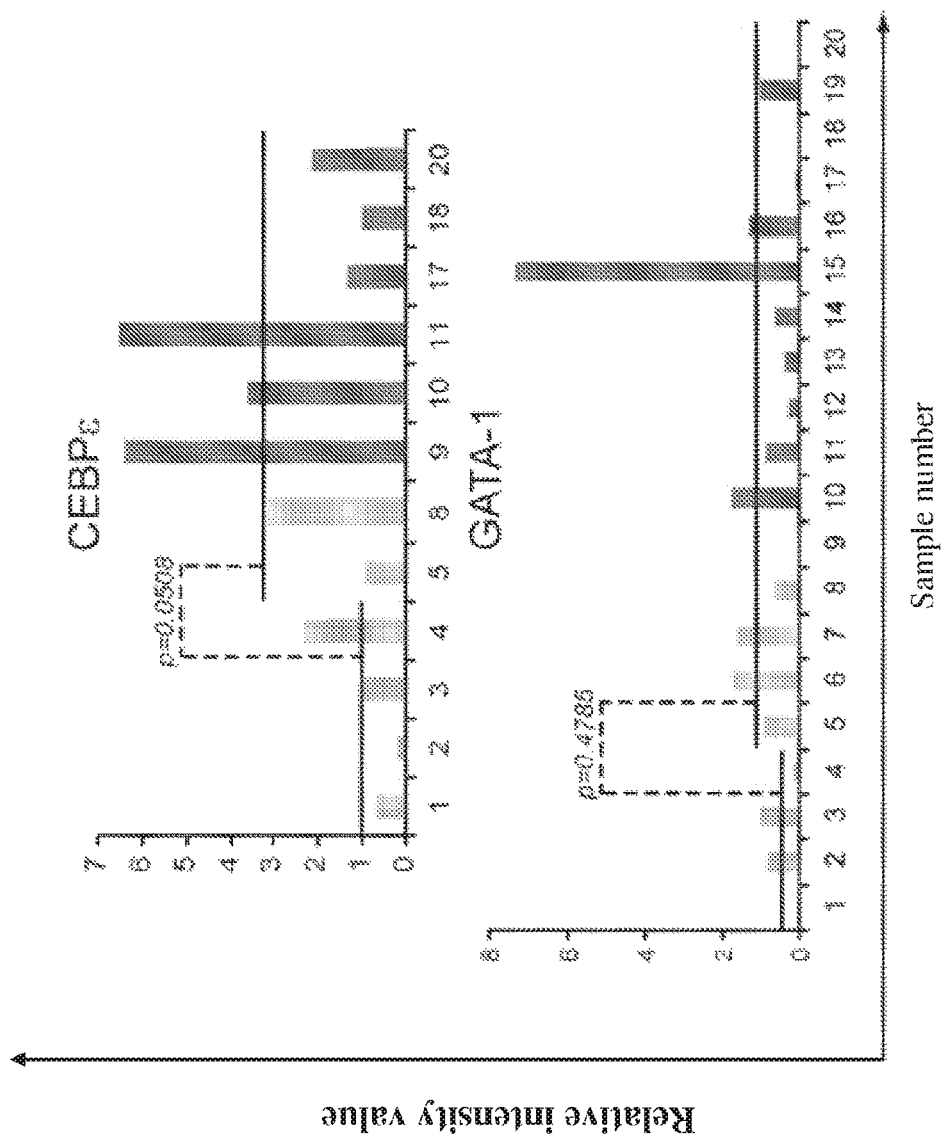
FIG. 9B shows, in bar graph form, CEB Pε and GATA-1 in various patient samples.

To examine the clinical relevance of the above findings regarding arrest in differentiation-transit, the levels of lineage-specifying factors were measured in primary leukemia cells from patients. Key lineage-specifying transcription factors in hematopoiesis include PU.1 (required for macrophage and B-lymphocyte production), CEBPα and CEB Pε required for neutrophil production and GATAI for erythroid production (Iwasaki, H., et al. 2006 Genes Dev 20:3010-3021). The levels of these factors increase during differentiation into the respective lineages. The expression levels of these factors were measured in bone marrow aspirate cells from normal donors, patients with low-risk myelodysplastic syndrome (MDS—a clonal hematologic disorder which often precedes AML) and patients with high-risk myelodysplastic syndrome and acute myeloid leukemia (high-risk disease). The low-risk MDS patient bone marrow aspirates contain abnormally differentiated and increased immature cells, but <5% myeloblasts. In the high-risk patient bone marrow aspirates, the average percentage of myeloblasts was 40%. The high-risk samples, although morphologically the least mature, had the highest levels of the myeloid lineage-specifying factors CEBPα, CEB Pε and PU.1 (FIGS. 9A-9B). GATA1 levels were not significantly increased in the disease samples compared to normal controls. The clinical annotation of the samples analyzed is shown (FIG. 9C).

Micro-array gene-expression data from 54 AML patients demonstrated a similar pattern of increased expression of lineage-specifying factors in AML samples compared to normal bone marrow cells (Yagi, T., et al. 2003 Blood 102:1849-1856).

Unlike DNA mutation or chromosome aberration, it is not immediately obvious that a difference in promoter CpG methylation between a malignant and a normal sample is abnormal, since promoter CpG methylation varies among different tissues and with stage of differentiation. Therefore, classifying promoter CpG sites by the methylation changes that occur during normal differentiation could improve interpretation of DNA methylation studies in cancer and leukemia. In particular, such classification could illuminate the role of differentiation in malignant cell-specific patterns of promoter CpG methylation.

To address this issue, a promoter CpG methylation microarray was used to classify CpG sites by hypo-methylation, hyper-methylation, or no significant methylation change during normal myeloid differentiation. This classification was applied to a study of promoter CpG methylation patterns in primary myelodysplastic syndrome (MDS) and acute myeloid leukemia (AML) cells. In primary MDS cells, methylation at differentiation responsive CpGs was the inverse of that in normal CD34+ hematopoietic stem and progenitor cells (HSPC), with hypo-methylation of CpG that are normally hyper-methylated in CD34+ HSPC and vice-versa. In high risk (>5% myeloblasts) MDS/AML samples, and AML cell lines including CD34+ AML cell lines, this pattern was further exaggerated. This difference between normal HSPC and MDS/AML cell epigenetics could contribute to contrasting differentiation fates in response to drugs that inhibit chromatin-modifying enzymes (FIG. 9D).

This observation provides insight into leukemogenesis and MDS/AML biology. Promoter CpG methylation reflects differentiation stage or context. The pattern of promoter CpG methylation in the MDS/AML cells is consistent with a differentiation context that is more advanced or committed than normal HSPC. This possibility is clarified by the high expression of the key lineage-specifying transcription factors PU.1 and CEBPα in MDS/AML cells compared to normal hematopoietic stem and progenitor cells. Therefore, the pattern of promoter CpG methylation suggests, and is likely one dimension of, a lineage-committed differentiation context of MDS/AML cells.

Figure 9D:
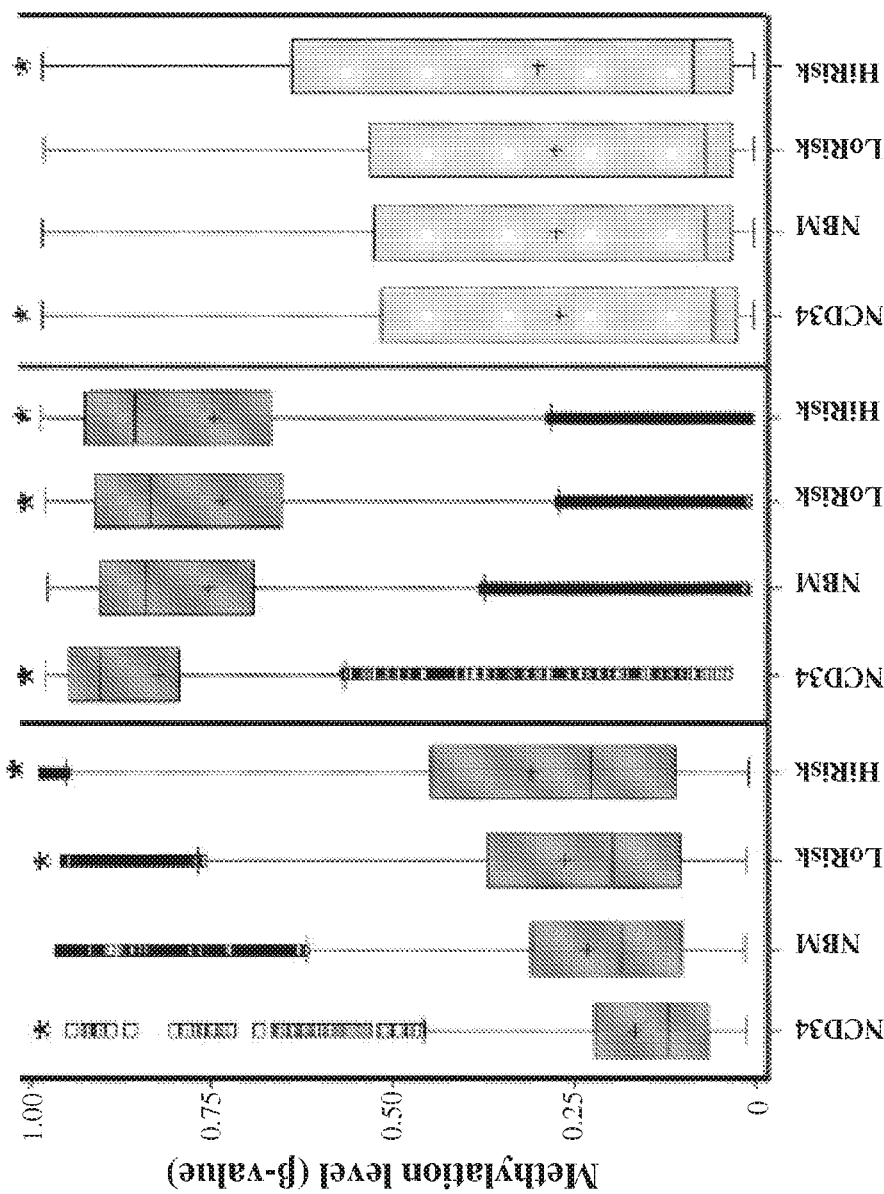
FIG. 9D shows, in bar graph form, precursor gene methylation and differentiation gene methylation for normal CD34+ cells, normal bone marrow cells, MDS cells, and AML cells.

FIGS. 9A-9D. Leukemia cells from patients are differentiation-impaired after lineage-commitment. FIGS. 9A-9B) High risk MDS and AML cells express high levels of lineage-specifying factors (measured by RQ-PCR). Samples are bone marrow from normals, patients with low risk MDS (<5% myeloblasts), and high risk MDS/AML (>5% myeloblasts). FIG. 9C) WHO classification and detected chromosome abnormalities in the analyzed samples. FIG. 9D) In MDS and AML bone marrow, the direction of methylation change at differentiation responsive CpG sites mimics that seen during normal differentiation, only exaggerated.

Methylation levels are represented by a β-value between 0 (unmethylated) and 1 (fully methylated). Promoter CpG sites were classified into 3 categories: CpG sites that undergo a significant (p<0.001, t-test) increase in methylation from normal stem and progenitor cells (HSPC, NCD34+) to normal mature cells (NBM) (108 CpG, 'hypomet. in NCD34+') (left box plots); CpG sites that undergo a significant (p<0.001, t-test) decrease in methylation from NCD34+ to NBM (162 CpG, 'hypermet. in NCD34+') (middle box plots); CpG sites that do not undergo a change in methylation between NCD34+ and NBM (1236 CpG, 'no met. change during n. diffn.') (right box plots). Asterixes represent statistically significant differences between the median in the sample group compared to the NBM group (Kruskal-Wallis). Actual p-values are: 'Hypomet in NCD34'—NBM v NCD34<0.0001, NBM v LoRisk <0.0001, NBM v HiRisk <0.0001. 'Hyper-met in NCD34'—NBM v NCD34<0.0001, NBM v LoRisk=0.024, NBM v HiRisk <0.0001. 'No Change'—NBM v NCD34<0.0001*, NBM v LoRisk NBM v LoRisk=0.024, NBM v HiRisk <0.0001, NBM v HiRisk <0.0001. NCD34=CD34+ cells isolated from normal bone marrow (n=9), NBM=normal whole bone marrow (n=42), LoRisk=bone marrow from low-risk MDS patients (n=27), HiRisk=bone marrow from high-risk MDS/AML patients (n=130). Box-plot boundaries=inter-quartile range, horizontal line=median, '+'=mean, whiskers=range of values, small boxes=out-lying values. #CpG were classified as 'no change in met' based on a t-test to compare means between NCD34 and NBM, whereas a Kruskal-Wallis test to compare medians is used here.

Example 9. A Model of Normal Differentiation and Leukemia Self-Renewal that Explains why DNMTI Depletion has Opposite Effects on Normal and Malignant Cells Differentiation mediated by a lineage-specifying transcription factor or by cytokines (Milhem, M., et al. 2004 Blood 103:4102-4110) requires orderly repression of stem-cell associated genes followed by upregulation of differentiation-fate associated genes. The repression of stem-cell associated genes requires chromatin modifying proteins such as DNMTI. Therefore, DNMTI depletion, by preventing this initial phase, prevents differentiation and maintains self-renewal of dividing normal stem-cells, even in differentiation inducing conditions (Milhem, M., et al. 2004 Blood 103:4102-4110) (data not shown).

In a substantial number of AML cases, differentiation arrest occurs after lineage-commitment (hence AML cells express lineage markers and high levels of lineage-specifying factors) and after the phase of stem-cell associated gene repression. Therefore, the self-renewal (proliferation at the same level of differentiation) of the leukemia cells is an aberrant persistence of the cell-division of differentiating cells, which is usually terminated by completion of the differentiation process. The differentiation impairment which maintains this abnormal self-renewal, although it may be initiated by genetic abnormalities, is finally mediated by epigenetic mechanisms that aberrantly repress genes necessary for differentiation. Therefore, DNMTI depletion to antagonize the transcription repression machinery restores the differentiation for which these cells are poised and thereby terminates the abnormal self-renewal. Observations in cancer cell lines representing a spectrum of cancer histologies indicate that the proposed model is relevant in many cancers.

Figure 10:
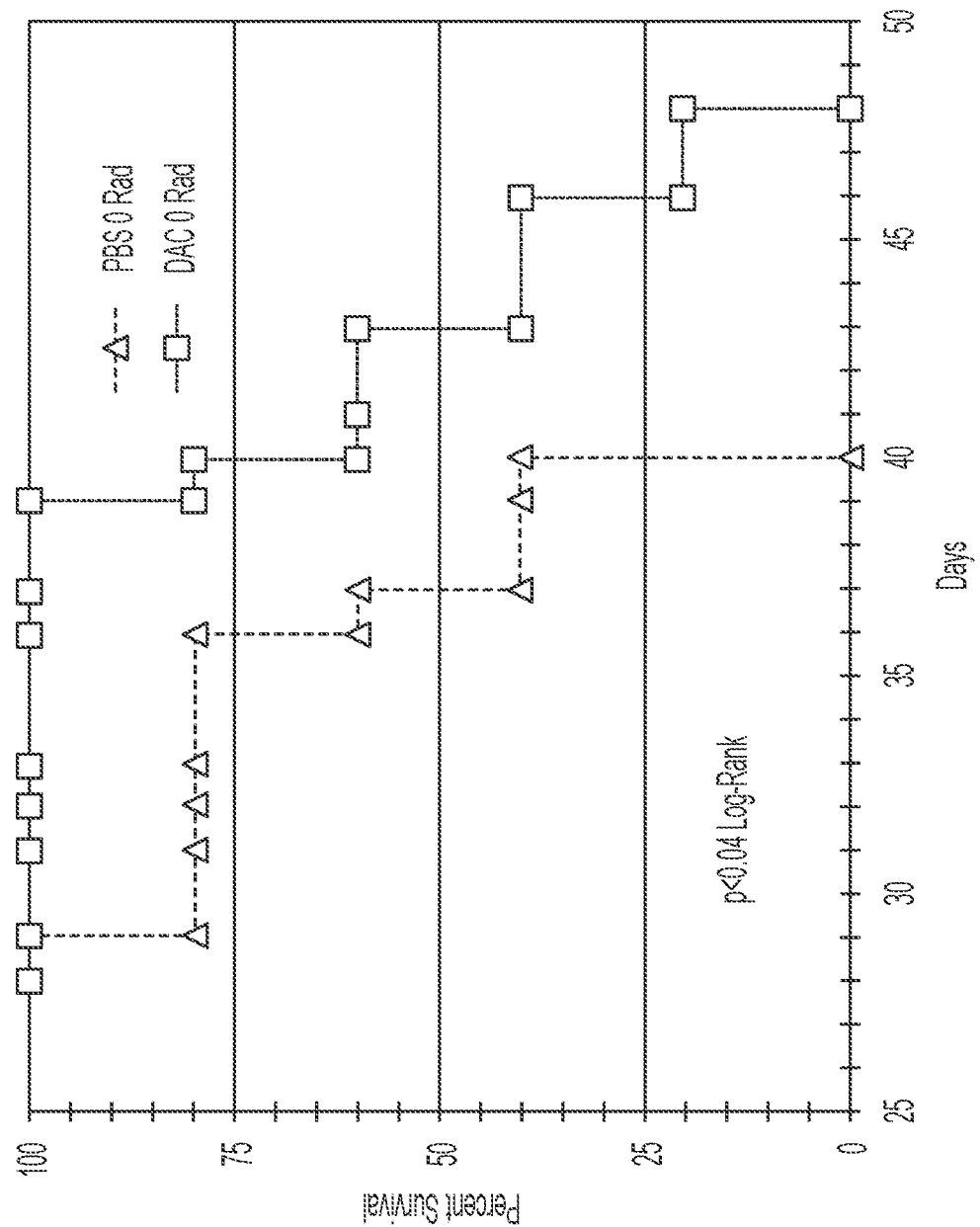
FIG. 10 plots the survival of leukemic mice untreated vs. treated with decitabine.

Example 10. Translation of these In Vitro Observations into Effective In Vivo Therapy Must Overcome a Number of Pharmacologic Obstacles The MA9 xenograft model of human leukemia was treated with intraperitoneal decitabine alone (I mg/m² 3×/week). Decitabine increased survival by approximately 20%, but all mice succumbed to leukemia (FIG. 10). This poor result, which did not reflect the in vitro findings, highlights the pharmacologic barriers that limit the in vivo activity of decitabine and hinder successful translation of very promising in vitro findings. CDA is the most important pharmacologic barrier to successful translation of in vitro findings into in vivo therapy. The invention addresses this barrier to effective clinical translation of the in vitro observations.

An antagonist of the decitabine degrading enzymecytidine deaminase (CDA)-tetrahydrouridine (THU). THU is a pyrimidine analogue that inhibits CDA (Ki 3-5×10-8M). THU has a benign toxicity profile, well-characterized PK, and has been administered to humans by intravenous (IV), sub-cutaneous (SQ), and oral (PO) routes in a number of clinical trials (Ho, D. H., et al. 1978 J Clin Pharmacol 18:259-265; Kreis, W., et al. 1977 Cancer Treat Rep 61:1347-1353; Kirch, H. C., et al. 1998 Exp Hematol 26:421-425; Yue, L., et al. 2003 Pharmacogenetics 13:29-38; Gilbert, J. A., et al. 2006 Clin Cancer Res 12:1794-1803; Bhojwani, D., et al. 2006 Blood 108:711-717; Liu, Z., et al. 2007 Nucleic Acids Res 35:e31).

Example 11. Pharmacologic Obstacle: Inter-Individual Variation in Response to Cytosine Analogues The AA genotype of CDA is associated with poor outcome in response to nucleoside analogue therapy. In humans, CDA is subject to a non-synonymous single nucleotide polymorphisms (SNP) (RS2072671) which produces an A→C transition in the ancestral allele, changes lysine to glutamine at amino-acid position 27 and decreases CDA activity 3-fold (Gilbert, J. A., et al. 2006 Clin Cancer Res 12, 1794-1803; Kirch, H. C. et al. 1998 Exp Hematol 26, 421-425; Yue, L., et al. 2003 Pharmacogenetics 13, 29-38). In the human hapmap (publicly available haplotype map of the human genome), 40% of Caucasians are homozygous with the AA genotype, 50% heterozygous with AC genotype and 10% homozygous with CC genotype (AA frequency is >90% in Asians and Africans). Since CDA can mediate cancer resistance to cytosine analogues, it was examined whether these different genotypes of CDA predicted clinical outcomes in MDS and AML patients treated with cytosine arabinoside (ARA-C), 5-azacytidine, or decitabine.

The AA genotype of CDA, which has greater enzymatic activity, is associated with early relapse during cytosine analogue therapy but not with non-cytosine analogue therapy. It was hypothesized that the more enzymatically active AA genotype of CDA, by further limiting the activity of cytosine analogues (ARA-C, 5-azacytidine or decitabine), could cause primary resistance or early relapse (relapse within 2 years) in MDS or AML patients treated with these drugs, but not in MDS or AML patients not being treated with cytosine analogues. Using the Human NS-12 BeadChip (Illumina, San Diego, Calif.) and allele-specific DNA sequencing, 24 month survival was stratified by CDA genotype in 81 MDS and AML patients treated at the Cleveland Clinic. As expected, the AA genotype was associated with decreased 24 month survival (p=0.05 Cox) in patients treated with cytosine analogues (data not shown). Numbers for the CC genotype are small, but it could be proposed that CC genotype may increase mortality from toxicity, but decrease relapse mortality. In patients who were not treated with cytosine analogues (these patients received arsenic or gemtuzumab), CDA genotype did not influence survival outcome (data not shown).

This data may explain the poorer leukemia outcomes seen in non-Caucasian populations (who are >90% AA genotype), and indicates that the combination decitabine-tetrahydrouridine (THU) agent contemplated herein should be a significant advance in MDS and AML therapy (and possibly therapy for other cancers) in all populations, since by inhibiting CDA, it is likely to address a major mechanism that underlies poor outcome with cytosine analogues.

Early relapse of leukemia is believed to represent selection for chemo-resistant clones, whereas late relapse may represent the emergence and evolution of leukemia stem-cells that were quiescent and unexposed to induction and consolidation chemotherapy. The combination of decitabine with THU has the potential to address both forms of relapse. Early relapse can be reduced by improving the pharmacologic profile (increasing time above threshold concentration, decreasing inter-individual variation) of decitabine. The lack of toxicity of the proposed approach, which should facilitate chronic, long-term therapy, may address late relapse, since even relatively quiescent LSC should at some point be exposed to chronically administered decitabine.

Example 12. Pharmacologic Obstacle: The Very Brief In Vivo Half-Life of Decitabine As seen above, CDA genotype is associated with significantly different outcomes in response to cytosine analogue therapy. This reflects the very large influence CDA has on cytosine analogue therapy in vivo: (i) Because of destruction by the enzyme CDA, the in vivo half-life of IV decitabine is <20 minutes, compared to an in vitro half-life of 5-9 hours (Liu, Z., et al. 2006 Rapid Common Mass Spectrum 20: 1117-1126). In order to exploit decitabine's unique quality amongst nucleoside analogues, its ability to deplete DNMTI at low concentrations, the pharmacologic objective of therapy is to maximize time-above-threshold concentration for depleting DNMTI (>0.2 µM), while avoiding the high peak levels (>I µM) that damage DNA (the DNA damage that occurs at higher levels causes toxicity that limits the cumulative dose of drug and is, therefore, counter-productive). To examine how different routes of administration might serve this pharmacologic objective, decitabine pharmacokinetics were studied in the non-human primate baboon model.

Figure 11:
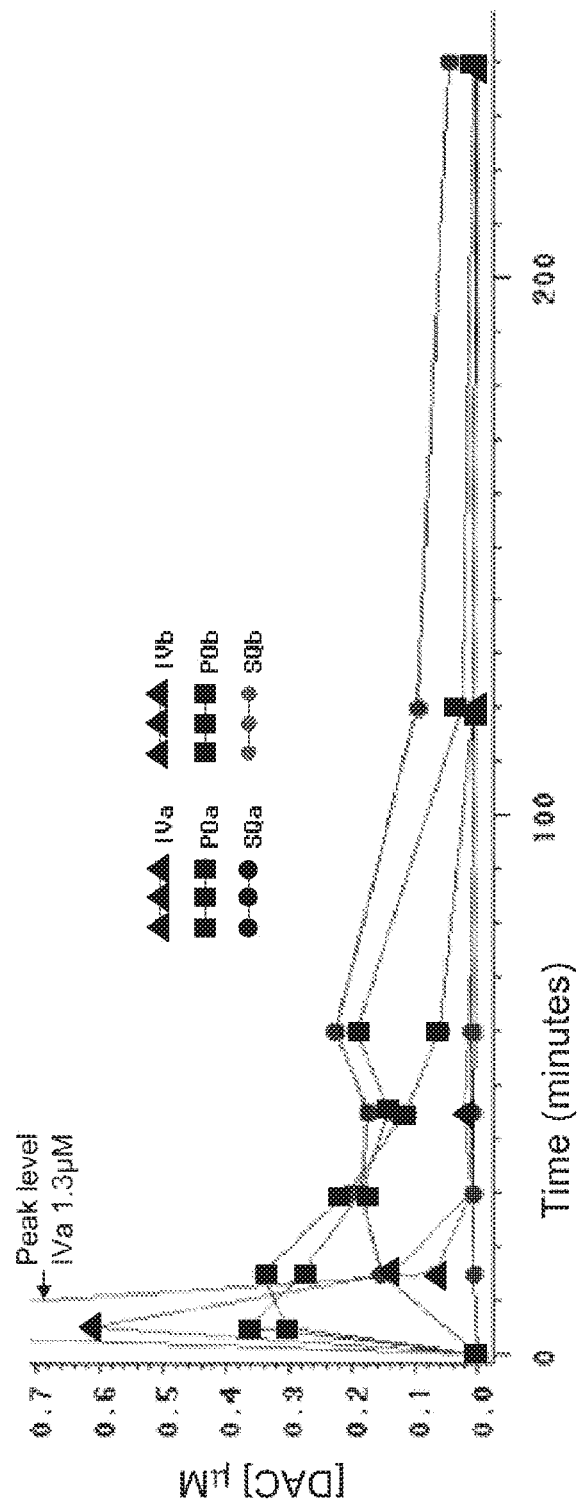
FIG. 11 graphically depicts decitabine peak levels and time-above-threshold for DNMTI depletion produced by subcutaneous vs. oral decitabine.

FIG. 11: Subcutaneous (SQ) and oral decitabine produces lower peak levels but a longer time-above-threshold for DNMTI depletion (~0.2 µM) than IV decitabine. Baboons were treated with IV decitabine 0.5 mg/kg (2 animals), SQ decitabine 0.5 mg/kg (2 animals), or oral decitabine 10 mg/kg (2 animals). Blood was collected for pharmacokinetic (PK) analysis at 7 time-points per animal and decitabine levels measured by LC-MS (Liu, Z., et al. 2006 Rapid Common Mass Spectrum 20:1117-1126). This data demonstrates: (i) SQ and oral administration can produce a longer time-above threshold concentration (~0.2 µM) for depleting DNMTI than IV decitabine. Indeed, intravenous (IV) decitabine has an abbreviated half-life of <20 mins; (ii) IV administration, but not SQ or oral, can produce peak levels (>I µM) associated with DNA damage; (iii) Significant inter-individual variability in PK that is most prominent with oral administration of the drug.

Example 13. Pharmacologic Obstacle: Malignant Cell Resistance to Decitabine is Pharmacological Rather than Biological Resistance to the effects of decitabine appears to be pharmacologic rather than biological, i.e., resistance is associated with a failure of decitabine to deplete DNMTI, rather than continued proliferation despite depletion of DNMTI.

Figure 12A:
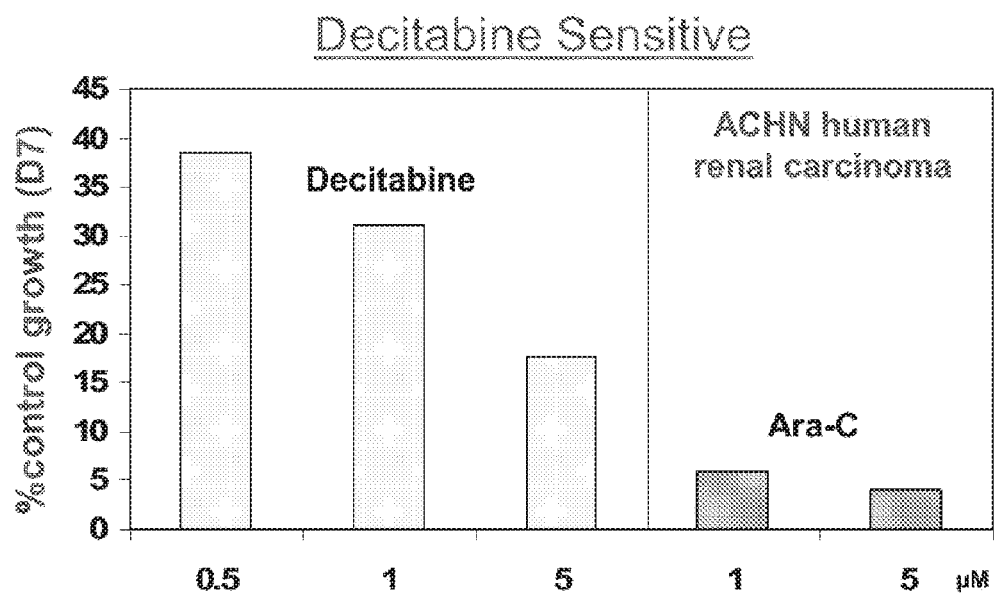
FIGS. 12A and 12B show, in bar graph form, DNMTI depletion in decitabine-sensitive and decitabine-resistant cell lines (in terms of % control growth for the bar graphs).
Figure 12B:
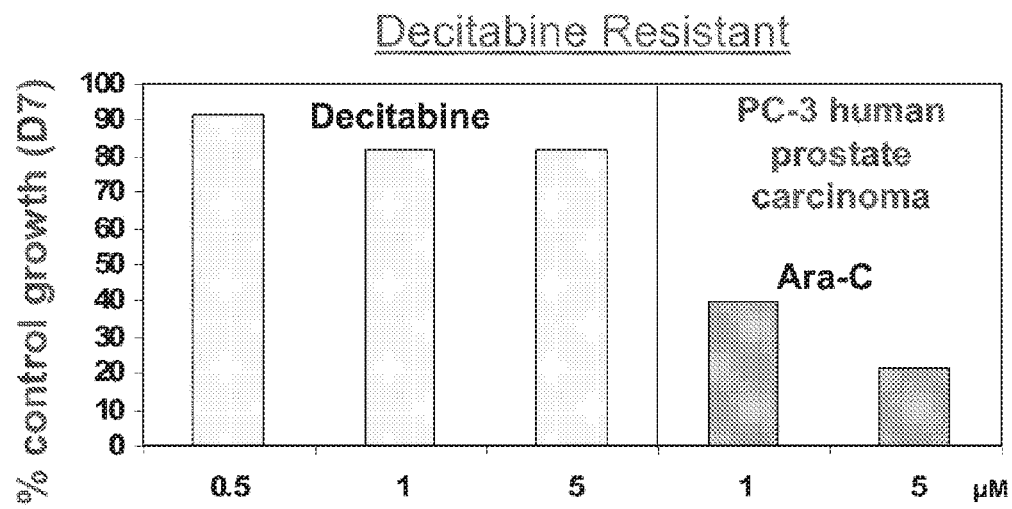

FIGS. 12A and B) Using the Q-Dot immunofluorescence assay for DNMTI levels, decitabine-sensitive cell lines demonstrate DNMTI depletion from the nucleus (in comparison with decitabine-resistant cell lines). However, the decitabine-resistant cell-line PC3 demonstrated persistent DNMTI expression. This indicates that the mechanism of resistance involves decreased decitabine entry into the cell, increased decitabine destruction CDA, or decreased activation by DCK.

Figure 14:
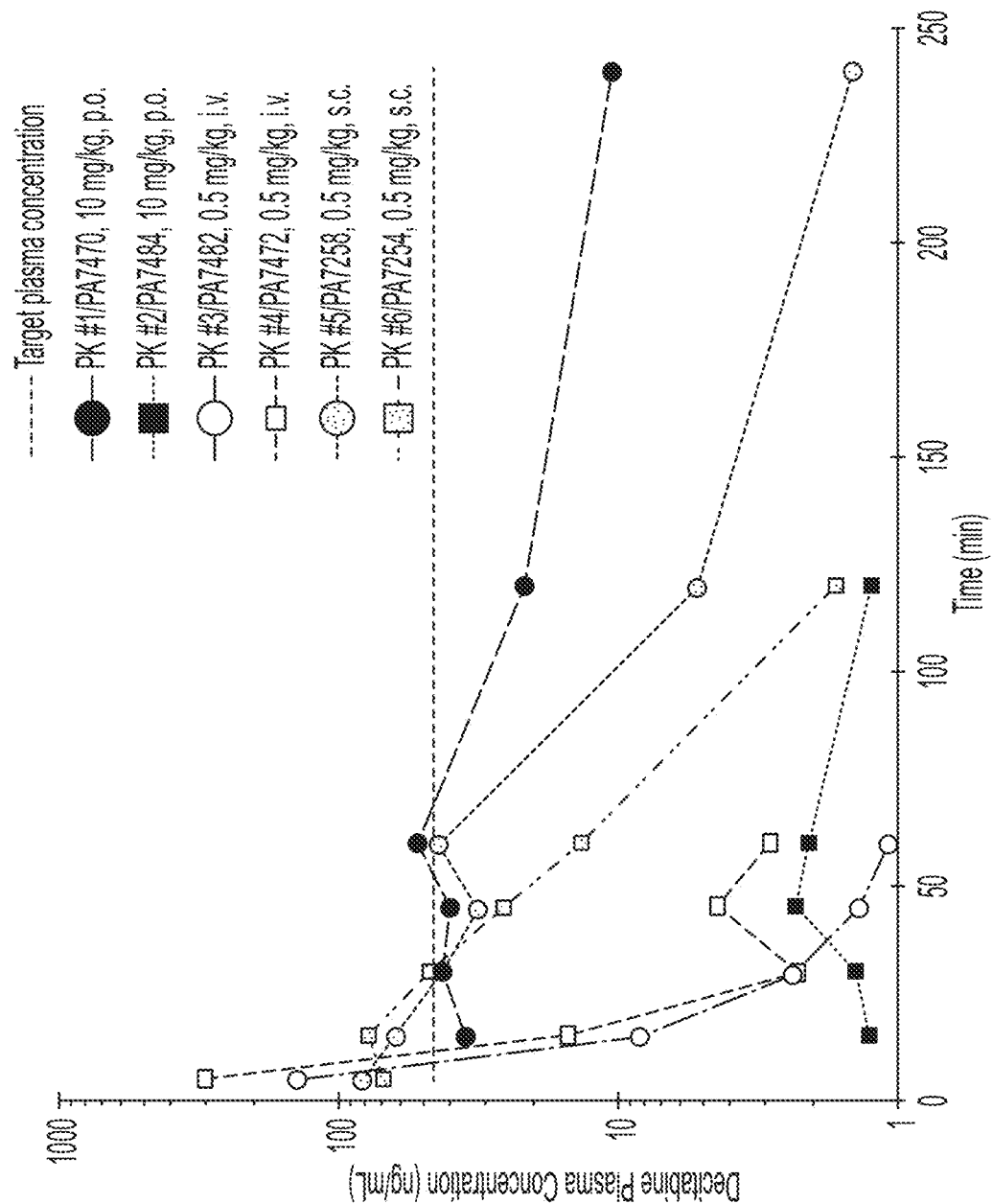
FIG. 14 graphically depicts plasma concentration-time curves of decitabine in non-human primates.

Example 14. Non-Clinical Pharmacokinetics of Decitabine Alone and in Combination with THU Pharmacokinetics of decitabine in non-human primates, poor oral bioavailability of decitabine in non-human primates: the pharmacokinetics of decitabine were assessed in two baboons following oral, SQ and intravenous administration. This experiment demonstrated that the oral bioavailability of decitabine in these two baboons ranged from approximately 0.2% to 7.0% (FIG. 14). Decitabine was administered to two baboons IV (0.5 mg/kg), SQ (0.5 mg/kg) and orally (10 mg/kg). Blood was collected at 7 time-points and plasma concentrations were determined using an LC/MS/MS method adapted from a previously published method 26. This data demonstrates: (i) that SQ and oral administration can produce a longer time-above-threshold concentration (~0.2 µM) for depleting DNMTI than IV decitabine; (ii) that at the doses studied, IV administration, but not SQ or oral, can produce peak levels (>I µM) associated with DNA damage; and (iii) significant inter-individual variability in decitabine exposure that is most prominent with oral administration of the drug.

Figure 15:
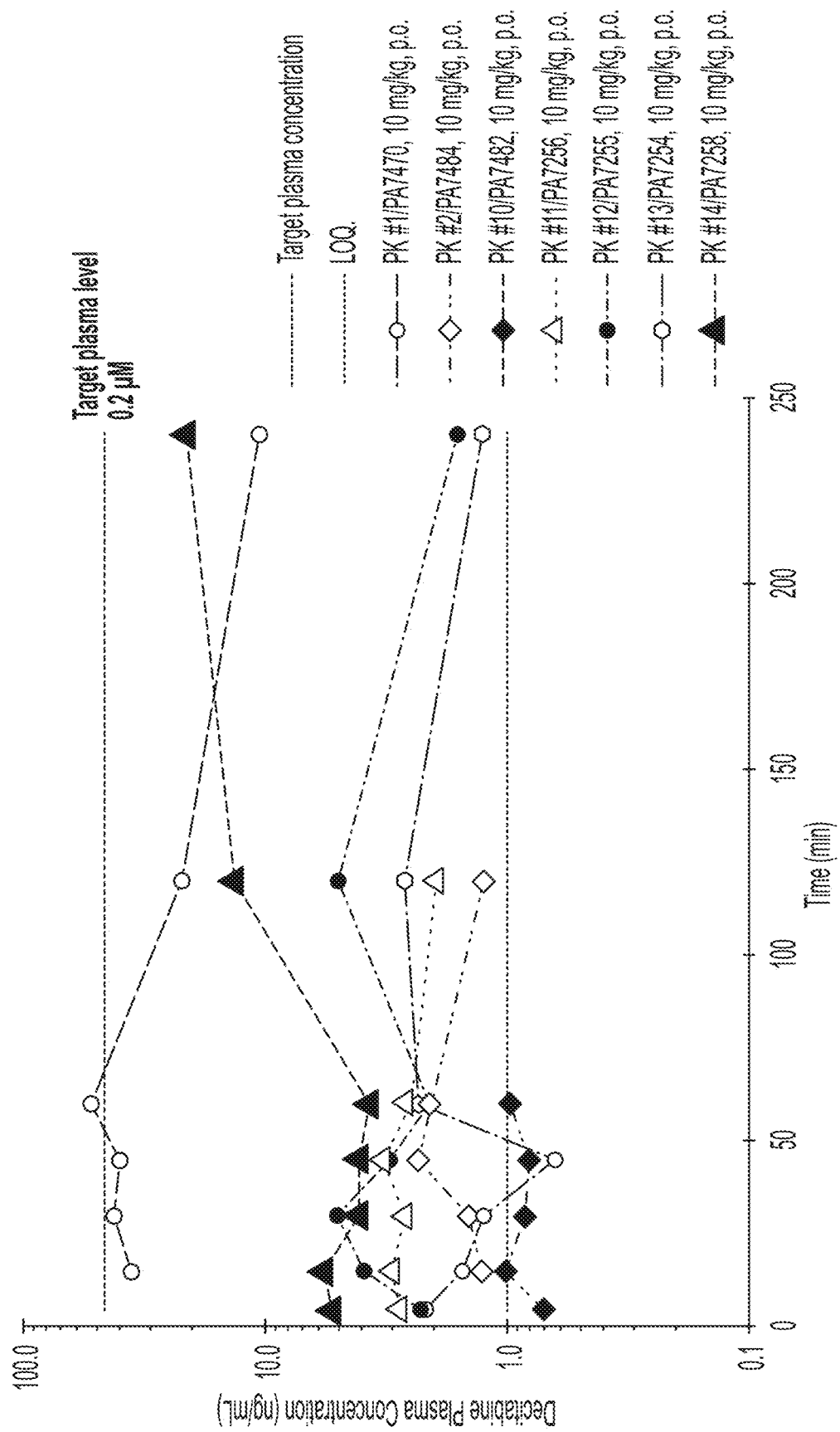
FIG. 15 graphically depicts plasma concentration-time curves of decitabine following oral administration to baboons at 10 mg/kg.

Example 15. Substantial Inter-Individual Variation in Oral Bio-Availability of Decitabine in Baboons Inter-individual variability was likewise seen in seven baboons that received 10 mg/kg decitabine orally, with the PK being measured at 6 or 7 time-points (FIG. 15).

Figure 16:
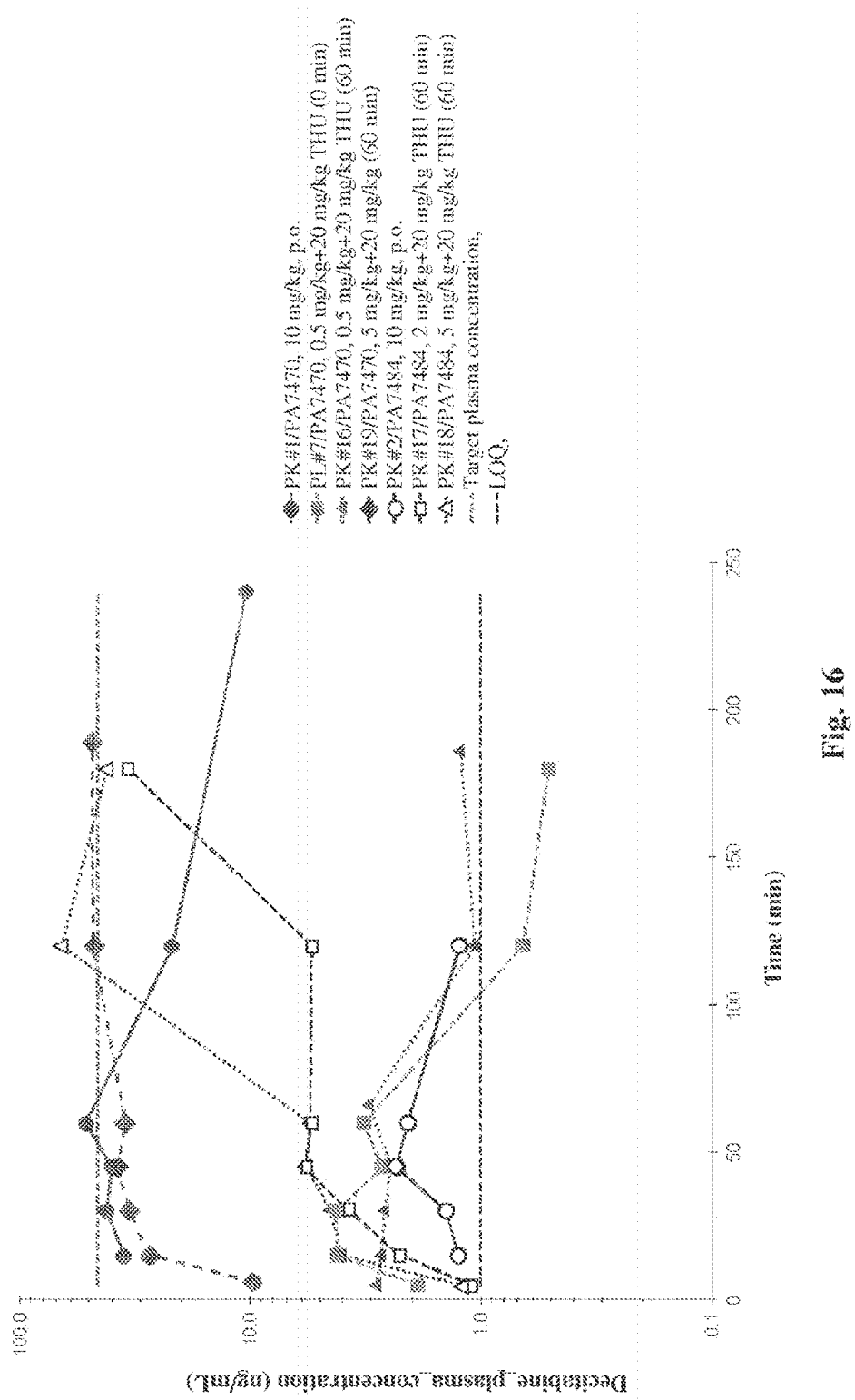
FIG. 16 graphically depicts plasma concentration-time curves of decitabine in baboons following oral administration alone or 60 minutes after THU.

Example 16. Administration of Oral THU Prior to Oral Decitabine Addresses the Substantial Inter-Individual Variability in Oral Bio-Availability of Decitabine High and low responder baboons (PA7470 and PA7484, respectively) were given 10 mg/kg decitabine alone, 0.5 mg/kg decitabine and 20 mg/kg tetrahydrouridine (THU) concurrently, or 0.5, 2, or 5 mg/kg decitabine 60 minutes after 20 mg/kg tetrahydrouridine (THU). Cmax (ng/mL), Tmax (min), and AUClast (min*ng/mL) were measured and are shown in Table 1, below, and FIG. 16. Following the oral administration of drugs, the plasma concentration generally reaches, in principle, a single, well-defined peak (Cmax) at the time of Tmax. AUClast refers to the area under a plotted plasma concentration-time curve (not shown) at the last recorded timepoint.

TABLE 1

| Animal | Decitabine (mg(kg) | Cmax (ng/mL) | Tmax (min) | AUClast (min*ng/mL) |
| --- | --- | --- | --- | --- |
| PA7470 | 10 mg/kg | 51.59 | 60 | 6278.775 |
| PA7470 | 0.5 mg/kg + 20 mg/kg THU ( 0 min) | 4.24 | 30 | 347.25 |
| PA7470 | 0.5 mg/kg + 20 mg/kg THU (60 min) | 3.06 | 66 | 356.81 |
| PA7470 | 5 mg/kg + 20 mg/kg THU (60 min) | 48.54 | 189 | 7534.665 |
| PA7484 | 10 mg/kg | 2.33 | 45 | 190.35 |
| PA7484 | 2 mg/kg + 20 mg/kg THU (60 min) | 34.01 | 180 | 1729.15 |
| PA7484 | 5 mg/kg + 20 mg/kg THU (60 min) | 65.87 | 120 | 5621.05 |

Of note, the administration of THU and decitabine increases the oral bioavailability of decitabine in the poor responder baboon and converges the PK between poor and good responder baboons ($4^{th}$ and $7^{th}$ values in final column) in comparison with decitabine alone ($1^{st}$ and $5^{th}$ values in final column). In effect, combining THU with oral decitabine increased the exposure of decitabine approximately 60-fold in an animal with relatively low bioavailability and approximately 2-fold in an animal with relatively high bioavailability, such that the extensive inter-individual variability in decitabine exposure was substantially reduced.

Example 17: Identifying the Dose of THU to Use to Increase Oral Bioavailability

Figure 17:
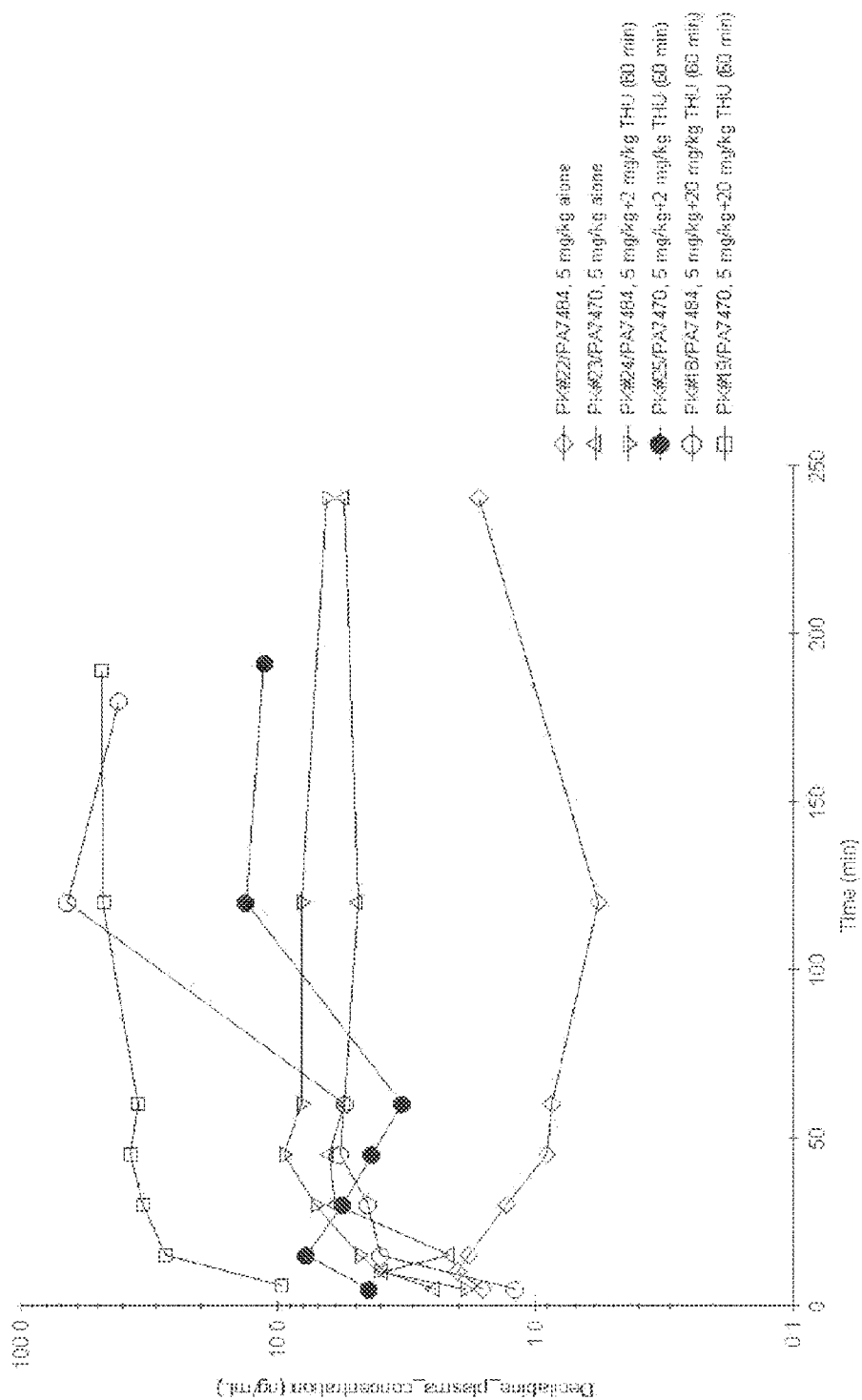
FIG. 17 graphically depicts plasma concentration-time curves of decitabine in baboons following oral administration alone at 5 mg/kg or 60 minutes after 2 or 20 mg/kg THU.

Baboons received varying doses (2 mg/kg or 20 mg/kg) of tetrahydrouridine 60 minutes before a dose (5 mg/kg) of decitabine. Two baboons (PA7484 and PA7470) were administered oral THU 20 mg/kg (400 mg/m$^2$) 60 minutes prior to oral decitabine 5 mg/kg, or decitabine alone. After a wash-out period of greater than 2 weeks, these same two animals were administered oral THU 2 mg/kg (50 mg/m$^2$) 60 minutes prior to oral decitabine 5 mg/kg, or oral decitabine alone. Unlike 20 mg/kg (500 mg/m$^2$), 2 mg/kg (50 mg/m$^2$) of THU was insufficient to achieve the target plasma concentration of decitabine of >50 ng/mL (FIG. 17). Both doses of tetrahydrouridine significantly increased decitabine oral bio-availability, but this increase was significantly greater with the higher dose (500 mg/m$^2$, or, 20 mg/kg) of tetrahydrouridine.

Example 18. Identifying the Optimal Timing Between Oral THU and Oral Decitabine Administration (Oral Bio-Availability of Decitabine Upon Concurrent Vs. Prior Administration of Tetrahydrouridine)

High-responder and low-responder baboons each received either 20 mg/kg (500 mg/m$^2$) tetrahydrouridine (THU) orally 60 minutes before oral administration of 5 mg/kg decitabine or concurrently with the decitabine. Decitabine levels were measured at various timepoints by LC-MS.

Notably, when the tetrahydrouridine was given orally concurrently with the decitabine, the oral bio-availability of the latter exhibited a significant drop-off in comparison to administration of the tetrahydrouridine 60 minutes prior to decitabine (data not shown).

Figure 18A:
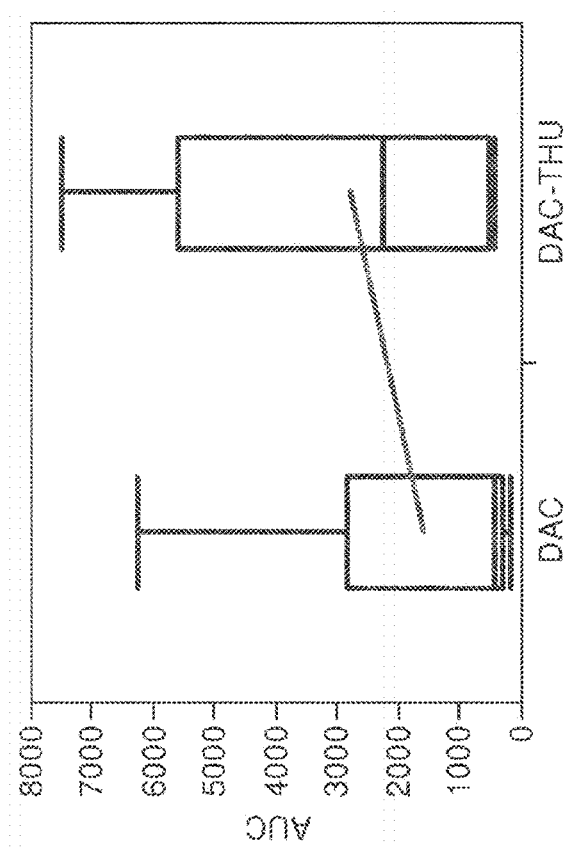
FIG. 18A depicts, in bar graph form, the distribution of AUC in 7 animals treated with decitabine 10 mg/kg alone by oral gavage or THU 20 mg/kg by oral gavage followed by decitabine 5 mg/kg by oral gavage 60 minutes later. Horizontal line in box–plot=median, box boundaries=interquartile range, connecting diagonal line joins the mean in the two groups. The wide separation of median and mean in the decitabine only group is narrowed substantially in the decitabine-THU group. The difference in medians between the two groups was not statistically significant (p=0.22, Wilcoxon). The difference in means between the two groups was not statistically significant (p=0.08, paired t-test).
Figure 18B:
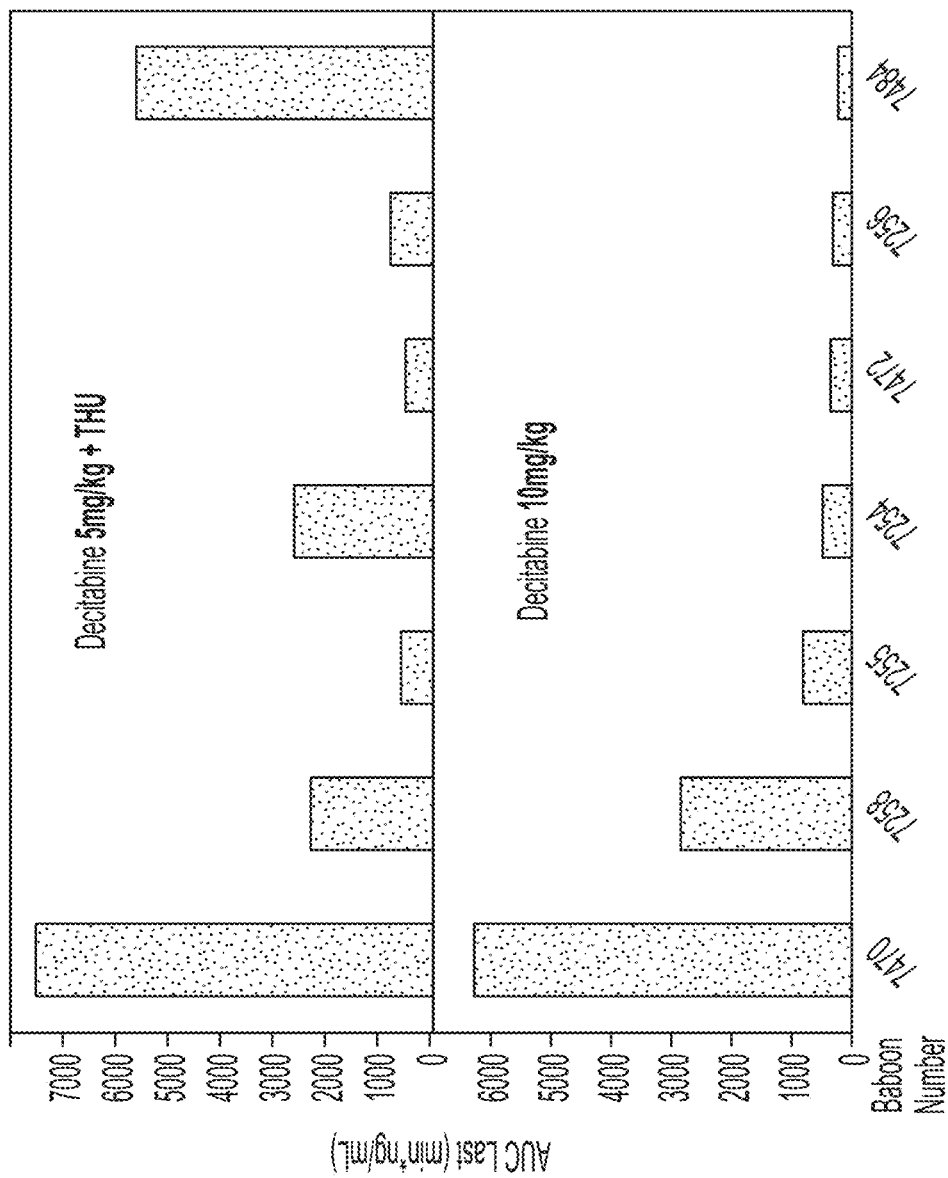
FIG. 18B depicts, in bar graph form, the results of A broken down by individual animals.

Example 19: Confirmation that Oral THU Increases the Oral Bio-Availability of Decitabine Approximately 4-Fold, and Decreases the Substantial Inter-Individual Variation in Decitabine Oral Bio-Availability In seven baboons, the administration of THU prior to decitabine increased the oral bioavailability of decitabine approximately 4-fold and decreased inter-individual variation in decitabine pharmacokinetics. Seven baboons were treated with decitabine alone 10 mg/kg by oral gavage, or after a wash-out period of at least 2 weeks, with THU 20 mg/kg by oral gavage followed by decitabine 5 mg/kg by oral gavage. In 7 animals administered oral decitabine alone at 10 mg/kg, the mean AUC was 1604 and the median AUC was 463 min*ng/ml (FIG. 18A). In these same 7 animals administered THU 20 mg/kg followed by half the dose of decitabine (5 mg/kg), the mean AUC was 2820.914 and the median AUC was 2284 min*ng/ml (FIG. 18A). Therefore, administering oral THU prior to oral decitabine produced a fold-increase in oral bioavailability of approximately 10-fold when considering medians, and approximately 3.5-fold when considering means. The largest increases in AUC with co-administration were seen in the animals with low AUCs with decitabine alone (FIG. 18B). Therefore, the large inter-individual variation seen with decitabine alone, represented by the separation between mean and median AUC, was substantially dampened by coadministration of THU with decitabine (FIG. 18A).

Mice received varying doses (30 mg/kg, 15 mg/kg, and 7.5 mg/kg) of tetrahydrouridine 30 minutes before a dose (16 mg/kg) of decitabine. Decitabine levels were measured by LC-MS. 50 mg/m tetrahydrouridine administered prior to the administration of decitabine resulted in an approximately 5-fold (certainly pharmacologically significant) increase in decitabine oral bio-availability (data not shown). A slight drop-off was observed in decitabine oral bio-availability measured when the dosage of THU was decreased from 50 to 25 mg/m.

Of note, a similar cytidine deaminase expression pattern is found in humans and mice (data not shown). This gene expression data can be obtained from the public gene expression database GenAtlas.

Example 20. Phase 1/2 Study of Chronic Low Dose IV Administration of Decitabine in SCD Based on previously conducted trials, in which no clinically significant adverse events occurred, a chronic administration study was conducted to identify the toxicity and effectiveness of repeated decitabine dosing over 36 weeks (9 months) in 7 subjects with HU refractory SCD (DeSimone, J., et al. 2002 Blood 99:3905-3908). Decitabine was administered by I. V. infusion at 0.3 mg/kg/day, 5 consecutive days per week for 2 weeks, followed by a 4-week observation period. If the absolute neutrophil count (ANC) dropped below $1\times109/L$, the dose was reduced by 0.05 g/kg/day in the next 6-week cycle. An optimal drug dose was obtained for each subject, and resulted in an elevated HbF without neutropenia (ANC nadir>$1.5\times109/L$).

Pharmacodynamic effects: the average HbF and average maximal HbF levels attained during the last twenty weeks of treatment for the 7 SCD subjects were 13.93±2.35% and 18.35%±4.46%, respectively (from a base-line of 3.12%±2.75%). The average and average maximal hemoglobin values were 8.81±0.42 g/dL and 9.7±0.53 g/dL, respectively (from a base-line of 7.23±2.35 g/dL) (Table 2, below).

TABLE 2

Hemoglobin and HbF levels before and during the last 20 of 36 wks of treatment with decitabine

| | | HbF (%) | | Total Hemoglobin (g/dL) | | |
|---|---|---|---|---|---|---|
| Subject | Pre | Avg | Max | Pre | Avg | Max |
| 1 | 0.8 | 12.40 ± 1.25 | 14.4 | 6.2 | 9.05 ± 0.48 | 9.6 |
| 2 | 6.8 | 14.55 ± 1.32 | 16.3 | 8.2 | 9.37 ± 0.60 | 10.3 |
| 3 | 1.4 | 12.75 ± 2.28 | 17.2 | 6.0 | 8.34 ± 0.55 | 9.5 |
| 4 | 0.6 | 10.80 ± 2.05 | 14.4 | 7.2 | 8.28 ± 0.52 | 9.0 |
| 5 | 2.9 | 16.42 ± 2.81 | 24.6 | 8.0 | 8.91 ± 0.57 | 9.6 |
| 7 | 6.2 | 16.70 ± 2.55 | 23.2 | 7.8 | 8.92 ± 0.79 | 10.4 |
| Mean ± SD | 3.12 ± 2.75 | 13.93 ± 2.35 | 18.35 ± 4.46 | 7.32 ± 0.94 | 8.81 ± 0.42 | 9.73 ± 0.53 |

Individual maximal F-cell numbers during the trial ranged from 58-87% (i.e., an average over all 7 subjects of 69±10.12%).

Hematologic side-effects and toxicity: despite periodic depressions in ANCs, which occurred 5 to 6 weeks after beginning each treatment cycle, the average ANC during the last 20 weeks of treatment ($4.2\pm1.35\times109/L$) was not significantly different from the pretreatment average ($4.6\pm1.56\times109/L$). The ANCs of two HU non-responder subjects never fell below $2.0\times109/L$ and the nadirs, which occurred at 5-6 weeks of each cycle, generally remained above $3.0\times109/L$. No clinical sequelae of blood count changes occurred.

Non-hematologic toxicity: no non-hematologic toxicity occurred. Patients did not require anti-emetics.

Example 21. Phase ½ Study of SQ Administration of Decitabine

A Phase ½ study was initiated using decitabine given by the SQ route in order to assess the safety of decitabine given by the SQ route, to produce cumulative increases in fetal and total hemoglobin through weekly administration, and to explore the mechanism by which decitabine increases HbF (Saunthararajah, Y., et al. 2003 Blood 102:3865-3870). Eight subjects with multiple clinically significant complications of SCD were treated. Decitabine was administered at 0.2 mg/kg SQ 1 to 3 times per week in 2 cycles of 6-week duration with a 2-week interval between cycles. In cycle 1, drug was administered twice per week on 2 consecutive days. If the patient achieved an F-cell percentage (% F-cells) of at least 80% during cycle 1, the dose frequency was reduced to once per week in cycle 2. If the highest % F-cells during the cycle 1 was less than 80%, the dose frequency was increased to 3 times per week in cycle 2.

Figure 13:
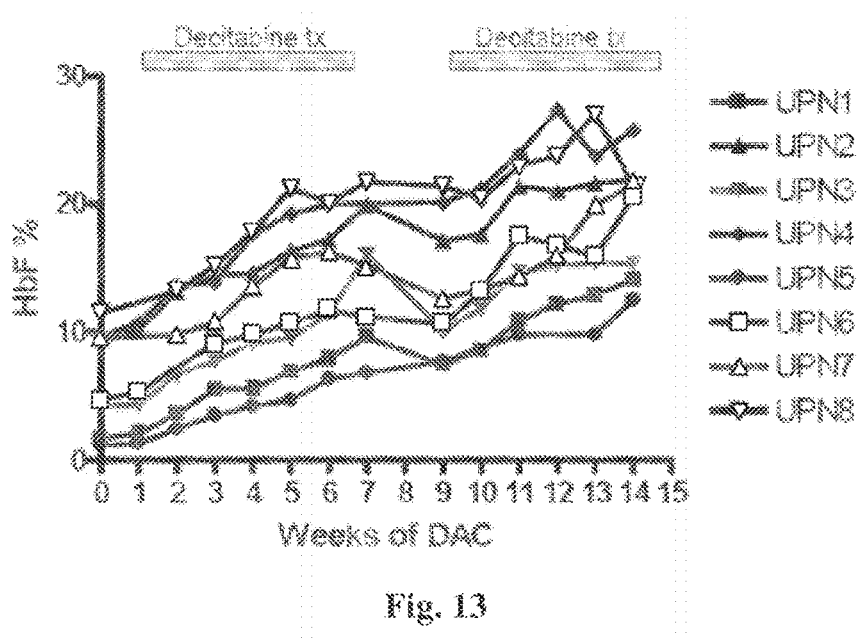
FIG. 13 graphically depicts HbF expression elevation over time associated with decitabine.

Pharmacodynamic effects: all subjects demonstrated statistically significant increases in HbF expression (FIG. 13). DNA methylation analysis of the γ-globin promoter in DNA isolated from bone marrow aspirate cells was demonstrated post-treatment hypomethylation at this locus (data not shown). At higher doses, decitabine is known to be cytotoxic. To determine if this dose and schedule of decitabine was cytotoxic, bone marrow morphology was evaluated by independent and blinded hematopathology review of pre-treatment and post-treatment bone marrow aspirates. There was no decrease in bone marrow cellularity. An increase in erythroid cells and megakaryocytes was noted (data not shown). Flow cytometric analysis of propidium iodine stained fresh marrow aspirate cells did not demonstrate an increase in the sub-GI apoptotic fraction (data not shown).

Hematologic side-effects and toxicity: one patient had (National Cancer Institute/Cancer Therapy Evaluation Program (NCI/CTEP) grade 4 neutropenia (nadir ANC 0.4× 103/μl), two had grade 3 neutropenia (nadir ANC 0.8×103/ μl). Neutropenia recovered within 7 days of the last decitabine dose. Neutropenic fever did not occur. Platelet counts increased in all subjects during treatment. The highest platelet count was 877×109/L. No clinical sequelae to these blood count changes occurred.

There was an inverse relationship between platelet and neutrophil counts (data not shown). The changes in bone marrow morphology and in vitro studies with non-cytotoxic levels of decitabine indicate that the mechanism of decreased neutrophils and concurrent increased platelets is altered hematopoietic stem cell differentiation (Saunthararajah, Y., et al. 2003 Blood 102:3865-3870).

Four patients consented to serial bone marrow aspirate and biopsy analysis before and each 6-wk cycle of decitabine treatment.

TABLE 3

Results of bone marrow aspirate and biopsy analysis.

| | Pre-Treatment | | | After Cycle 1 | | | After Cycle 2 | | |
|---|---|---|---|---|---|---|---|---|---|
| ID# | Cellu | M:E ratio | MK/ LPF | Cellu | M:E ratio | MK/ LPF | Cellu | M:E ratio | MK/ LPF |
| UPN1 | Hyper | 0.8 | 4 | Hyper | 0.7 | 10 | Hyper | 0.6 | 13 |
| UPN3 | Hyper | 0.8 | 2-3 | | | | Hyper | 0.3 | 6 |
| UPN5 | Norm | 2 | 2 | Norm | 0.8 | 6 | Norm | 0.5 | 6 |
| UPN7 | Hyper | 1 | 1 | Hyper | 0.3 | 8 | Hyper | 0.03 | 13 |

There was no decrease in marrow cellularity upon hematopathology review (Table 3, above), which was blinded to treatment status. In UPN3, the interim bone marrow aspirate was technically unsuccessful.

Non-hematologic toxicity: NCI Toxicity Criteria were used to assess toxicity. No local toxicity occurred at SQ injection sites. No non-hematologic toxicity occurred. No subjects described nausea, vomiting, diarrhea, constipation, or decreased appetite.

Efficacy: total Hb increased from 7.6±2 to 9.6±1.8 (mean±2 SD of pre-treatment to peak Hb, paired t-test p<0.001). Both the absolute reticulocyte count (ARC) (p=0.0006) and total bilirubin (p=0.01, 2-tailed paired t-test) decreased during treatment. The ARC correlated inversely with tHb (p<0.0001). In SCD, abnormal exposure of molecules such as phosphatidyl-serine on the RBC surface and adhesion of RBC to endothelial cells/endothelial damage can trigger coagulation and inflammatory pathways. RBC adhesion to both TSP and laminin decreased following cycle 1 (p<0.005). In agreement with previous reports (Tomer, A., et al. 2001 J Lab Clin Med 398-407; Francis, R. B., Jr. 1989 Haemostasis 19:105-111; Peters, M., et al. 1994 Thromb Haemost 71:169-172), increased levels in markers of active coagulation, Thrombin-antithrombin (TAT), FI+2 and D-dimers, were noted at baseline. Treatment decreased D-dimer levels, a measure of fibrinolysis of cross-linked fibrin (p<0.04), while markers of thrombin generation, TAT and FI+2, decreased, but not to a statistically significant extent. The adhesion molecule soluble VCAM (s VCAM-I) and von Willebrand factor peptide (VWFpp) are released from damaged endothelial cells, levels of both molecules decreased with treatment (p<0.05). C-reactive protein (CRP), a marker of inflammation, was elevated at baseline and, although there was a downward trend with therapy, it was not statistically significant (p=0.18) (see Table 4, below).

TABLE 4

Changes in surrogate clinical endpoints. Values are mean ± SE; paired 2-tailed t-test.

| | | Pretherapy | Post Cycle 1 | P* | Post Cycle 2 | P** | Normal Range |
|---|---|---|---|---|---|---|---|
| Measures of RBC adnesion to endothelium | Adhesion to TSP (RBCs/mm²) | 1570 ± 170 | 690 ± 150 | <0.001 | 910 ± 160 | <0.001 | <60 |
| | Adh. to laminin (RBCs/mm²) | 3470 ± 500 | 1950 ± 300 | 0.004 | 1570 ± 210 | <0.001 | <250 |
| Measures of thrombin generation and fibrinolysis | D-Dimer (ng/mL) | 490 ± 90 | 320 ± 50 | 0.02 | 300 ± 50 | 0.03 | <400 |
| | TAT (ug/L) | 7.0 ± 1.7 | 8.6 ± 2.3 | 0.15 | 5.2 ± 0.9 | 0.11 | 1.0-4.1 |
| | F1 + 2 (nmol/L) | 1.75 ± 0.22 | 1.56 ± 0.16 | 0.23 | 1.41 ± 0.15 | 0.051 | 0.04-1.1 |
| Measure of inflammation | CRP (mg/dL) | 1.25 ± 0.27 | 1.19 ± 0.34 | 0.80 | 0.82 ± 0.26 | 0.18 | <0.7 |

TABLE 4-continued

Changes in surrogate clinical endpoints. Values are mean ± SE; paired 2-tailed t-test.

|  |  | Pretherapy | Post Cycle 1 | P* | Post Cycle 2 | P** | Normal Range |
|---|---|---|---|---|---|---|---|
| Measures of endothelial cell damage | sVCAM (ng/mL) | 1170 ± 140 | 930 ± 100 | 0.01 | 840 ± 100 | 0.02 | 395-714 |
|  | VWFpp (u/dL) | 196 ± 26 | 156 ± 28 | 0.015 | 144 ± 13 | 0.049 | 74-153 |

P* = significance of change from pre-therapy to post-cycle 1.
P** = change from pre-therapy to post-cycle 2.

Example 22. Chronic Decitabine Administration to Seriously Ill SCD Patients (Saunthararaiah. Y. Et al. 2008 Br J Haematol 141:126-129)

Previous studies of decitabine as a potential disease-modifying agent for sickle cell disease (SCD) were not designed to demonstrate clinical effectiveness. In four SCD patients with severe acute illness on a background of chronic clinical deterioration over the preceding years or months, decitabine (0.1-0.2 mg/kg 1-2x/week) was administered off-label for periods beyond 12 months. The off-label use of decitabine in SCD was to provide direct benefit to these patients and not for research. Decitabine was considered because of clinical deterioration and life-threatening complications despite HU therapy, erythropoietin for relative reticulocytopenia (hemoglobin<9 g/dl & reticulocytes<250× 109/L), decreased availability, and increased transfusion risks from >5 red blood cell (RBC) allo-antibodies and auto-antibodies, and ineligibility for available protocol therapy.

Hemoglobin increases of >1.5 g/dl occurred within 2-4 weeks with maximum hemoglobin increases of 3.5-5 g/dl. Hemoglobin increased through an increase in reticulocytes and an increase in fetal hemoglobin (the increase in hemoglobin was not explained by increase in fetal hemoglobin alone). Generally, reticulocyte counts increased during the first 2-8 weeks of therapy. Reticulocyte trends reversed after hemoglobin levels >9 g/dl. This was most obvious in Patient A, who was not receiving exogenous erythropoietin. Durable symptom and performance status improvement during 4-12 months of follow-up contrasted with severe and deteriorating pre-decitabine trends.

Of note, all patients had severe acute illness on a background of chronic deterioration and progressive anemia over the preceding years or months; the follow-up period ranging from 4-12 months allowed documentation of durable clinical improvement that contrasted obviously with clinical status and trends in the preceding months; although 3 of the 4 patients were on concurrent erythropoietin, it had been administered at stable doses for more than 6 months with progressive anemia and recurrent severe anemia exacerbations; although 2 of the 4 patients received transfusions during decitabine therapy, these do not explain the durable increases in hemoglobin and eventual transfusion independence. The severe and complicated clinical circumstance in these patients is not typically represented in clinical trials. Therefore, this description can complement the clinical studies and provide additional guidance regarding dose, schedule, anticipated toxicities and inclusion criteria.

Example 23. Pharmacodynamics of Decitabine Alone and in Combination with THU

Significant inter-individual variability in pharmacodynamic responses in baboons. The biologic relevance of differences in pharmacokinetic responses to oral decitabine were examined in a different set of baboons, in which large differences in individual pharmacodynamic responses (fetal hemoglobin expression) and biologic activity (neutrophil counts) were noted (Table 5, below).

TABLE 5

Pharmacodynamic responses following SQ and oral administration of decitabine to baboons.

| Animal | Drug | Route | Dose mg/kg/d | Pre-HbF % | Post-HbF % | ANC nadir |
|---|---|---|---|---|---|---|
| 6974 | Dac | SQ | 0.52 | 7.7 | 68.8 | 1668 |
|  | Dac-m | Oral | 9.35 | 10.3 | 40.5 | 2000 |
|  | Dac-m | Oral | 18.7 | 7.7 | 67.8 | 1659 |
| 7001 | Dac | SQ | 0.52 | 7.2 | 66.1 | 1491 |
|  | Dac | Oral | 9.35 | 6.6 | 17.4 | 1331 |
|  | Dac-m | Oral | 4.1 | 7.4 | 13.1 | 1417 |
| 7002 | Dac | SQ | 0.52 | 7.4 | 86.3 | 524 |
|  | Dac-m | Oral | 6.7 | 7.9 | 31.4 | 481 |
|  | Dac-m | Oral | 9.35 | 8.3 | 62.3 | 463 |
| 7254 | Dac | SQ | 0.52 | 8.4 | 76.3 | 1320 |
|  | Dac | Oral | 18.7 | 7.1 | 68.1 | 1969 |
| 7257 | Dac | Oral | 9.35 | 6.0 | 72.0 | 749 |

Fetal hemoglobin expression, HbF %, pre and post treatment with the indicated dose of decitabine. Decreases in neutrophil counts, another expected biological effect of decitabine, paralleled the increases in HbF %. Oral treatment was with decitabine or a slightly modified decitabine (decitabine-mesylate—Dac-m). Inter-individual variability in pharmacodynamic responses to the same dose of oral decitabine are highlighted by the boxes.

Example 24. The Administration of THU Prior to Decitabine Decreases Inter-Individual Variability in Decitabine Similarly, administration of oral THU prior to oral decitabine in two other baboons (PA 6974 and 7001) produced a substantial increase in the pharmacodynamic responses (fetal hemoglobin expression) to oral decitabine (Table 6, below).

TABLE 6

Pharmacodynamic responses (fetal hemoglobin expression, HbF %) were substantially enhanced by administering oral decitabine after oral THU.

| Animal | Drug | Route | Dose mg/kg/d | THU oral 20 mg/kg | Pre-HbF % | Post-HbF % |
|---|---|---|---|---|---|---|
| 6974 | Dac | Oral | 9.35 | − | 10.3 | 40.5 |
|  | Dac | Oral | 0.3 | + | 3.2 | 28.4 |
| 7001 | Dac | Oral | 9.35 | − | 6.6 | 17.4 |
|  | Dac | Oral | 1.42 | + | 6.2 | 61.6 |

Decitabine was administered at the doses indicated in two consecutive blocks of 5 days each. THU at the indicated doses was administered 60 minutes before each decitabine dose.

Figure 19B:
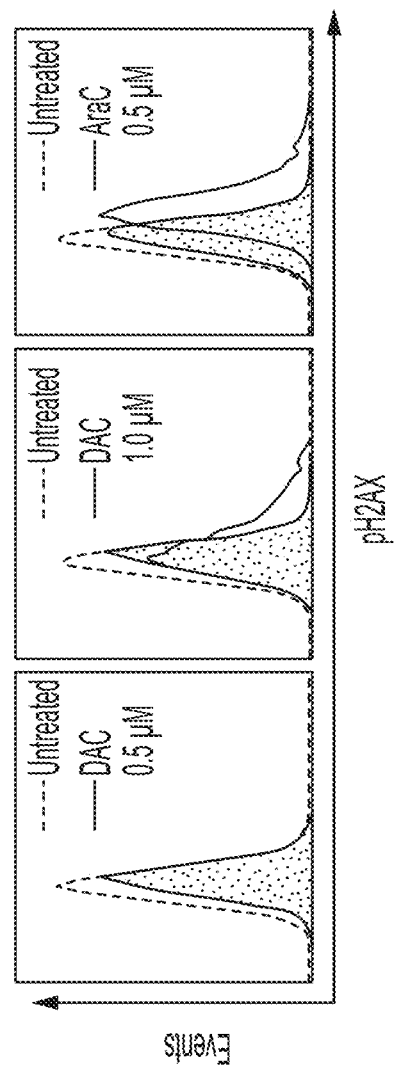
FIGS. 19A-19E illustrates effects of DAC on DNMT1 depletion, DNA damage, and apoptosis in normal hematopoietic precursors.
Figure 19C:
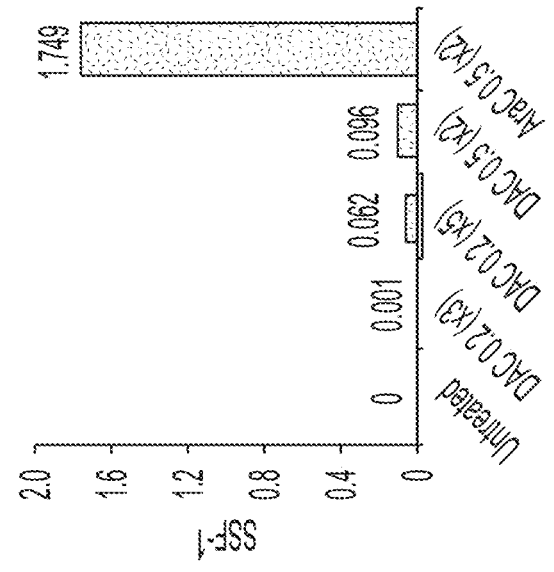

Example 25. The Effects of Decitabine (DAC) on DNMT1 Depletion, DNA Damage, and Apoptosis in Normal Hematopoietic Precursors FIGS. 19A-19E illustrates effects of DAC on DNMT1 depletion, DNA damage, and apoptosis in normal hematopoietic precursors. (FIG. 19A) DAC 0.005 µM depletes DNMT1 in normal hematopoietic precursors. Normal CD34 cells were isolated from cord blood. DAC 0.005 µM was added once daily on days 1-4 and DNMT1 was quantified by Western blot on day 5. (FIGS. 19B-C) DAC>0.5 µM was required to induce measurable DNA damage. Twenty-four hours after DAC or AraC exposure, DNA damage was measured by flow-cytometric assessment for phosphorylation of histone H2AX (γH2AX; B) or the Fast Micromethod for DNA scission (FIG. 19C). Equimolar levels of AraC were used as positive controls. Gray histogram is the isotype control. (FIG. 19D) DAC>0.5 µM was required to induce apoptosis. Twenty-four hours after DAC or AraC exposure, apoptosis was measured by flow-cytometric assessment for annexin staining. Double annexin/7-aminoactinomycin D (7AAD)-positive cells represent late apoptosis/necrosis. (FIG. 19E) DAC up to 0.5 µM in combination with THU did not cause significant DNA damage, as measured by flow-cytometric assessment of H2AX levels 24 hours after addition of the drug to normal hematopoietic precursors. Results are expressed as a percentage of vehicle treated controls.

Figure 19A:
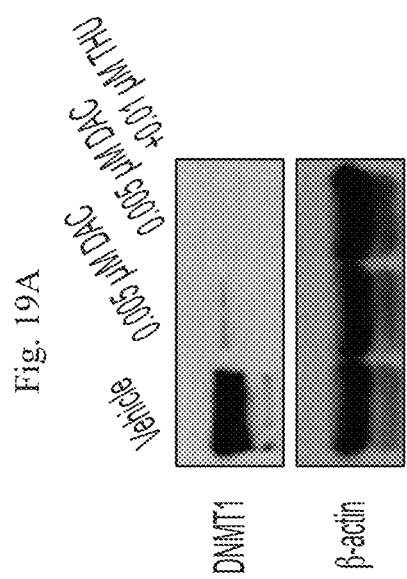
Figure 19D:
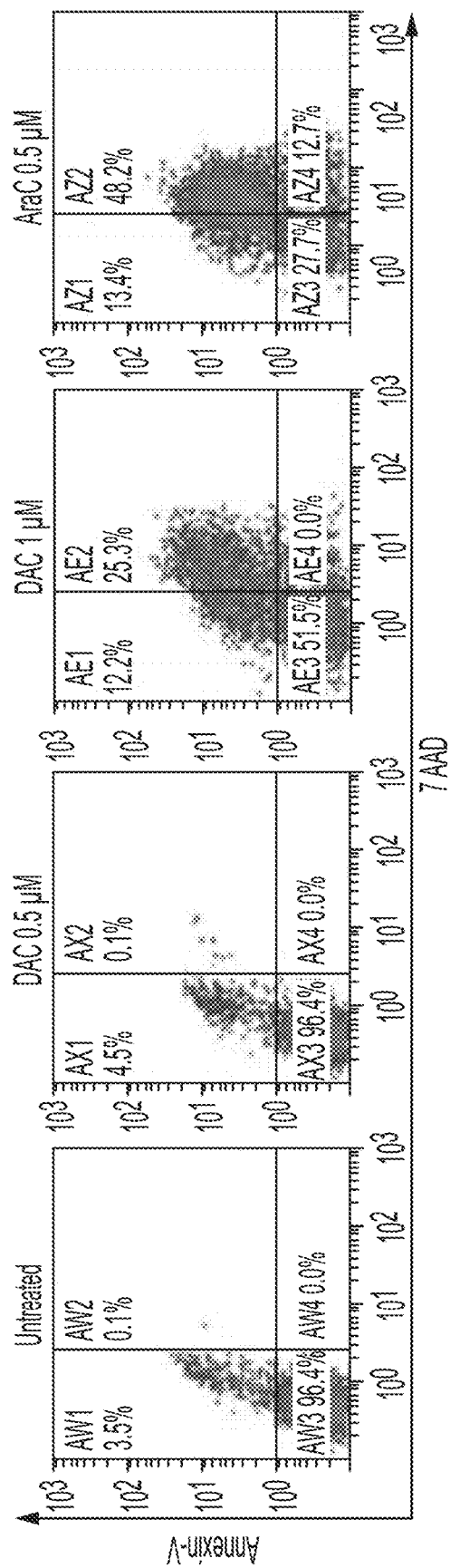
Figure 19E:
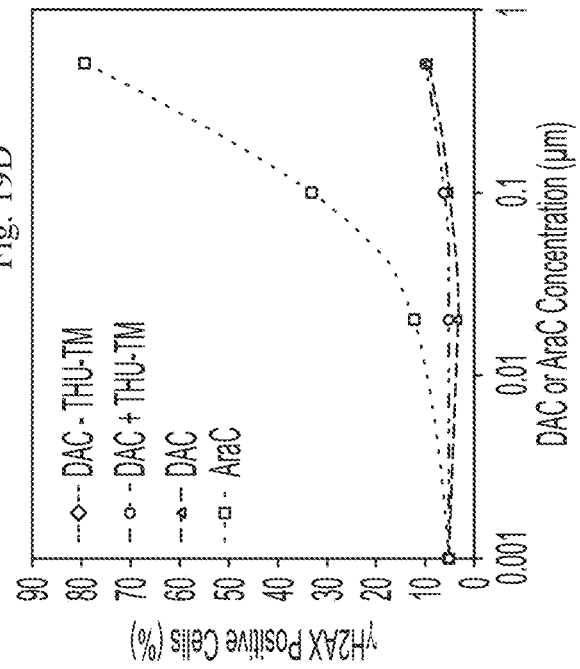

The effects of DAC on DNA damage, apoptosis, and DNMT1 levels in normal CD34$^+$ hematopoietic precursors isolated from cord blood was examined to identify a concentration range that depletes DNMT1 without cytotoxicity. AraC, a cytidine analog that terminates DNA chain synthesis, was used as a positive control for DNA damage and apoptosis induction. DAC 0.005 µM alone and in combination with THU 0.01 µM substantially depleted DNMT1 (FIG. 19A). Concentrations of DAC up to 0.5 µM did not cause measurable DNA damage, as measured by levels of phospho-H2AX (γH2AX) and the Fast Micromethod for DNA scission (FIG. 19B-C), or apoptosis, as measured by annexin staining (FIG. 19D). DAC at 1 µM caused measurable DNA damage and apoptosis (FIG. 19B-D), although not to the same extent as AraC 0.5 µM (FIG. 19B-D). In the presence of THU 0.1 or 100 µM, DAC up to 0.5 µM did not significantly increase DNA damage, as measured by H2AX (FIG. 19E).

Example 26. Effects of Different Routes of Administration on the DAC Concentration-Time Profile In vitro studies have suggested that high peak DAC concentrations are unnecessary for DNMT1 depletion and may increase the risk for cytotoxicity. To compare the effect of different routes of administration on the DAC concentration-time profile, plasma DAC levels were compared after IV or SC administration versus oral administration to the same animals (washout period of ≥2 weeks between drug administrations to the same animal). FIGS. 20A-20D illustrate plasma concentration-time curves following intravenous (IV) decitabine (DAC) 10 mg/m2 (0.5 mg/kg), subcutaneous (SC) DAC 10 mg/m2 (0.5 mg/kg) and oral gavage (Oral) DAC 200 mg/m$^2$ (10 mg/kg) administration to baboons. Some animals also received oral DAC 100 mg/m$^2$ (5 mg/kg) 60 minutes after THU 400 mg/m2 (20 mg/kg). Blood was collected for up to 7 time-points after administration and plasma concentrations were determined using LC/MSMS. The data shows that administration by the oral route produces lower peak levels and a longer half-life than IV or SC administration.

Figures 20A, 20B:
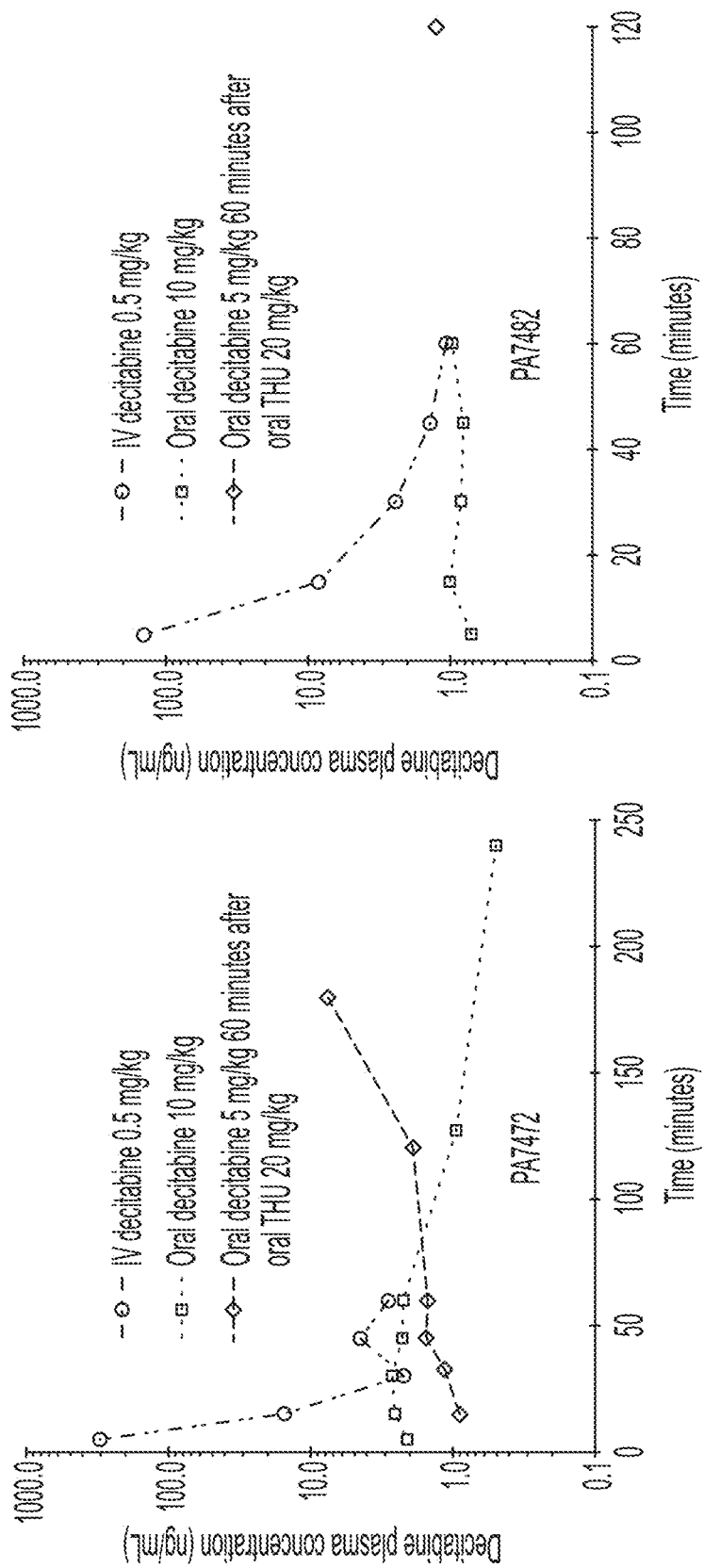
FIGS. 20A-20D illustrates plasma concentration-time curves following intravenous (IV) decitabine (DAC) 10 mg/m2 (0.5 mg/kg), subcutaneous (SC) DAC 10 mg/m2 (0.5 mg/kg) and oral gavage (Oral) DAC 200 mg/m$^2$ (10 mg/kg) administration to baboons.
Figure 20D:
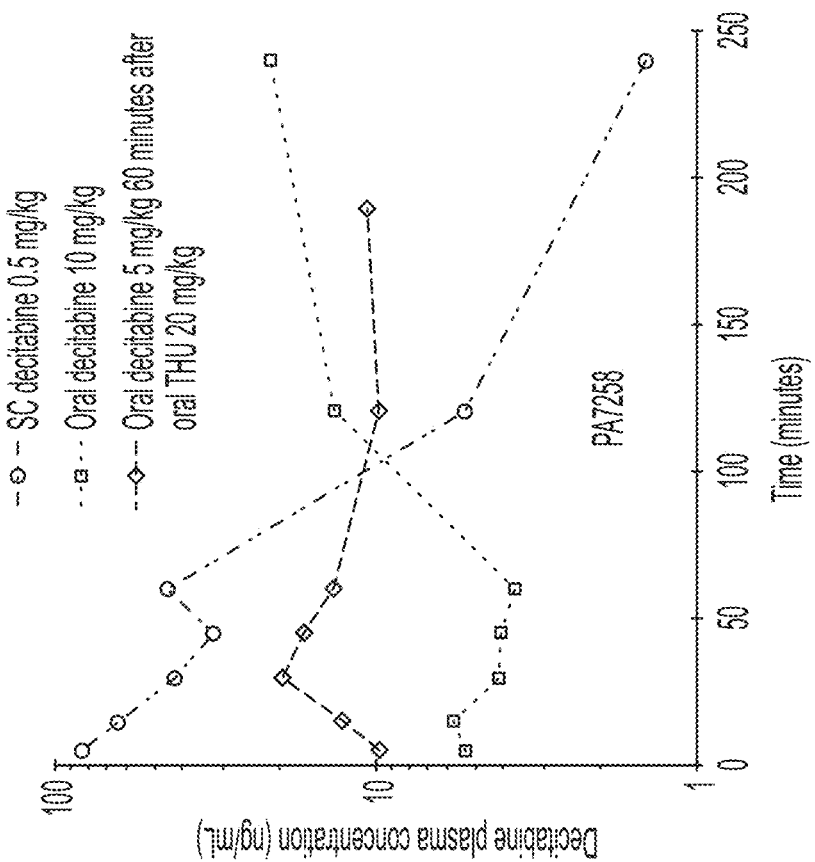
Figure 20C:
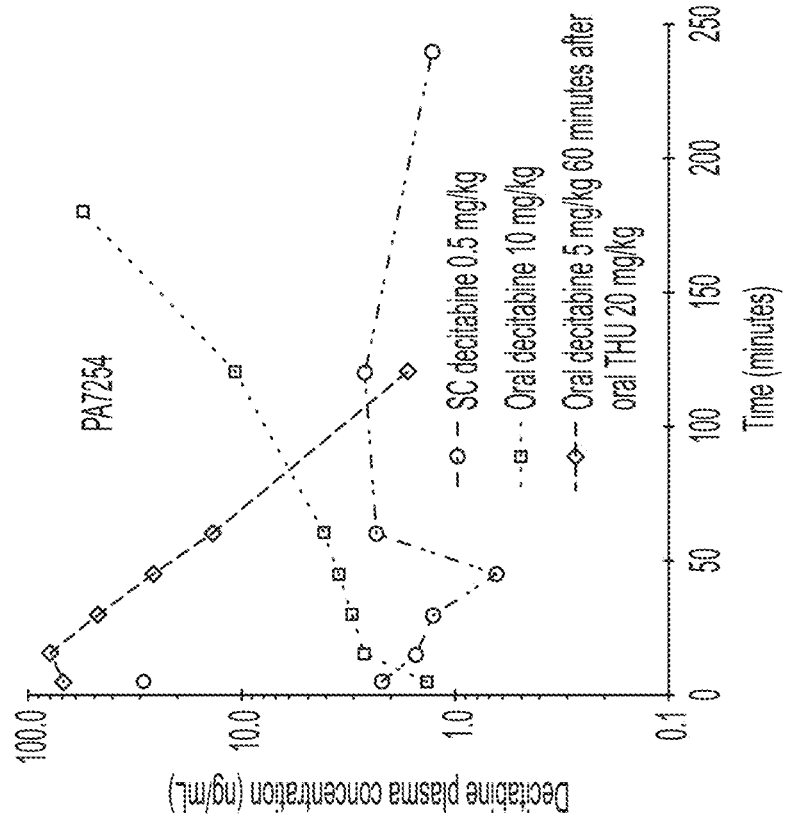

FIG. 20A shows IV and oral administration in PA7472. FIG. 20B shows IV and oral administration in PA7482. FIG. 20C shows SC and oral administration in PA7254. FIG. 20D shows SC and oral administration in PA7258.

In baboon number PA7472, IV DAC 10 mg/m$^2$ produced a peak drug level of >1.3 µM (300 ng/mL) and a half-life <5 minutes. In contrast, the peak drug level with oral DAC 200 mg/m$^2$ was <0.015 µM and half-life >100 minutes (FIG. 20A). A lower peak drug level but longer half-life with oral compared with IV administration was also observed in baboon number PA7482 (FIG. 20B). In baboon number PA7254, SC DAC 10 mg/m$^2$ produced a peak drug level of 0.36 µM and a half-life of <50 minutes. In contrast, the peak drug level with oral DAC 200 mg/m$^2$ was <0.015 µM and the half-life was >150 minutes (FIG. 20C). A lower peak drug level but a longer half-life with oral compared with SC administration was also observed in baboon number PA7258 (FIG. 20D).

Figure 21A:
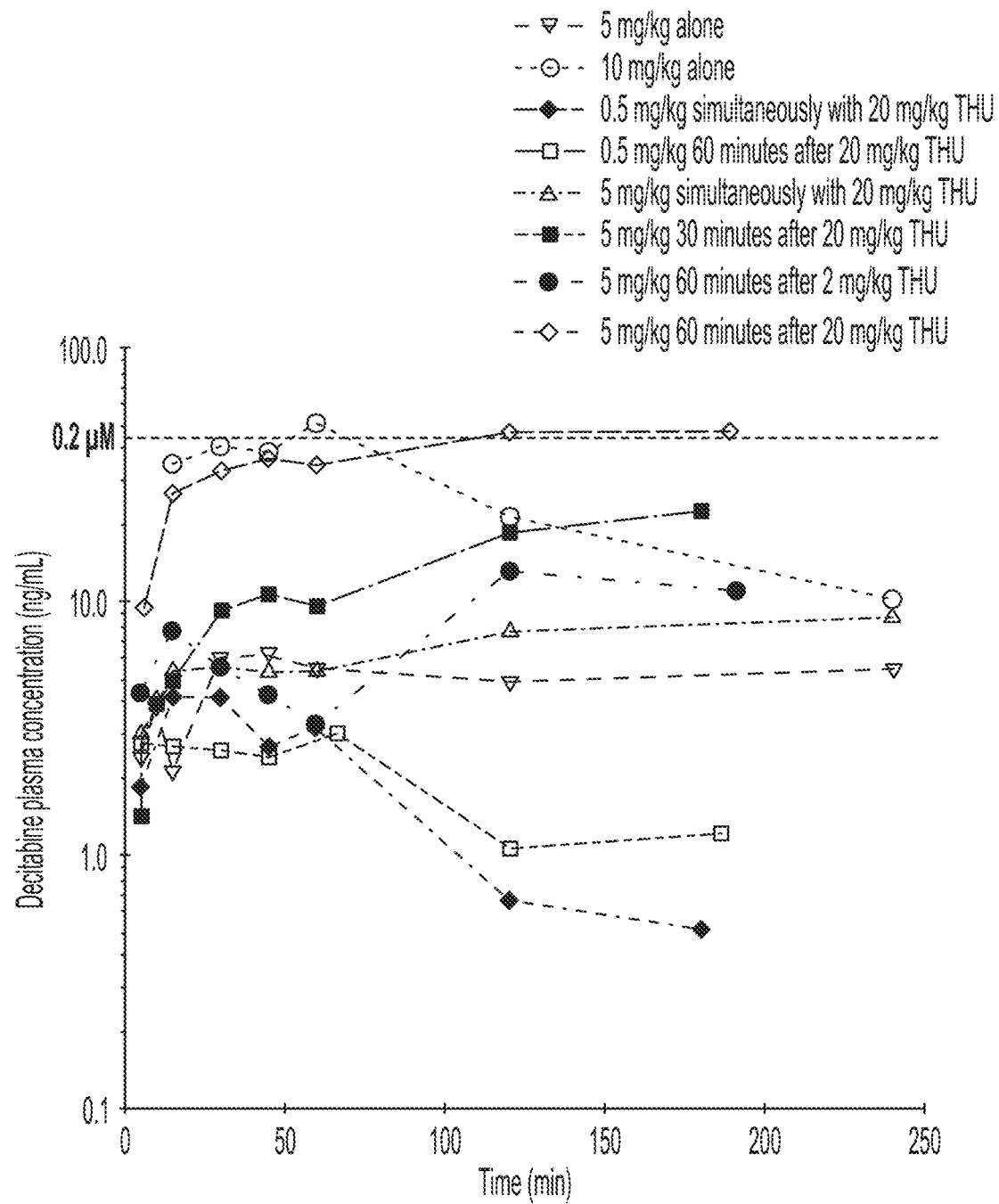
FIGS. 21A-21B illustrates identification of dose and timing of oral THU to increase oral bioavailability of DAC in nonhuman primates. In 2 female baboons, PA7470 and PA7484 (selected for high and low bioavailability of oral DAC alone, respectively), THU 400 mg/m$^2$ (20 mg/kg) 60 minutes before DAC 100 mg/m$^2$ (5 mg/kg) produced higher DAC concentrations than THU 40 mg/m$^2$ (2 mg/kg.
Figure 21B:
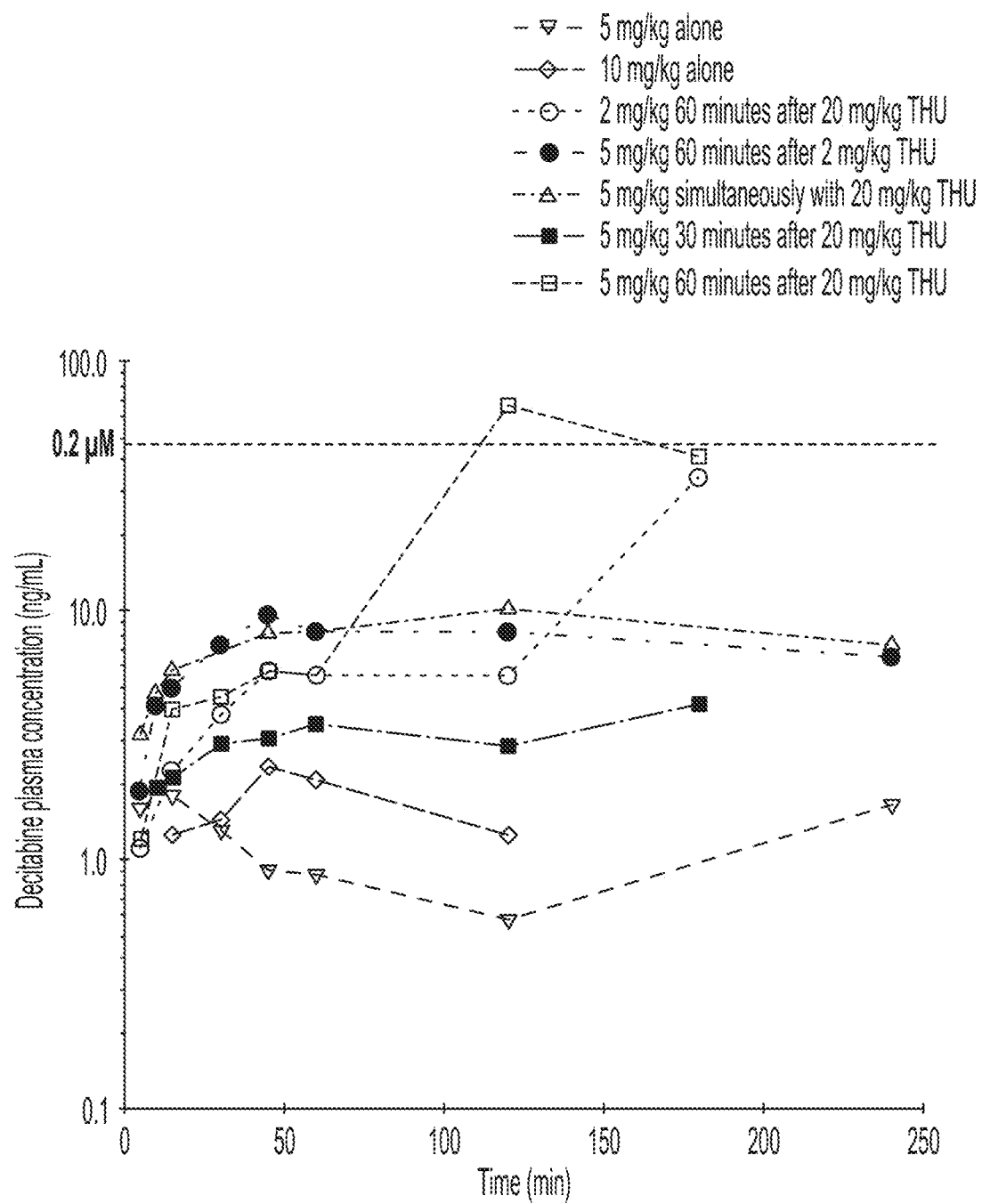

Example 27. Identification of Dose and Timing of Oral THU to Increase Oral Bioavailability of DAC in Nonhuman Primates In 2 female baboons, PA7470 and PA7484 (selected for high and low bioavailability of oral DAC alone, respectively), THU 400 mg/m$^2$ (20 mg/kg) 60 minutes before DAC 100 mg/m$^2$ (5 mg/kg) produced higher DAC concentrations than THU 40 mg/m$^2$ (2 mg/kg; FIG. 21A-B). In these same baboons after a washout period, THU 400 mg/m$^2$ 60 minutes before DAC produced higher DAC concentrations than THU 400 mg/m$^2$ administered simultaneously or 30 minutes before DAC (FIG. 21A-B).

FIG. 21A: Baboon PA7470 treated with different doses of THU and DAC and different timing between the drugs. THU 400 mg/m2 (20 mg/kg) produced higher DAC concentrations than THU 40 mg/m2 (2 mg/kg). THU 400 mg/m2 60 minutes before DAC produced higher DAC concentrations than simultaneous or 30 minute prior administration of THU. FIG. 21B: Baboon PA7484 treated with different doses of THU and DAC and different timing between the drugs. THU 20 mg/kg produced higher DAC concentrations than THU 2 mg/kg. THU 20 mg/kg 60 minutes before DAC produced higher DAC concentrations than simultaneous or 30 minute prior administration of THU.

Example 28. Effect of THU on DAC Oral Bioavailability and Interindividual Variability in Nonhuman Primates Prior administration of oral THU increases oral bioavailability and decreases interindividual variability in pharmacokinetics of DAC. Eight female baboons were treated with oral DAC 200 mg/m$^2$ (10 mg/kg). The median AUClast with oral DAC alone was 463 min/ng/mL, with a range of 190-6279 min/ng/mL, an approximately 33-fold variation, and a coefficient of variation of 1.41 (Table 7 and FIG. 22A).

TABLE 7

AUClast after oral DAC versus oral THU-DAC in the same baboons

| Baboon Number | Weight (kg) | Decitabine 10 mg/kg alone | Decitabine 5 mg/kg alone | THU 20 mg/kg 60 mins before Decitabine 5 mg/kg |
|---|---|---|---|---|
| | | AUC$_{last}$ (min*ng/mL)[#] | | |
| PA7482 | 12.3 | 49.98 | Not done | Not quantifiable |
| PA7484 | 11.5 | 190.35 | 252.73 | 5621.05 |
| PA7256 | 19.8 | 299.02 | Not done | 760.27 |
| PA7472 | 10.7 | 327.25 | Not done | 444.825 |
| PA7254 | 14.4 | 463 | Not done | 2587 |
| PA7255 | 19.9 | 807.8 | Not done | 533.47 |
| PA7258 | 12.6 | 2863.6 | Not done | 2284.48 |
| PA7470 | 9.6 | 6278.78 | 1219.98 | 7515.32 |
| Mean ± SD | | 1604 ± 2262 | | 2821 ± 2749 |
| Median ± IQR | | 463 ± 2565 | | 2284 ± 5088 |
| Median ± IQR per mg of decitabine* | | 160 ± 226 | | 457 ± 1017 |
| Fold-variation | | ~30-fold | | ~14-fold |
| Coefficient of Variation | | 141 | | 97 |

Figure 22A:
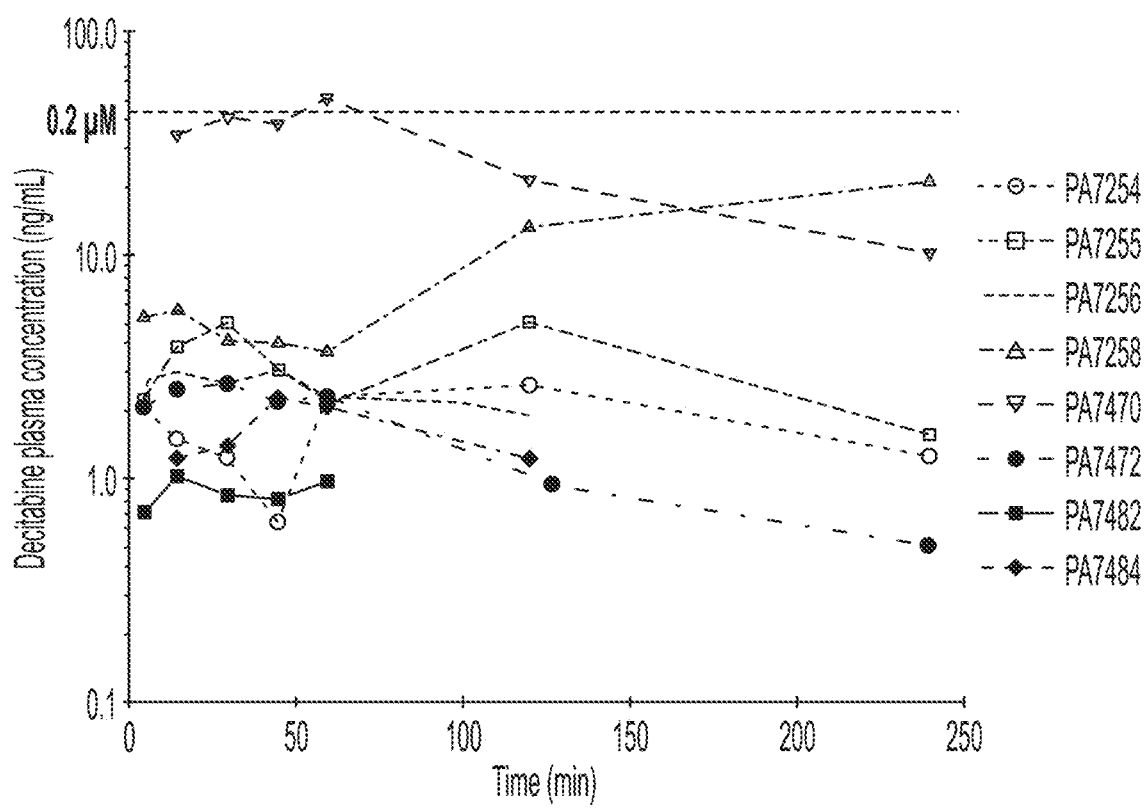
FIGS. 22A-22C illustrates effects of prior administration of oral THU on oral bioavailability and interindividual variability in pharmacokinetics of DAC.
Figure 22B:
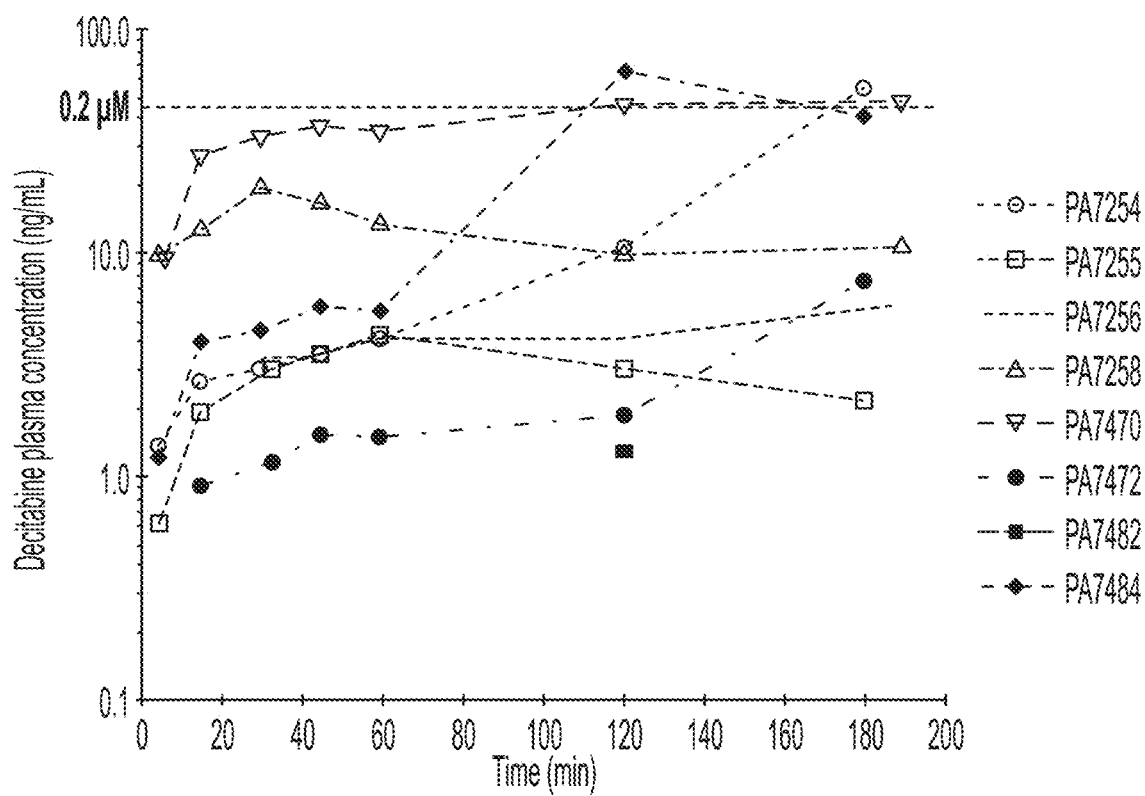

[#]AUC$_{last}$ calculated over 240 minutes for decitabine alone, 180 minutes for THU-decitabine.
*p = 0.02. Wilcoxon test.
SD = standard deviation.
IQR = inter-quartile range After a washout period of >2 weeks, the same animals were treated with DAC 100 mg/m$^2$ (5 mg/kg; half the dose used for the DAC alone experiments) 60 minutes after oral THU 400 mg/m$^2$. The median AUC$_{last}$ with THUDAC was 2284 min/ng/mL, with a range of 534-7515 min/ng/mL, an approximately 14-fold variation, and a coefficient of variation of 0.97 (Table 7 and FIG. 22B). The average DAC Cmax was 0.05 µM (10.85 ng/mL) for DAC alone and 0.12 µM (26.98 ng/mL) for THU-DAC (DAC at half the dose; FIG. 22A-B). The decrease in the coefficient of variation in the THU-DAC group was because the largest AUC$_{last}$ increases occurred in animals that had the poorest bioavailability with DAC alone (Table 1 and FIG. 22C). The AUC$_{last}$ difference between DAC alone and THU-DAC was statistically significant (P=0.02 by Wilcoxon test; Table 7), even though AUC$_{last}$ was calculated at 25% more time for DAC alone (240 minutes vs 180 minutes for THU-DAC). The last measured DAC plasma level was the highest level observed in 4 of 7 THUDAC-treated animals with DAC levels measurable at more than one time point, and half-life was not reached at 180 minutes in any of these 7 animals (FIG. 22B). Therefore, AUC$_{last}$ values for THU-DAC are likely to be underestimates.

Figure 22C:
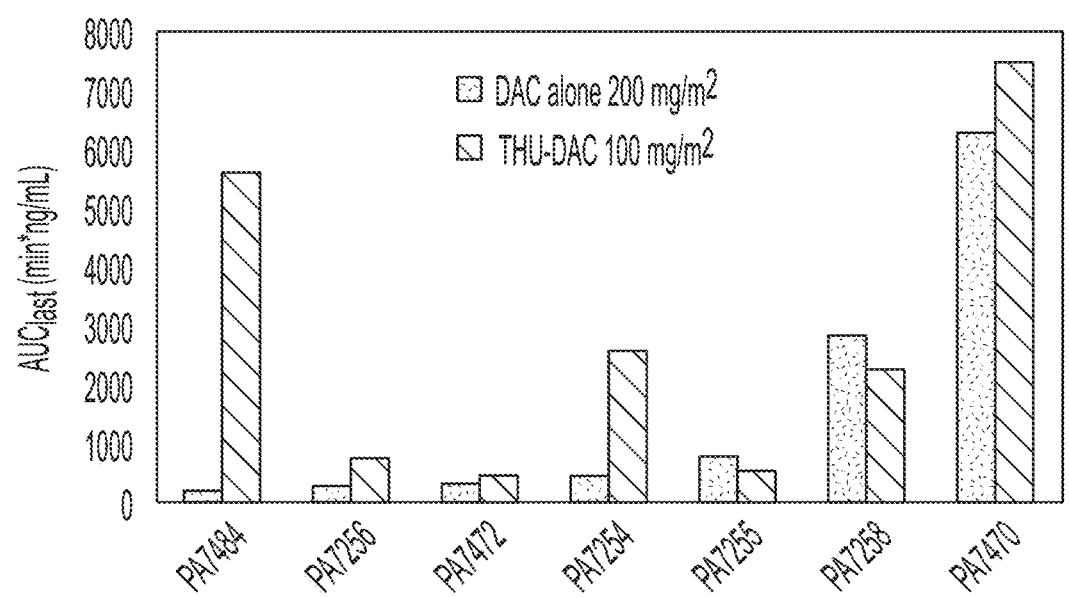

FIG. 22A illustrates DAC concentration-time profiles in 8 baboons administered oral DAC 200 mg/m$^2$ (10 mg/kg). FIG. 22B illustrates DAC concentration-time profiles in the same 8 baboons administered DAC at half the dose (100 mg/m$^2$[5 mg/kg]) 60 minutes after THU 400 mg/m$^2$ (20 mg/kg; THU-DAC). PK measurements went to 180 instead of 240 minutes because of the allowable duration of anesthesia. The largest increases in AUC$_{last}$ with coadministration of THU were seen in animals with lower intrinsic oral bioavailability of DAC (FIG. 22C). Histograms show the distribution of AUC$_{last}$ in 7 animals administered DAC alone versus the same 7 animals receiving DAC at half the dose after THU. AUC measurements went to 180 instead of 240 minutes in the THU-DAC group because of the allowable duration of anesthesia.

Example 29. Effect of THU on Oral DAC Pharmacokinetics in Mice

Figure 23:
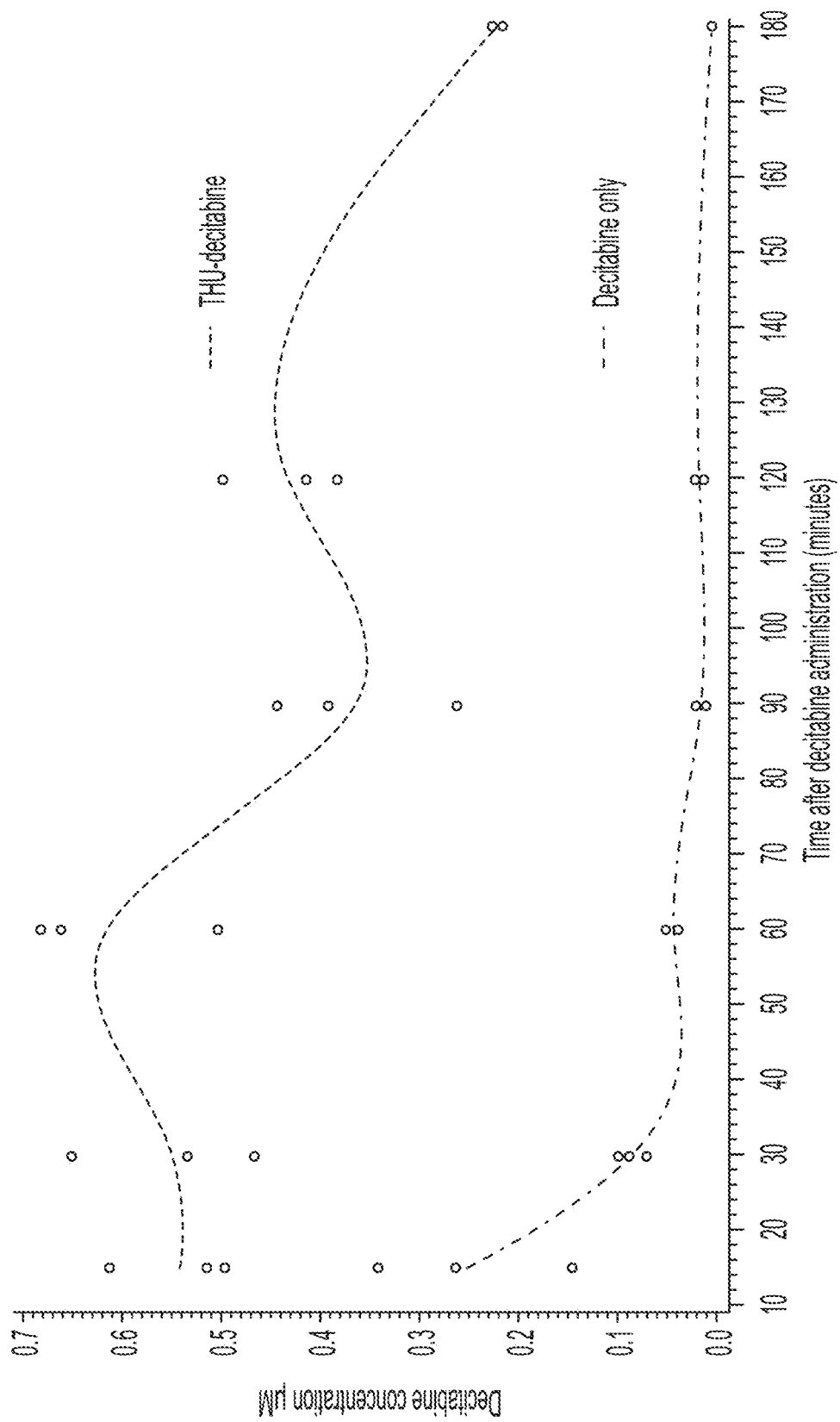
FIG. 23 illustrates the DAC concentration-time profile in mice administered DAC alone or DAC 60 minutes after THU. Drugs were administered by oral gavage. Dots show values from 3 mice for each time point in each treatment group. THU-DAC indicates DAC 0.4 mg/kg 60 minutes after THU 167 mg/kg. DAC indicates DAC 0.4 mg/kg 60 minutes after vehicle.

To more completely evaluate the effect of THU on DAC pharmacokinetics to an extent not possible in nonhuman primate studies, studies were conducted in mice. Using oral gavage, female CD-1 mice were administered THU 400 mg/m$^2$ (167 mg/kg) 60 minutes before DAC 0.3, 0.6, or 1.2 mg/m$^2$ (0.1, 0.2, or 0.4 mg/kg, respectively) or DAC 1.2 mg/m$^2$ alone (vehicle was administered instead of THU) twice a week for 3 weeks, and pharmacokinetics were measured after administration of the last dose (day 16). FIG. 23 illustrates the DAC concentration-time profile in mice administered DAC alone or DAC 60 minutes after THU. Drugs were administered by oral gavage. Dots show values from 3 mice for each time point in each treatment group. THU-DAC indicates DAC 0.4 mg/kg 60 minutes after THU 167 mg/kg. DAC indicates DAC 0.4 mg/kg 60 minutes after vehicle.

THU extended the period of DAC absorption: the concentration-time curve was widened by early and late absorption (2-parallel first-order absorption; FIG. 23). This effect of THU on the shape of the DAC concentration-time profile was reflected in a 9-fold increase in AUC$_{total}$ (from 8.45 min/µM with DAC alone to 76.24 min/µM with THU-DAC), compared with a 2.5-fold increase in Cmax (from 0.251 to 0.617 µM; Table 8). There was a linear relationship between oral THU-DAC dose and DAC Cmax and AUC$_{total}$ (Table 8). The coefficients of variation for AUC$_{total}$ were substantially lower than in baboons: 0.24 for DAC 1.2 mg/m$^2$ alone and 0.15 for THU-DAC 1.2 mg/m$^2$ (Table 8).

TABLE 8

Pharmacokinetic parameters after oral DAC versus oral THU-DAC in female mice (mean values from 3 mice at each time point in each group).

| Group | THU-Dec 0.1 | THU-Dec 0.2 | THU-Dec 0.4 | Dec 0.4 only |
|---|---|---|---|---|
| Decitabine dose, mg/kg | 0.1 | 0.2 | 0.4 | 0.4 |
| THU dose, mg/kg adminstered 60 mins before decitabine) | 167 | 167 | 167 | 0 |
| AUCt (min*µM) | 17.90 | 35.64 | 76.24 | 8.45 |
| Cmax (µM) | 0.138 | 0.338 | 0.617 | 0.251 |

Example 30. Pharmacodynamic Effects in Nonhuman Primates of Repeat-Dose Oral THU-DAC To evaluate pharmacodynamic effects with repeat-dose administration, oral THU-DAC 2×/wk for 8 weeks was administered to 4 baboons. Two animals, one each with relatively low and high oral THU-DAC bioavailability (baboon numbers PA7472 and PA7470, respectively) per the pharmacokinetic studies (Table 7), received oral DAC 5 mg/m$^2$ after oral THU 400 mg/m$^2$. Similarly, a pair of animals from the low and high end of the oral THU-DAC pharmacokinetic range (baboon numbers PA7482 and PA7484, respectively) received oral DAC 10 mg/m$^2$ after oral THU.

Figure 24A:
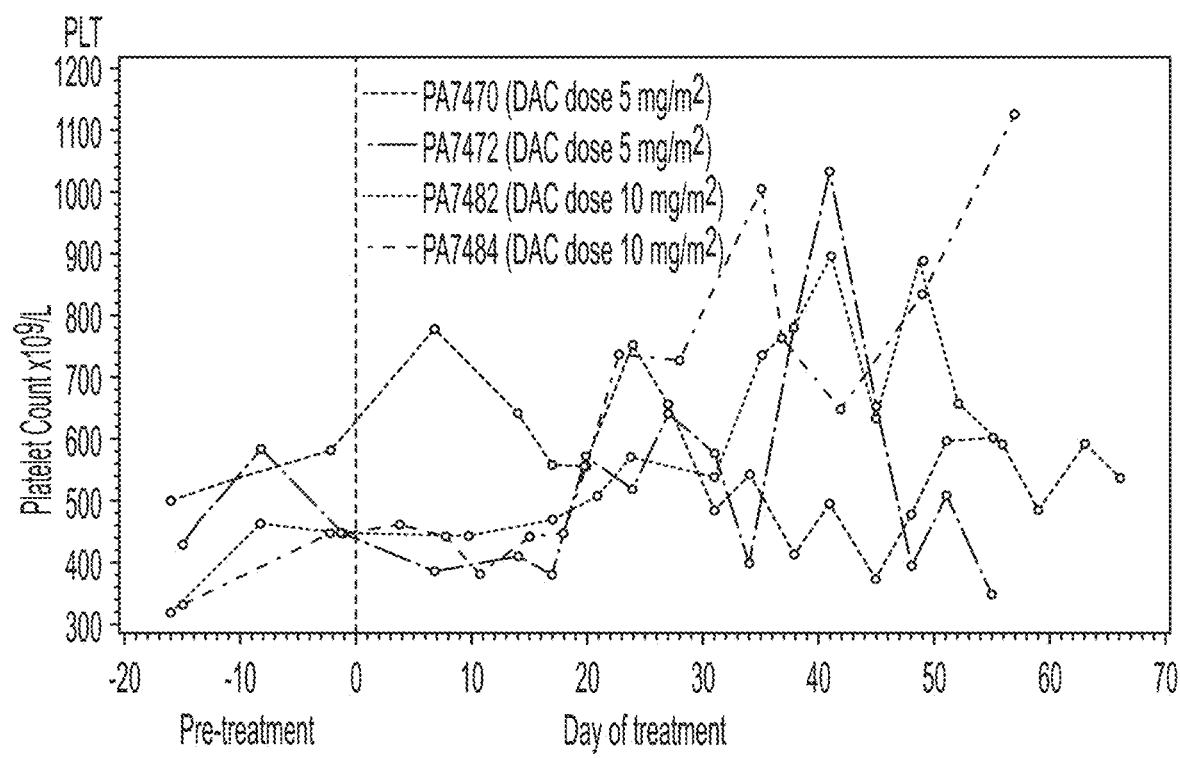
FIGS. 24A-24E illustrates pharmacodynamic effects of repeat dose oral THU-decitabine in non-human primates. A baboon with relatively low and a baboon with relatively high oral THUDAC bioavailability in the pharmacokinetic (PK) studies (baboon numbers PA7472 and PA7470, respectively) received DAC 5 mg/m2, and another pair from each end of the PK range (baboon numbers PA7482 and PA7484, respectively) received DAC 10 mg/m2. DAC was administered 60 minutes after THU 400 mg/m2 2×/wk for 8 weeks.
Figure 24B:
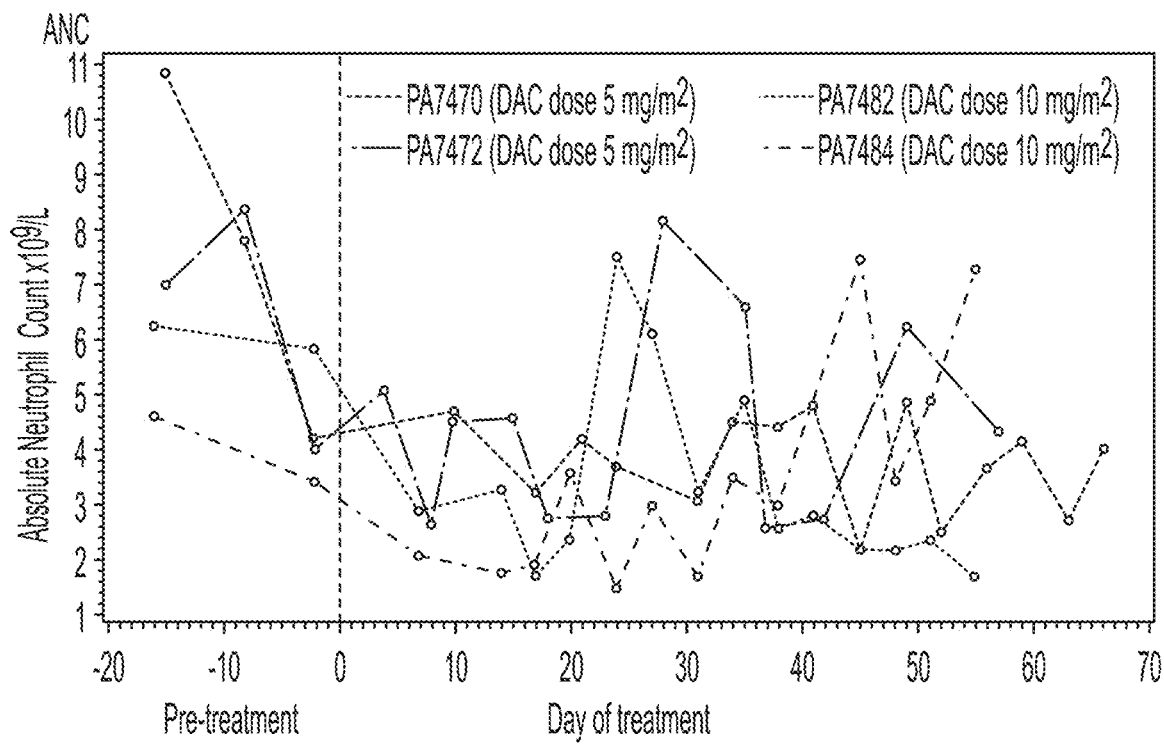
Figure 24C:
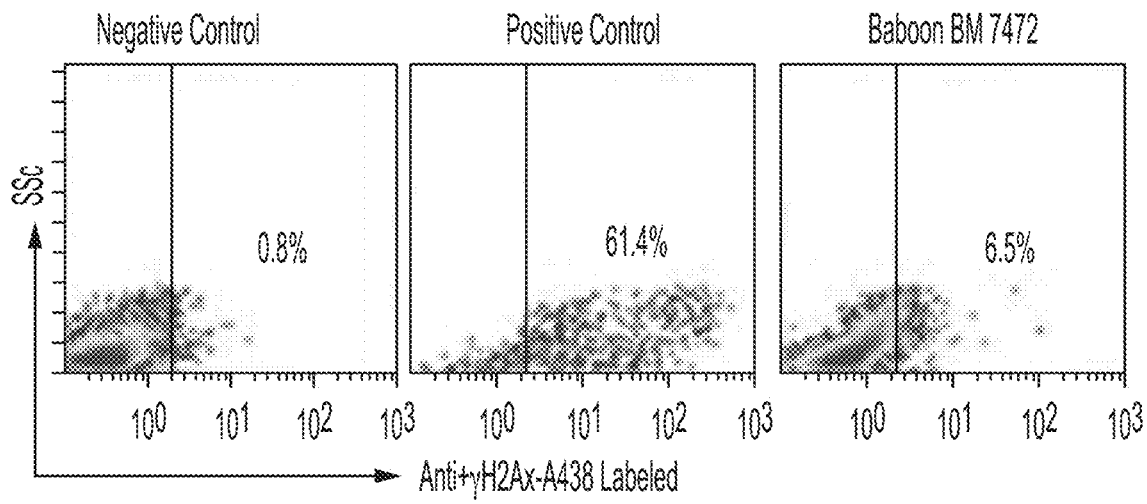
Figure 24D:
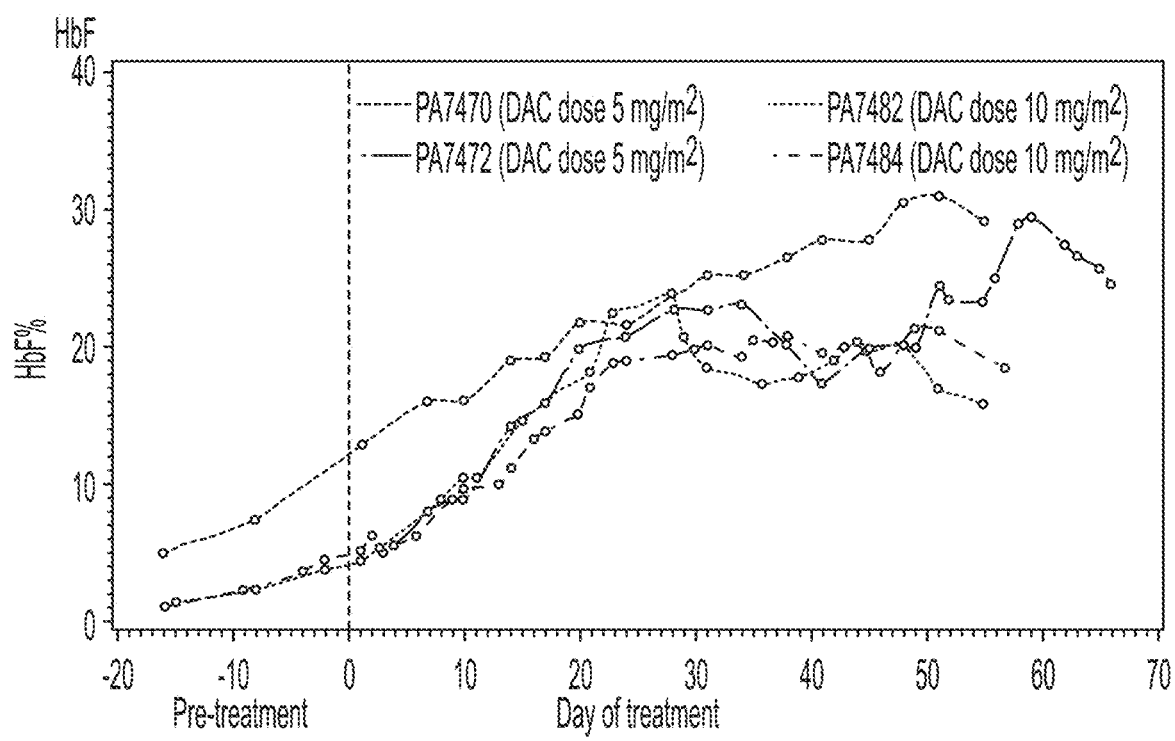
Figure 24E:
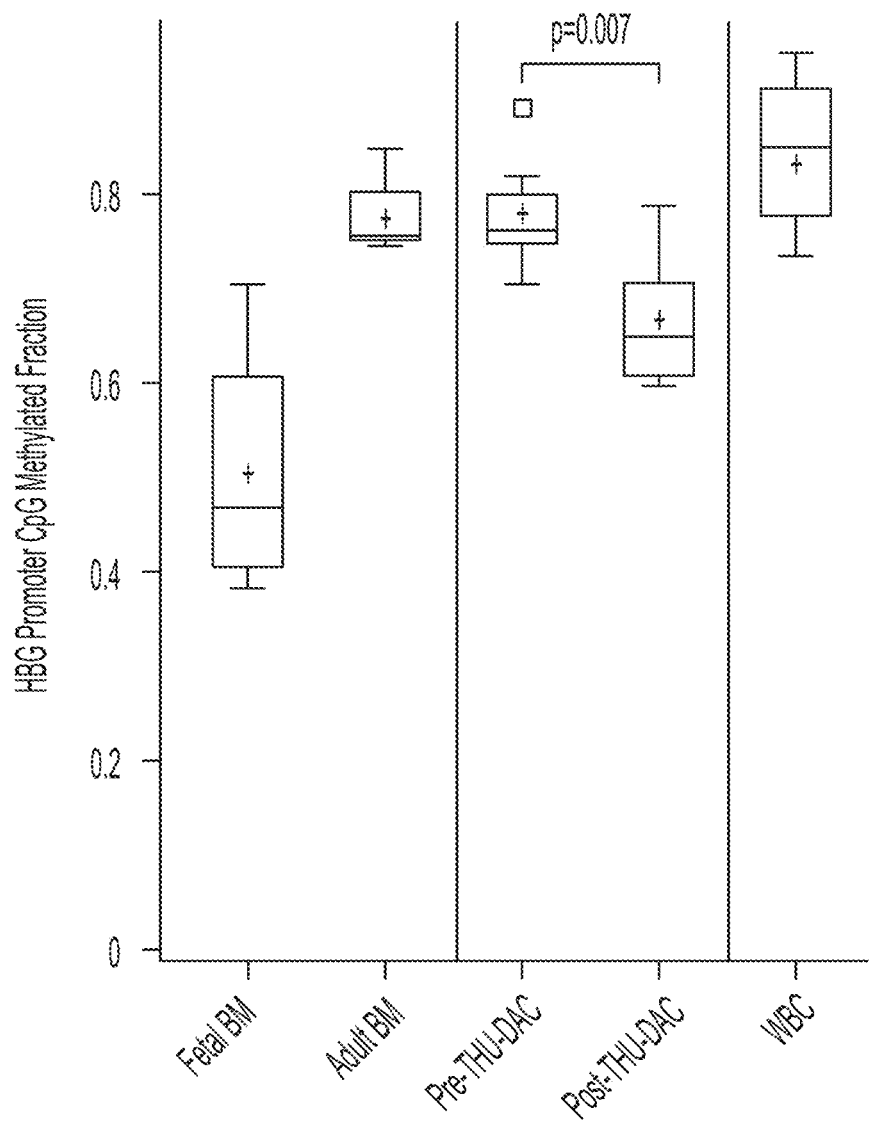
Figure 25A:
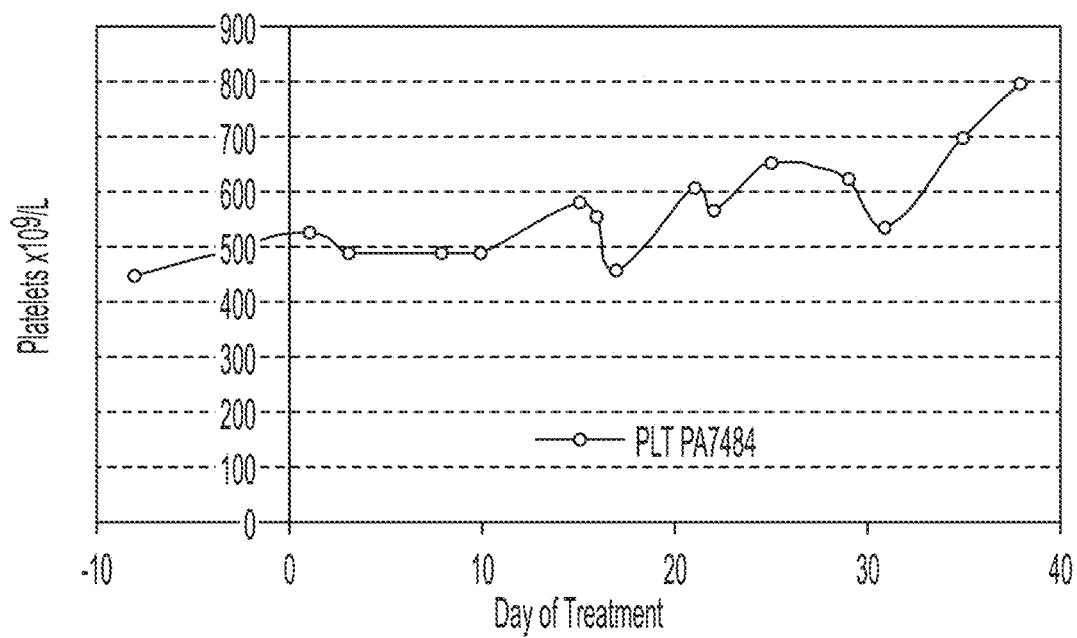
FIGS. 25A-25F illustrates pharmacodynamic effects of repeat dose oral THU-decitabine in non-human primates. Decitabine 5 mg/m2 (PA7484) or 2.5 mg/m2 (PA7472) 60 minutes after THU 400 mg/m2 3×/week was administered for 5 weeks to PA7484 and for 3 weeks to PA7472.
Figure 25B:
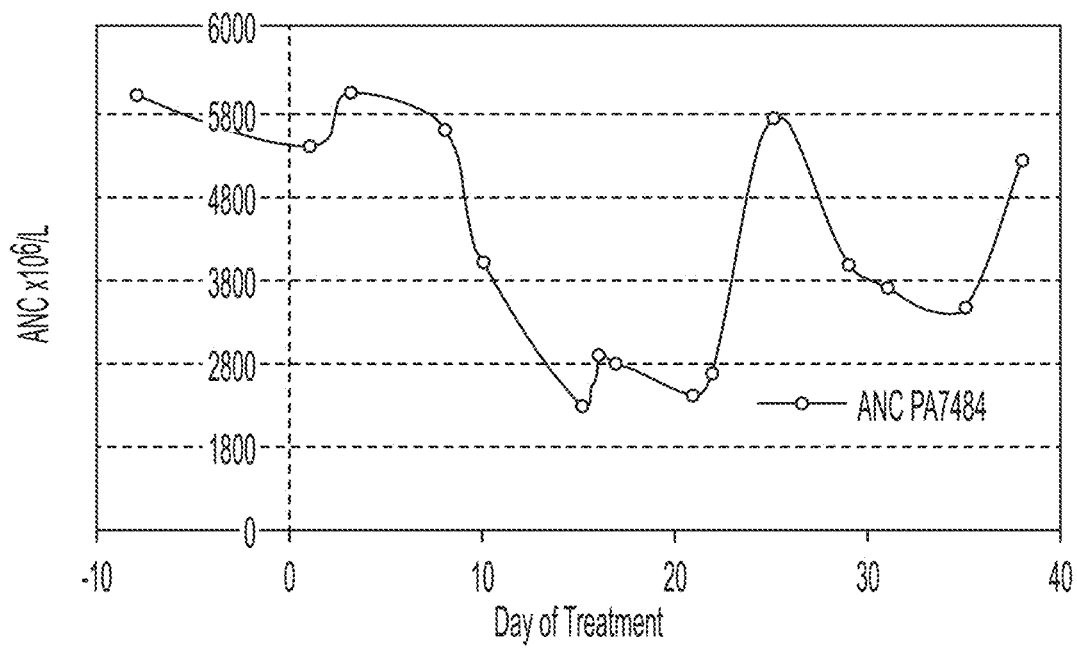
Figure 25C:
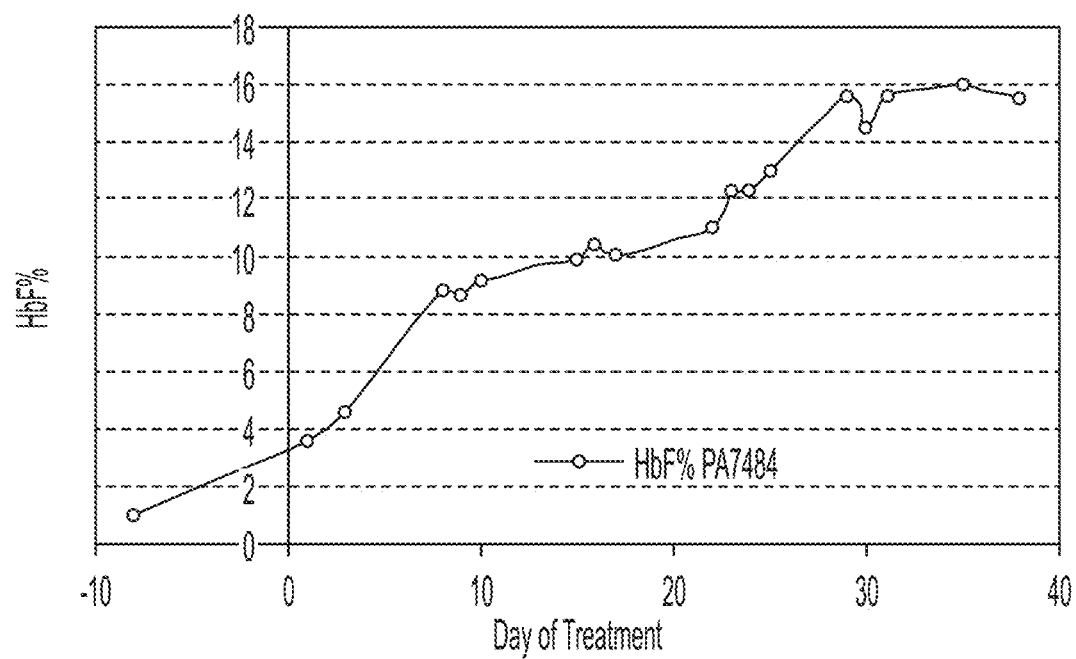
Figure 25D:
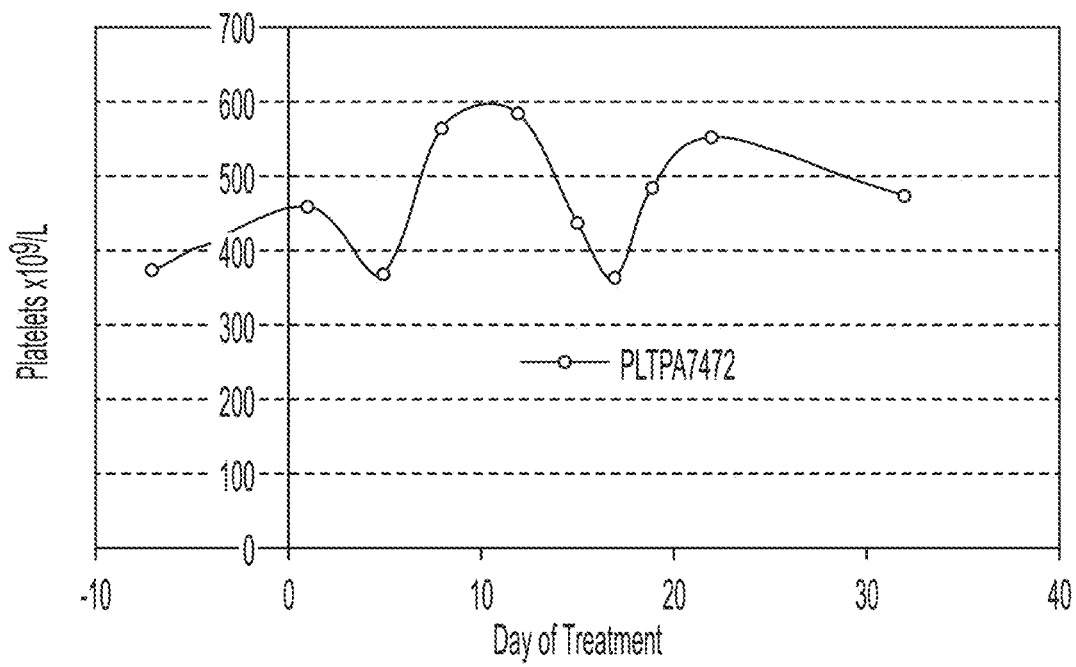
Figure 25E:
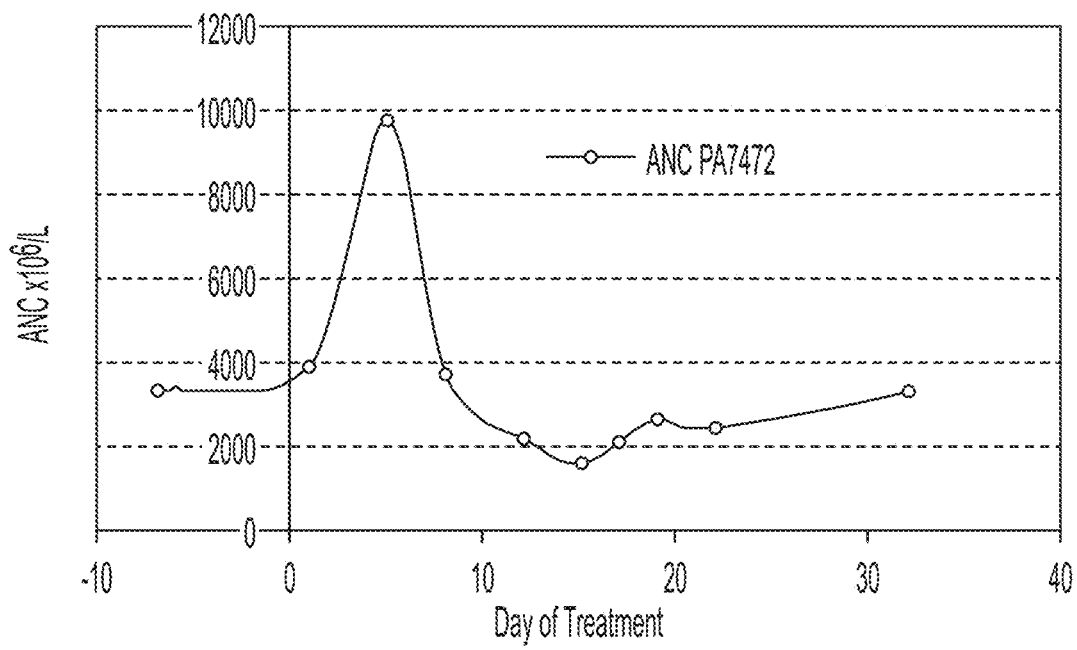
Figure 25F:
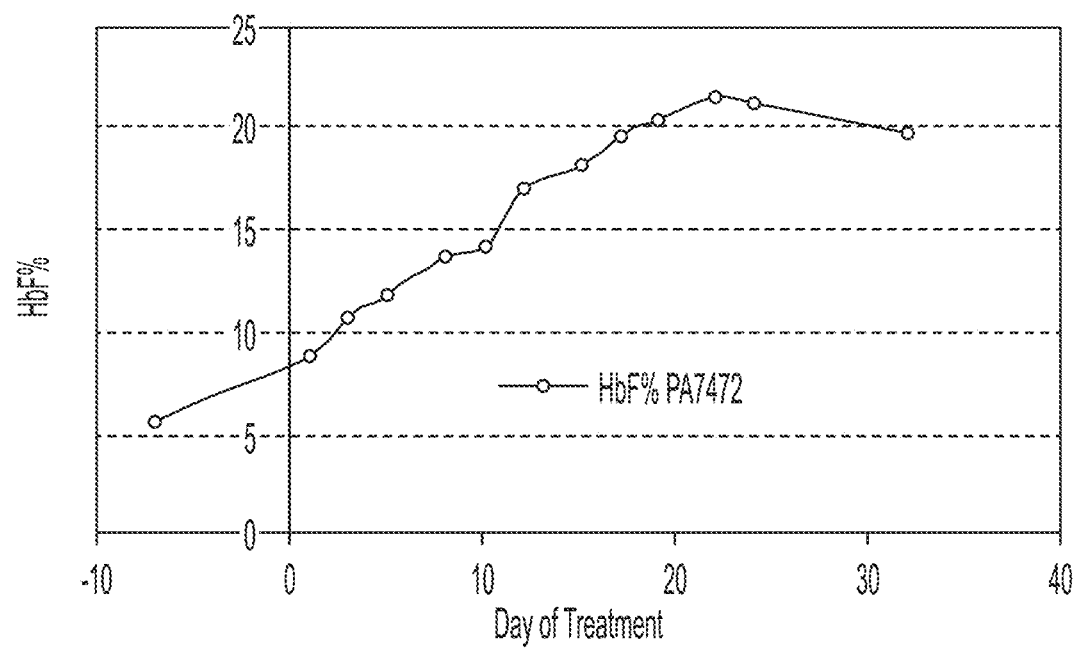

FIGS. 24A-24E and FIGS. 25A-25F illustrate pharmacodynamic effects of repeat dose oral THU-decitabine in non-human primates. In FIGS. 24A-24E, a baboon with relatively low and a baboon with relatively high oral THU-DAC bioavailability in the pharmacokinetic (PK) studies (baboon numbers PA7472 and PA7470, respectively) received DAC 5 mg/m$^2$, and another pair from each end of the PK range (baboon numbers PA7482 and PA7484, respectively) received DAC 10 mg/m$^2$. DAC was administered 60 minutes after THU 400 mg/m² 2×/wk for 8 weeks. FIG. 24A shows platelet counts during drug administration. FIG. 24B shows absolute neutrophil counts during drug administration. FIG. 24C shows phospho-H2AX (γH2AX) labeling of BM cells 96 hours after THU-DAC administration in week 8 in baboon number PA7472. Positive control HeLa cells treated with camptothecin 10 µM. Negative control vehicle treated HeLa cells. FIG. 24D shows HbF expression during treatment. FIG. 24E shows decrease in methylation of developmentally responsive CpG in the γ-globin gene (HBG) promoter after drug administration in baboon numbers PA7472 and PA7484. Based on the human β-globin gene locus (http://www.ncbi.nlm.nih.gov/nuccore/U01317), the coordinates of these CpGs were 33105, 33221, 34425, and 34483. Mass spectrometry was used to measure methylation levels in DNA extracted from erythroid precursors isolated from fetal BM (FBM), adult BM (ABM), before THU-DAC (pre-THU-DAC), and after 8 weeks of 2×/wk oral THU-DAC (post-THU-DAC) in baboon numbers PA7472 and PA7478, and from WBCs. Box-plot boundaries: interquartile range; horizontal line, median; +, mean; small boxes, outlying values; whiskers, range of values. P values are by Wilcoxon test.

In FIGS. 25A-25F, decitabine 5 mg/m2 (PA7484) or 2.5 mg/m2 (PA7472) 60 minutes after THU 400 mg/m2 3×/week was administered for 5 weeks to PA7484 and for 3 weeks to PA7472. First dose day 1, last day of treatment day 31 (PA7484) or day 19 (PA7484). FIG. 24A shows platelet counts in PA7484. FIG. 24B shows absolute neutrophil counts (ANC) in PA7484. FIG. 24C shows HbF % in PA7484. FIG. 24D shows platelet counts in PA7472. FIG. 24E shows ANC in PA7472. FIG. 24F shows HbF % in PA7472.

Oral DAC 5 and 10 mg/m² after THU was expected to produce a $C_{max}$ of approximately 0.006 and 0.012 µM, respectively, because there is a linear relationship between THU-DAC dose and pharmacokinetic parameters (FIGS. 21A-21B and FIGS. 25A-25F), and oral DAC 100 mg/m² after THU produced an average Cmax of 0.12 µM. Noncytotoxic modification of hematopoietic differentiation by DAC is expected to produce increases in platelets and decreases in neutrophil counts, as suggested by previous in vitro and clinical studies. In contrast, cytotoxic therapy is expected to produce concurrent decreases in platelets and neutrophils. In the 4 baboons, platelet counts increased during weeks 1-4 of drug administration (Table 9 and FIG. 24A). Although this upward trend reversed in 2 baboons during weeks 6-8 of drug administration, platelet counts did not decrease below the lower limit of normal (FIG. 24A). Neutrophil counts decreased during weeks 1-3 of drug administration (Table 9 and FIG. 24B), but then increased again or remained stable during weeks 4-8 of drug administration (FIG. 24B). In baboon number PA7472, a BM aspirate 96 hours after THU-DAC administration provided sufficient cells for analysis of DNA damage/repair by γH2AX. There was a small increase in γH2AX compared with negative control that was not suggestive of major DNA damage, although early DNA damage would have been missed (FIG. 24C).

TABLE 9

Repeat-dose administration of oral THU-DAC in 4 baboons: effects on HbF percentage and neutrophil and platelet counts

| Baboon no. | DAC dose, mg/m²* | Schedule | Pretreatment HbF, % | Peak HbF, % | ΔHbF | ANC nadir, × 10⁹/L | Platelet count maximum, × 10⁹/L |
|---|---|---|---|---|---|---|---|
| 7470 | 5 | 2×/wk for 8 wks | 9.9 | 29.3 | 29.3 | 2.13 | 895 |
| 7472 | 5 | 2×/wk for 8 wks | 12.8 | 30.1 | 30.1 | 1.46 | 600 |
| 7482 | 10 | 3×/wk for 3 wks 2×/wk for 5 wks | 3.5 | 23.8 | 20.3 | 2.58 | 1004 |
| 7484 | 10 | 2×/wk for 8 wks | 4.2 | 23.1 | 23.1 | 1.68 | 1029 |

Two of these animals had relatively low bioavailability (baboons PA7472 and PA7482) and 2 had relatively high oral THU-DAC bioavailability (baboons PA7484 and PA7470) according to the pharmacokinetic studies.
ANC indicates absokite netttrophil count.
*Administered after THU 400 mg/m².

In additional experiments, oral THU-DAC was administered 3×/wk with 50% of the various DAC doses, again with concurrent increases in platelet and decreases in neutrophil counts (FIGS. 25A-25F).

One potential application of long-term DNMT1-depleting therapy is to increase HbF (α2γ2) expression to treat hemoglobinopathies such as sickle cell disease and β-thalassemia. In all 4 animals, HbF levels increased progressively during weeks 1-4 of drug administration (Table 9 and FIG. 24D). From weeks 5-8, there was a small decrease from these peak HbF levels in the 2 animals receiving the higher dose of DAC (10 mg/m2), whereas levels continued to increase in the 2 animals receiving DAC 5 mg/m2 (FIG. 24D), producing higher peak HbF levels (Table 9). Progressive HbF increases were also noted with 50% of the DAC doses administered 3×/wk after THU (FIGS. 25A-25F). One intended molecular effect of therapy is to decrease methylation at promoter CpGs that regulate the expression of target genes (e.g., the γ-globin gene [HBG] promoter CpG). Methylation levels of 4 CpG sites in the HBG promoter was measured by mass spectrometric analysis of DNA extracted from BM erythroid precursors (from baboon numbers PA7472 and PA7484). After treatment with oral THU-DAC, the methylation levels of these HBG promoter CpGs decreased by approximately 20% compared with pretreatment methylation levels (P=0.007; FIG. 24E). The relevance of these CpG sites to physiologic regulation of HBG expression was suggested by significant hypomethylation in DNA isolated from fetal BM erythroid precursors versus adult BM erythroid precursors and by significant hypermethylation in DNA isolated from peripheral WBCs (FIG. 24E).

In both baboons and mice, oral administration of THU to inhibit CDA before oral administration of DAC extended DAC absorption time and widened the DAC concentration-time profile, as reflected in mice by a 9-fold increase in DAC $AUC_{total}$ compared with a 2.5-fold increase in DAC Cmax. Because DNMT1 depletion by DAC can occur at very low drug levels but depends on exposure timing, the wider concentration-time profile achieved with oral THU-DAC could have efficacy advantages with regard to DNMT1 depletion without the high peak DAC levels that can cause DNA damage and cytotoxicity.

The baboon model has been accurate and useful in predicting by body surface area scaling a safe human equivalent dose for SC DAC treatment and for combination oral THU and 5-azacytidine therapy. Therefore, the THU dose (400 mg/m$^2$) and timing (60 minutes before DAC) that are likely to be useful for human translation were identified by studies in baboons. In the pharmacokinetic studies in baboons, $AUC_{last}$ estimates for DAC alone were calculated over 240 minutes, whereas estimates for THU-DAC were calculated over 180 minutes (the permissible total duration of anesthesia in the nonhuman primate studies was 240 minutes; therefore, the administration of DAC 60 minutes after THU decreased the duration of sampling in THU-DAC-administered animals). Furthermore, the concentration-time profiles suggested that DAC levels may have continued to increase beyond the last sampling time in many THU-DAC-treated animals. Therefore, the presented values underestimate the increase in DAC bioavailability produced by preceding THU administration in baboons.

Although the murine studies enabled more comprehensive analyses of the effects of THU on DAC pharmacokinetics, dose-exposure extrapolation by body surface area scaling from mice to humans is not useful, because dose for dose, there is a more than 100-fold greater DAC exposure in rodents versus humans. Similarly, there is more than 100-fold greater exposure of the cytidine analog AraC in mice versus monkeys dose for dose. The reasons for this log-scale increase in cytidine analog exposure in rodents compared with primates are unknown.

An important limitation of DAC and other cytidine analogs has been the inter-individual variations in pharmacokinetics, toxicity, and efficacy that are associated with single nucleotide polymorphisms in CDA. THU, by inhibiting CDA, may attenuate the role of these pharmacogenetic variations in cytidine analog pharmacokinetics and pharmacodynamics. For example, in baboons, THU decreased substantial interindividual variability in DAC pharmacokinetics compared with oral DAC alone. Similarly, THU decreased substantial interindividual variability in HbF elevations (peak levels ranged between 23% and 30%) compared with previous experience with oral DAC alone (peak levels ranged from 10%-60%). However, the basis for interindividual variability in baboons has not been characterized. Consistent with a genetic contribution to interindividual variability, variability in mice of the same gender was substantially less than in baboons.

Combination therapy with THU may offer other advantages, because CDA up-regulation is a putative mechanism of cancer cell resistance to cytidine analogs, and cancer cells may find sanctuary from cytidine analogs in tissues expressing high levels of CDA.

One potential clinical application of DNMT1-targeted therapy is to increase HbF expression as a treatment for sickle cell disease and β-thalassemia. In baboons, repeat administration of oral THU-DAC using a DAC dose that would produce peak DAC concentrations less than 0.2 µM was not myelotoxic, hypomethylated HBG promoter CpG, and produced large cumulative increases in HbF expression in RBCs.

For the purposes of targeting DNMT1, the RNA incorporation that occurs with 5-azacytidine is an off-target effect. Although the present data indicate that noncytotoxic DNMT1 depletion with DAC is possible, DNMT1 depletion occurs after DNA incorporation of DAC and postreplicative immobilization of DNMT1, and therefore genotoxicity remains a possible side effect that will have to be evaluated in clinical studies with oral THU-DAC. In conclusion, in baboons and mice, preceding administration of oral THU substantially increases oral bioavailability of DAC, creates a concentration-time profile that suits the purpose of DNMT1 depletion with less cytotoxicity, and decreases interindividual variability. Therefore, combination oral THU-DAC may facilitate more accessible, safe, and efficacious DNMT1-targeted therapy.

Surprisingly, while the baboons receiving the 10 mg/m$^2$ dose of DAC showed a decrease from peak HbF levels in weeks 5-8, HbF levels continued to increase in the baboons receiving DAC 5 mg/m$^2$ (FIG. 24D), resulting in higher peak HbF levels (see Table 9). Progressive HbF increases were also noted with 50% of the DAC doses administered 3×/wk after THU (FIGS. 25A-25F).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A composition for oral administration comprising about 10 to about 150 mg/m decitabine and about 100 to about 500 mg/m tetrahydrouridine and a pharmaceutically acceptable excipient, wherein the tetrahydrouridine is located on a surface of a capsule or tablet and the decitabine is located within the capsule or tablet.

2. The composition of claim 1, wherein the tetrahydrouridine is bio-available about 15 to about 180 minutes before the decitabine.

3. The composition of claim 1, wherein the composition is in form of the tablet.

4. The composition of claim 1, wherein the composition is in form of the capsule.

5. The composition of claim 1, wherein the composition is effective to produce a decitabine plasma concentration of 0.005 µM to 0.05 µM in a human subject for at least 60 minutes, wherein the decitabine plasma concentration does not exceed 0.2 µM.

6. The composition of claim 1, wherein the composition comprises decitabine and tetrahydrouridine in amounts effective to cause a decitabine plasma concentration of between 0.005 µM and 0.1 µM in a human subject for at least 60 minute.

7. The composition of claim 1, wherein the decitabine is present in an amount effective for treating blood disorder in a subject.

8. A method for treating a hematological or solid malignancy in a subject, the method comprising administering to the subject the composition of claim 1.

9. The method of claim 8, wherein the method further comprises administering to the subject an additional therapy selected from surgery, radiation, or cytotoxic chemotherapy.

10. The method of claim 9, wherein the cytotoxic chemotherapy comprises administering an anti-cancer agent to the subject.

11. The method of claim 10, wherein the anticancer agent is selected from the group consisting of anti-microtubule agents, topoisomerase inhibitors, antimetabolites, mitotic inhibitors, alkylating agents, intercalating agents, agents capable of interfering with a signal transduction pathway, agents that promote apoptosis, and antibodies against other tumor-associated antigens.

12. The method of claim 11, wherein the anticancer agent is an antimetabolite selected from the group consisting of 5-azacytidine, 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 9-β-D-arabinofuranosyladenine (ara-A), cladribine, 5-fluorouridine, Floxuridine (FUDR), tiazofurin, and N-[5-[N-(3,4-dihydro-2-methyl-4-oxoquinazolin-6-ylmethyl)-N-methylamino]-2-thenoyl]-L-glutamic acid.

13. The method of claim 9, wherein the additional therapy is performed sequentially before the administration of decitabine and tetrahydrouridine.

14. The method of claim 9, wherein the additional therapy is performed sequentially after the administration of decitabine and tetrahydrouridine.

\* \* \* \* \*